(12) United States Patent
Braido et al.

(10) Patent No.: US 9,241,794 B2
(45) Date of Patent: Jan. 26, 2016

(54) COLLAPSIBLE PROSTHETIC HEART VALVES

(71) Applicant: St. Jude Medical, Inc., St. Paul, MN (US)

(72) Inventors: Peter Nicholas Braido, Linwood, MN (US); Andrea L. McCarthy, Vadnais Heights, MN (US); Rubem L. Figueiredo, Contagem (BR); Julia A. Schraut, St. Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 14/334,059

(22) Filed: Jul. 17, 2014

(65) Prior Publication Data

US 2015/0081013 A1  Mar. 19, 2015

Related U.S. Application Data

(63) Continuation of application No. 13/848,466, filed on Mar. 21, 2013, now Pat. No. 8,845,721, which is a continuation of application No. 12/733,759, filed as application No. PCT/US2008/011153 on Sep. 26, 2008, now Pat. No. 8,425,593.

(60) Provisional application No. 60/995,648, filed on Sep. 26, 2007.

(51) Int. Cl.
*A61F 2/24* (2006.01)

(52) U.S. Cl.
CPC ............. *A61F 2/2418* (2013.01); *A61F 2/2403* (2013.01); *A61F 2/2412* (2013.01); *A61F 2/2415* (2013.01); *A61F 2220/0075* (2013.01); *A61F 2230/0054* (2013.01)

(58) Field of Classification Search
CPC ........ A61F 2/2412; A61F 2/2418; A61F 2/24
USPC ................................................ 623/2.11–1.19
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

Extended European Search Report for Application No. EP 12196437 dated Aug. 13, 2013.

(Continued)

*Primary Examiner* — Suzette J Gherbi
(74) *Attorney, Agent, or Firm* — Lerner, David, Littenberg, Krumholz & Mentlik, LLP

(57) ABSTRACT

Prosthetic heart valves, which are collapsible to a relatively small circumferential size for less invasive delivery into a patient and which then re-expand to operating size at an implant site in the patient, include a collapsible/expandable stent-like supporting structure and various components of flexible, sheet-like material that are attached to the supporting structure. For example, these sheet-like other components may include prosthetic valve leaflets, layers of buffering material, cuff material, etc. Improved structures and techniques are provided for securing such other components to the stent-like supporting structure of the valve.

6 Claims, 69 Drawing Sheets

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,759,758 A | 7/1988 | Gabbay |
| 4,922,905 A | 5/1990 | Strecker |
| 5,411,552 A | 5/1995 | Andersen et al. |
| 5,480,423 A | 1/1996 | Ravenscroft et al. |
| 5,843,167 A | 12/1998 | Dwyer et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,129,758 A | 10/2000 | Love |
| 6,168,614 B1 | 1/2001 | Andersen et al. |
| 6,214,036 B1 | 4/2001 | Letendre et al. |
| 6,264,691 B1 * | 7/2001 | Gabbay ............... 623/2.14 |
| 6,267,783 B1 | 7/2001 | Letendre et al. |
| 6,306,141 B1 | 10/2001 | Jervis |
| 6,312,465 B1 | 11/2001 | Griffin et al. |
| 6,358,277 B1 | 3/2002 | Duran |
| 6,368,348 B1 | 4/2002 | Gabbay |
| 6,419,695 B1 | 7/2002 | Gabbay |
| 6,454,799 B1 | 9/2002 | Schreck |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,733,525 B2 | 5/2004 | Yang et al. |
| 6,767,362 B2 * | 7/2004 | Schreck ............... 623/2.11 |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,830,585 B1 | 12/2004 | Artof et al. |
| 6,869,444 B2 | 3/2005 | Gabbay |
| 6,875,231 B2 | 4/2005 | Anduiza et al. |
| 6,893,460 B2 | 5/2005 | Spenser et al. |
| 6,908,481 B2 | 6/2005 | Cribier |
| 6,916,338 B2 | 7/2005 | Speziali |
| 6,951,573 B1 | 10/2005 | Dilling |
| 7,018,406 B2 | 3/2006 | Seguin et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,331,993 B2 | 2/2008 | White |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| 8,137,398 B2 | 3/2012 | Tuval et al. |
| 8,142,497 B2 | 3/2012 | Friedman |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,685 B2 | 6/2013 | Hariton et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |

(56) References Cited

U.S. PATENT DOCUMENTS

| | | |
|---|---|---|
| 2003/0050694 A1 | 3/2003 | Yang et al. |
| 2003/0055495 A1 | 3/2003 | Pease et al. |
| 2003/0055496 A1 | 3/2003 | Cai et al. |
| 2003/0130726 A1 | 7/2003 | Thorpe et al. |
| 2003/0153974 A1 | 8/2003 | Spenser et al. |
| 2003/0153975 A1 | 8/2003 | Byrd et al. |
| 2004/0039436 A1 | 2/2004 | Spenser et al. |
| 2004/0049262 A1 | 3/2004 | Obermiller et al. |
| 2004/0088046 A1 | 5/2004 | Speziali |
| 2004/0093060 A1 | 5/2004 | Seguin et al. |
| 2004/0093075 A1 | 5/2004 | Kuehne |
| 2004/0111111 A1 | 6/2004 | Lin |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0177227 A1 | 8/2005 | Heim et al. |
| 2005/0192665 A1 | 9/2005 | Spenser et al. |
| 2005/0197695 A1 | 9/2005 | Stacchino et al. |
| 2005/0203605 A1 | 9/2005 | Dolan |
| 2005/0209689 A1 | 9/2005 | Speziali |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0161249 A1 | 7/2006 | Realyvasquez et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0208327 A1* | 8/2008 | Rowe .................. 623/2.11 |
| 2008/0228263 A1 | 9/2008 | Ryan |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2008/0275548 A1* | 11/2008 | Svensson ................. 623/2.1 |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0114307 A1 | 5/2010 | Agnew et al. |
| 2010/0131054 A1 | 5/2010 | Tuval et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1* | 7/2010 | Toomes et al. ........... 623/2.18 |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0224678 A1 | 9/2011 | Gabbay |
| 2011/0264206 A1 | 10/2011 | Tabor |
| 2012/0035722 A1 | 2/2012 | Tuval |
| 2012/0078347 A1 | 3/2012 | Braido et al. |
| 2012/0083879 A1* | 4/2012 | Eberhardt et al. ......... 623/2.18 |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0330347 A1* | 11/2014 | Weston et al. ........... 623/2.18 |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| EP | 2537487 A1 | 12/2012 |
| FR | 2847800 A1 | 6/2004 |
| JP | 2000511459 A | 9/2000 |
| JP | 2007534381 A | 11/2007 |
| JP | 2008539985 A | 11/2008 |
| WO | 9117720 A1 | 11/1991 |
| WO | 9716133 A1 | 5/1997 |
| WO | 9832412 A2 | 7/1998 |
| WO | 9843556 A1 | 10/1998 |
| WO | 9913801 A1 | 3/1999 |
| WO | 0128459 A1 | 4/2001 |
| WO | 0149213 A2 | 7/2001 |

(56) References Cited

FOREIGN PATENT DOCUMENTS

| WO | 0106500 | A2 | 8/2001 |
|---|---|---|---|
| WO | 0154625 | A1 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 2005102015 | A2 | 11/2005 |
| WO | 2006073626 | A2 | 7/2006 |
| WO | 2006124649 | A2 | 11/2006 |
| WO | 2007071436 | A2 | 6/2007 |
| WO | 2008070797 | A2 | 6/2008 |
| WO | 2010008548 | A2 | 1/2010 |
| WO | 2010008549 | A1 | 1/2010 |
| WO | 2010051025 | A1 | 5/2010 |
| WO | 2010087975 | A1 | 8/2010 |
| WO | 2010096176 | A1 | 8/2010 |
| WO | 2010098857 | A1 | 9/2010 |

OTHER PUBLICATIONS

International Search Report for Application No. PCT/US2008/011153 dated Apr. 15, 2009.
U.S. Appl. No. 29/375,232.
U.S. Appl. No. 29/375,235.
U.S. Appl. No. 29/375,238.
U.S. Appl. No. 29/375,239.
U.S. Appl. No. 29/375,243.
U.S. Appl. No. 29/375,245.
U.S. Appl. No. 29/375,251.
U.S. Appl. No. 29/375,252.
U.S. Appl. No. 29/375,253.
U.S. Appl. No. 29/375,254.
U.S. Appl. No. 29/375,257.
U.S. Appl. No. 29/375,258.
U.S. Appl. No. 29/375,260.
European Communication for Application No. 08834463.5 dated Jun. 22, 2015.
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?μm Microsecond Laser Radiation. Journal of Cardiac Surgery, 30: 157-162. doi: 10.1111/jocs.12481.
Muñoz, Daniel Rodriguez, Carla Lázaro Rivera, and José Luis Zamorano Gómez. "Guidance of treatment of perivalvular prosthetic leaks." Current cardiology reports 16.1 (2014): 1-6.
Gössl, Mario, and Charanjit S. Rihal. "Percutaneous treatment of aortic and mitral valve paravalvular regurgitation." Current cardiology reports 15.8 (2013): 1-8.
Swiatkiewicz, Iwona, et al. "Percutaneous closure of mitral perivalvular leak." Kardiologia polska 67.7 (2009): 762.
De Cicco, Giuseppe, et al. "Aortic valve periprosthetic leakage: anatomic observations and surgical results." The Annals of thoracic surgery 79.5 (2005): 1480-1485.
Transcatheter Umbrella Closure of Valvular and Paravalvular Leaks, Hourihan et al., Journal of the American College of Cardiology, vol. 20, No. 6, pp. 1371-1377, (1992).
Buellesfeld et al., Treatment of paravalvular leaks through inverventional techniques; Department of Cardiology, Ben University Hospital 2011.

\* cited by examiner

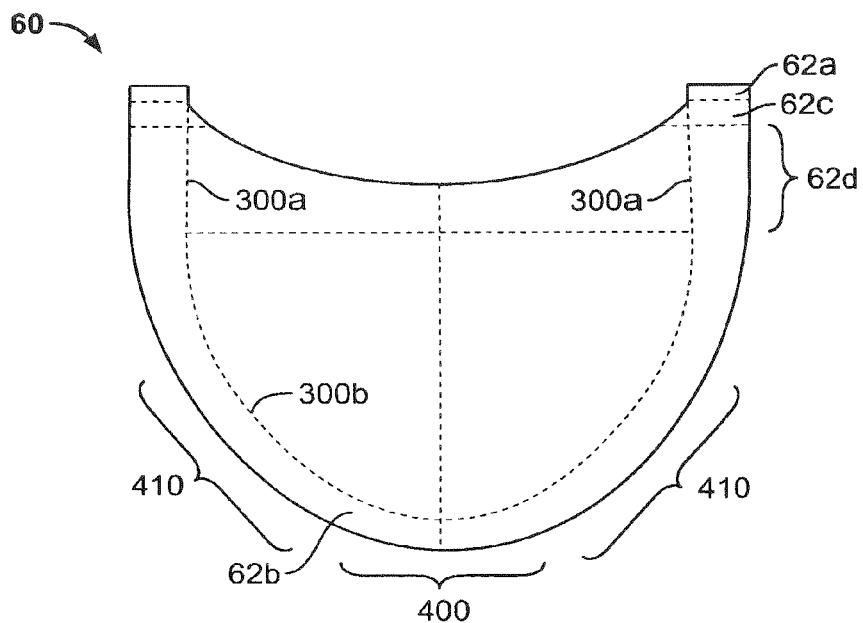
FIG. 62
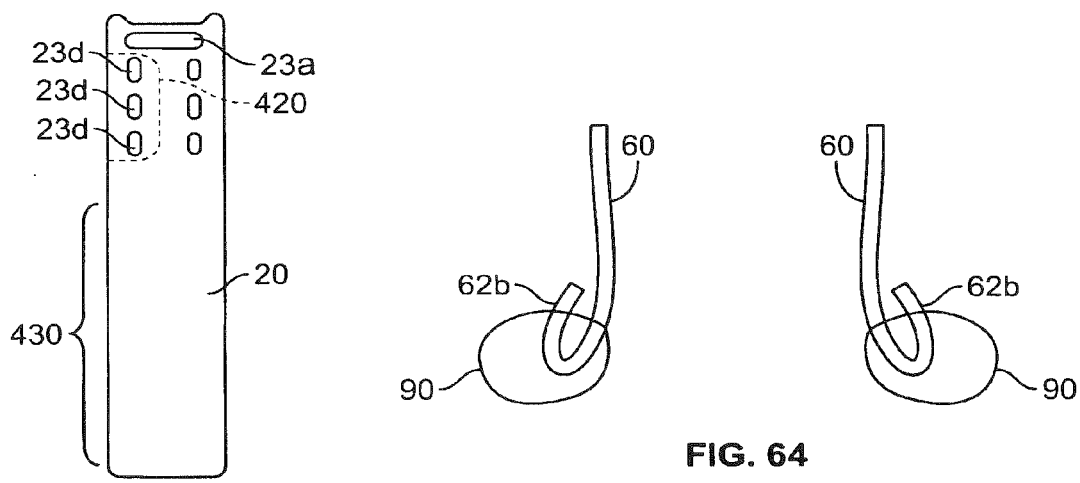
FIG. 64
FIG. 63

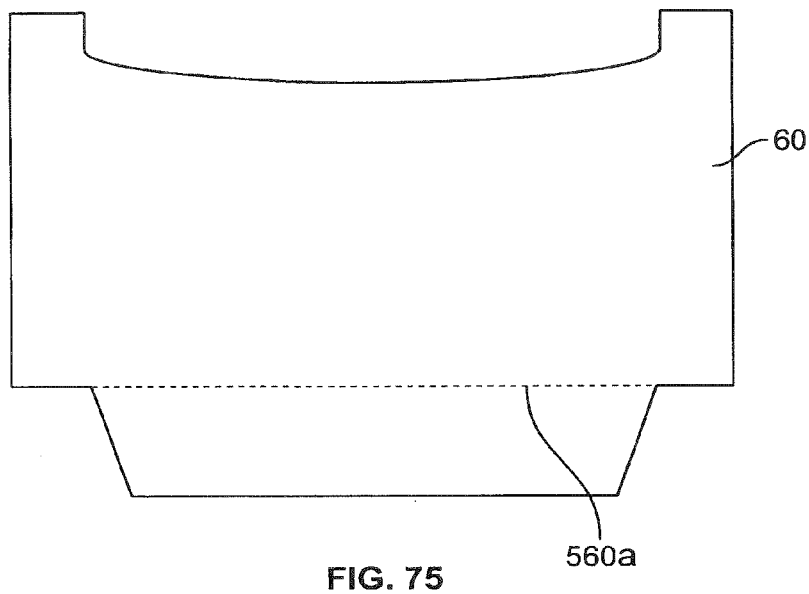
FIG. 75
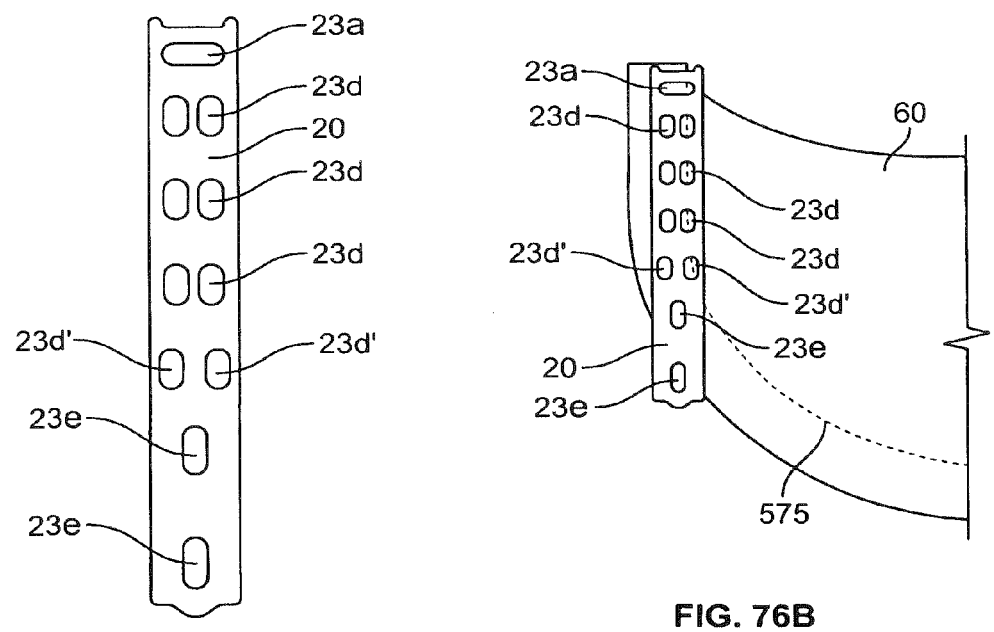
FIG. 76A
FIG. 76B

COLLAPSIBLE PROSTHETIC HEART VALVES

CROSS-REFERENCES TO RELATED APPLICATIONS

The present application is a continuation of U.S. patent application Ser. No. 13,848,466, filed Mar. 21, 2013, which is a continuation of Ser. No. 12/733,759, filed Mar. 18, 2010, now U.S. Pat. No. 8,425,593, which is a national phase entry under 35 U.S.C. §371 of International Application No. PCT/US2008/011153 filed Sep. 26, 2008, published in English, which claims the benefit of U.S. Provisional Application No. 60/995,648 filed Sep. 26, 2007, all of which are hereby incorporated herein by reference.

BACKGROUND OF THE INVENTION

Current collapsible prosthetic heart valve designs are for use within patients who may need a valve replacement (e.g., an aortic valve replacement), but who are not treated adequately by other means. A collapsible prosthetic heart valve is designed to be delivered into the patient in a collapsed condition via tube-like delivery apparatus. In the collapsed condition the valve has a reduced annular, radial, or circumferential size. Delivery of the valve into the patient can be less invasive than traditional open-chest/open-heart surgery. When the valve reaches the intended implant site in the patient, the valve re-expands or is expanded (e.g., balloon expanded) to operating size. The collapsing and re-expansion of the valve are preferably elastic, but may alternatively be plastic, the result of shape-memory properties of certain components of the valve, or various combinations of elastic, plastic, and/or shape-memory. Again, plastic expansion may be as a result of inflation of a balloon that is temporarily disposed inside the valve. Known designs of this general kind can be implanted percutaneously, trans-apically, or surgically, with or without resected and/or debrided native heart valve leaflets.

SUMMARY OF THE INVENTION

The prosthetic heart valves disclosed herein incorporate a collapsible valve (which may or may not include independently flexing commissure posts) and unique ways in which to assemble the leaflets and ancillary components.

In accordance with certain possible aspects of the invention, a prosthetic heart valve may include an annular, annularly collapsible and re-expandable supporting structure, and a sheet-like, flexible, leaflet member mounted inside the supporting structure so that a free edge portion of the leaflet forms a flexible chord across an interior of the supporting structure. Material of the leaflet may extend beyond an end of the chord and form a flap that is folded to lie, at least in part, in a cylindrical surface defined by one of the inner and outer surfaces of the supporting structure.

The above-mentioned flap may be secured to the supporting structure. For example, the flap may be sutured to the supporting structure to secure the flap to the supporting structure. As a more particular example, the flap may lie, at least in part, in the cylindrical surface defined by the inner surface of the supporting structure. Alternatively, the flap may pass through the supporting structure to lie, at least in part, in the cylindrical surface defined by the outer surface of the supporting structure.

The leaflet may have a secured line portion which is spaced from the free edge portion across an intervening belly portion of the leaflet. The secured line portion may be secured to the supporting structure, and additional material of the leaflet beyond the secured line portion away from the belly portion may form a second flap that is folded to lie, at least in part, in a cylindrical surface defined by one of the inner and outer surfaces of the supporting structure.

The above-mentioned second flap may be folded toward the free edge portion of the leaflet and secured to the supporting structure inside the supporting structure. Alternatively, the second flap may be folded away the free edge portion and secured to the supporting structure inside the supporting structure. Especially in the latter case, the second flap may continue beyond an axial end of the supporting structure and may be additionally folded over that axial end and back outside of the supporting structure for additional securement to the outside of the supporting structure.

A prosthetic heart valve in accordance with the invention may additionally include sheet-like, flexible, buffer material between the supporting structure and the leaflet. Buffer material can alternatively be provided so that it only outlines (covers) certain members of the supporting structure, instead of forming a more extensive continuous sheet that covers not only members of the supporting structure but also otherwise open cells of that structure. For example, such outlining or less extensive buffer material can be a dip-coated or sprayed-on polymer.

The supporting structure of a prosthetic heart valve in accordance with the invention may include a plurality of annularly spaced commissure posts, each of which may be cantilevered from other structure of the supporting structure. The above-mentioned flap that extends beyond an end of the above-mentioned free edge chord of the leaflet may be secured to an associated one of the commissure posts. For example, this securement may be by suture material that passes through the flap and apertures through the associated commissure post. The flap may be folded around the associated commissure post. The associated commissure post may be bifurcated into two spaced apart members. The flap may pass through the commissure post between those two members.

In accordance with another possible aspect of the invention, the supporting structure may include a plurality of annular, annularly collapsible and re-expandable substructures that are spaced from one another along an axis about which the supporting structure is annular. The supporting structure may further include a plurality of linking members that are substantially parallel to the above-mentioned axis and that interconnect the substructures without the linking members deforming when the substructures annularly collapse and re-expand.

In accordance with yet another possible aspect of the invention, a leaflet structure for a prosthetic heart valve may include a sheet of flexible leaflet material having a central opening with three sides, each of the sides being shaped to form the free edge of a respective one of three operating leaflet portions of the leaflet structure. The sheet may additionally have three secured line portions, each of which is radially outward from a respective, associated one of the free edges, and each of which is arcuate so that it is radially farther from a midpoint of the associated free edge than from endpoints of the associated free edge.

The above-mentioned sheet may define three leaflet-linking areas, each of which extends from a junction of a respective pair of the free edges to a junction of the secured line portions that are radially outward from the free edges in that pair.

For use of the above-mentioned sheet, a prosthetic heart valve in accordance with the invention may include an annular, annularly collapsible and re-expandable supporting structure. The above-mentioned sheet may then be disposed in the supporting structure with the secured line portions and the leaflet-linking areas secured to the supporting structure so that the free edges can come together in the interior of the supporting structure. The supporting structure may include three annularly spaced commissure posts, each of which may or may not be cantilevered from other structure of the supporting structure. Each of the leaflet-linking areas may be secured to a respective one of the commissure posts. At least one of the leaflet-linking areas may pass outside the supporting structure at the commissure post to which that leaflet-linking area is secured. At least one of the commissure posts may be bifurcated into two spaced apart members, and the leaflet-linking area that is secured to that commissure post may pass between the two members of that commissure post.

The above-mentioned sheet may continue radially outwardly beyond at least a portion of at least one of the secured line portions to form a flap. In use of the sheet in a prosthetic heart valve that includes a supporting structure as mentioned above, such a flap may be secured to the supporting structure. For example, the flap may be secured inside the supporting structure. Alternatively, the flap may be secured outside the supporting structure.

As another possibility, in use of the above-mentioned sheet in a prosthetic heart valve that includes a supporting structure (as also mentioned above), the valve may also include sheet-like, flexible, buffer material between the supporting structure and the leaflet material.

In accordance with other possible aspects of the invention, a prosthetic heart valve may include an annular, annularly collapsible and re-expandable supporting structure, which in turn includes a plurality of members disposed in a zig-zag pattern that extends in a direction that is annular of the supporting structure. At least two of the members forming such a zig-zag pattern meet at an apex that points away from the supporting structure parallel to an axis about which the supporting structure is annular. The valve may further include a sheet of flexible material secured to the supporting structure, and a plurality of flexible leaflets disposed inside the supporting structure and at least partly secured to the sheet. The sheet may be at least partly secured to the supporting structure via a suture attachment at the apex. The apex may be shaped to prevent the suture attachment from moving away from the apex in a direction opposite to a direction in which the apex points.

As a specific example, the above-mentioned apex may include an eyelet through which the suture attachment passes. As another example, the apex may include an enlarged head on the end of a reduced neck that extends in the direction that the apex points, and a suture attachment for the above-mentioned sheet may be wound around the neck. As still another example, the apex may comprise a notch that opens in the direction that the apex points, and the above-mentioned suture attachment may be wound around the inside of the apex and the inside of the notch. The above-mentioned notch may be narrowed near its entrance to form an open eyelet. Such an open eyelet may be too small for passage of a suture needle, but the entrance may be large enough for suture material to slip through.

Further features of the invention, its nature and various advantages, will be more apparent from the accompanying drawings and the following detailed description.

BRIEF DESCRIPTION OF THE DRAWINGS

FIG. 2A shows only the foreground portion of the depicted component.

FIG. 62 is similar to FIG. 44 for another illustrative embodiment.

FIG. 63 is similar to a portion of FIG. 53B for another illustrative embodiment.

FIG. 64 is a simplified, partial, sectional view of an illustrative embodiment of an assembly of several components in accordance with the invention.

FIG. 75 is similar to FIG. 62 for another illustrative embodiment.

FIG. 76A is similar to FIG. 63 for another illustrative embodiment.

FIG. 76B is similar to FIG. 76A with another illustrative component shown.

DETAILED DESCRIPTION

As just one example of a context in which the present invention may be employed, thousands of high-risk patients with severe aortic stenosis go untreated each year because they are deemed inoperable for a heart valve replacement. In an attempt to treat these patients, collapsible prosthetic valves have been developed to be inserted within the stenotic leaflets of these patients via percutaneous and/or trans-apical means. However, known designs may not sufficiently address several aspects of an optimal valve design, such as: (1) long-term durability, (2) mitral valve impingement, (3) perivalvular leakage, etc. Leaflet attachment can be a key element when considering some of these issues. The designs disclosed herein provide these high-risk patients with superior valves by better addressing these and other issues.

Figure 1A:
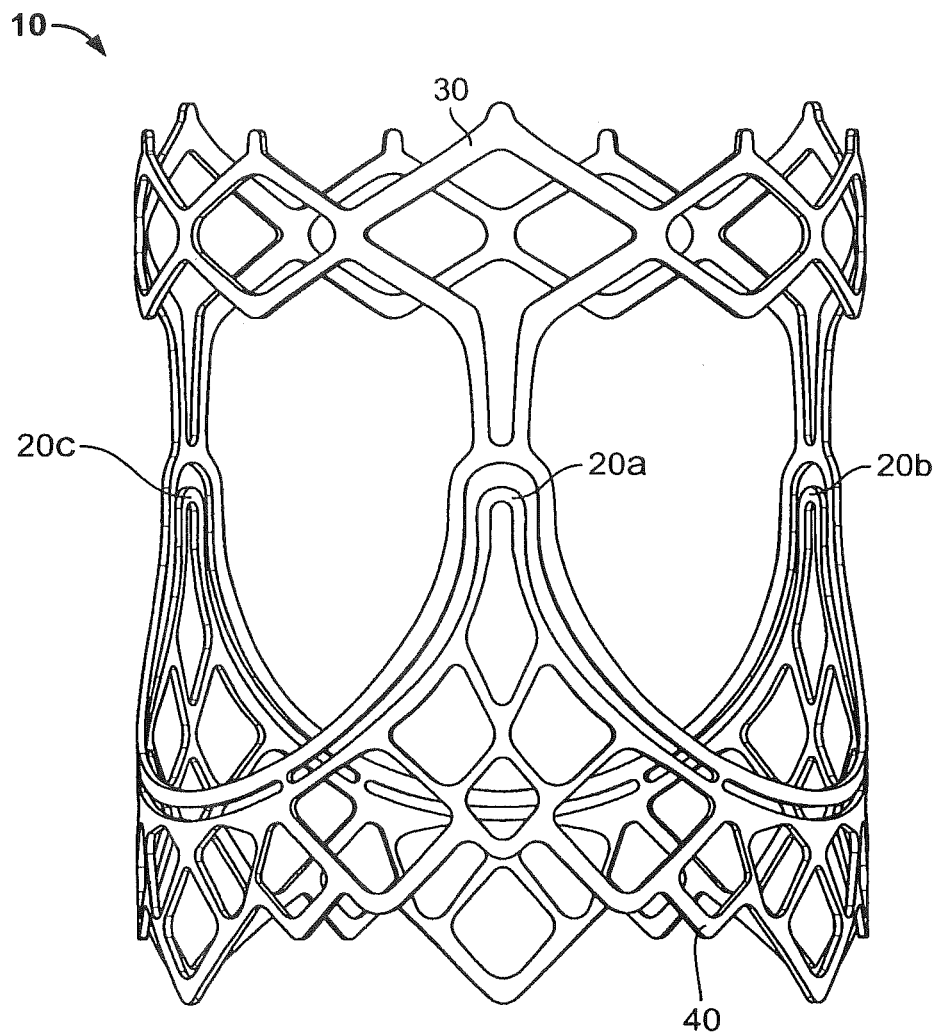
FIG. 1A is a simplified elevational view of an illustrative embodiment of a component that can be used in prosthetic heart valves in accordance with the invention.
Figure 1B:
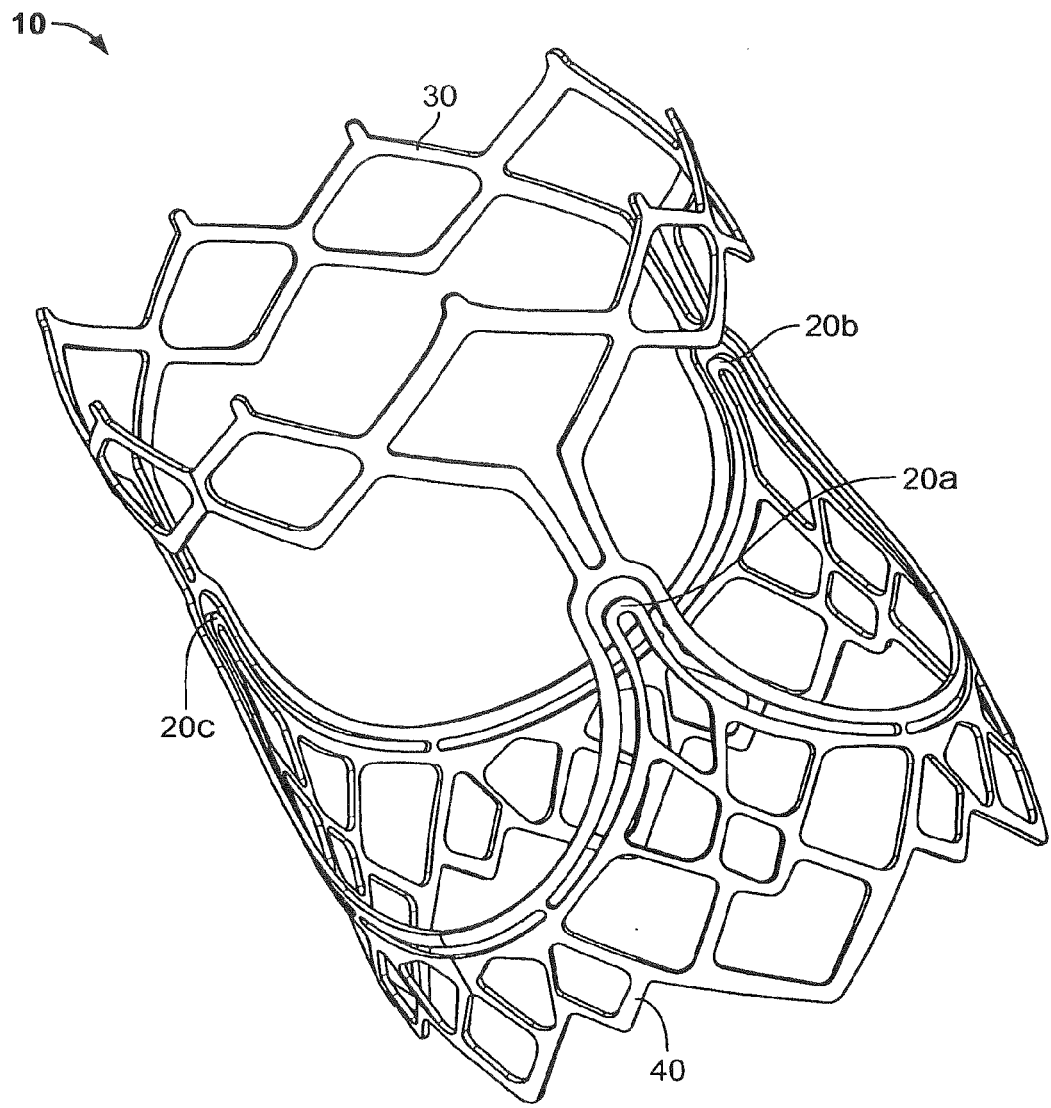
FIG. 1B is an isometric or perspective view of what is shown in FIG. 1A.

FIGS. 1A-B provide a general overview of an illustrative embodiment of a stent structure 10 that can be used in valves in accordance with this invention. These FIGS. show an expanded stent with independently flexing commissure posts 20a-c to reduce stress imparted to the valve leaflets (not shown). (Although this embodiment and several other embodiments have independently flexing commissure posts, still other embodiments are shown that also increase valve durability and that have only partially or not independently flexing commissure posts.) The independent posts are partly separate from the anchoring structure 30 downstream from the patient's valsalva sinus (upper portion of structure as viewed in FIGS. 1A-B) and 40 adjacent the patient's native aortic valve annulus (lower portion of structure as viewed in FIGS. 1A-B). In particular, upper free end portions of posts 20a-c are cantilevered from the annulus portion 40 of stent 10. (Again, however, other embodiments may have only partially cantilevered or non-cantilevered commissure posts.)

Figure 2A:
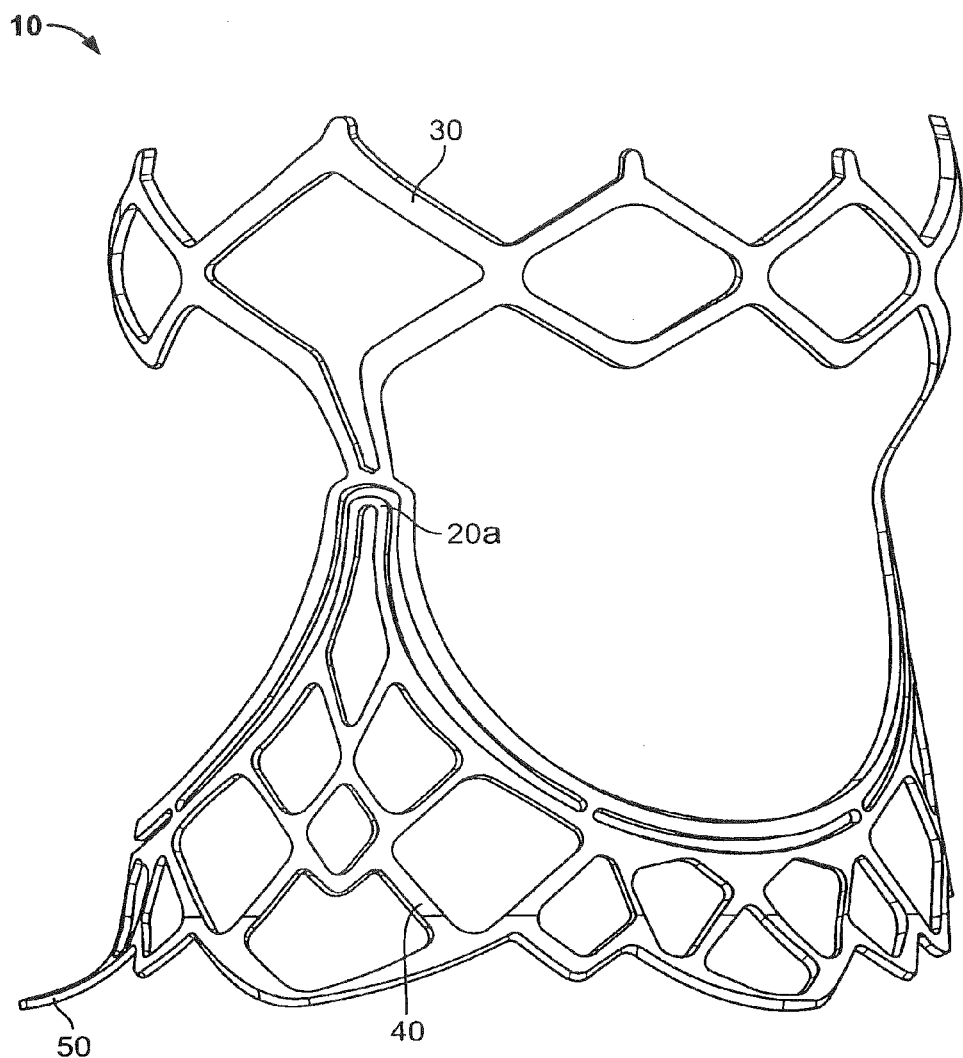
FIG. 2A is a simplified elevational view of an alternative embodiment of what is shown in FIG. 1A.
Figure 2B:
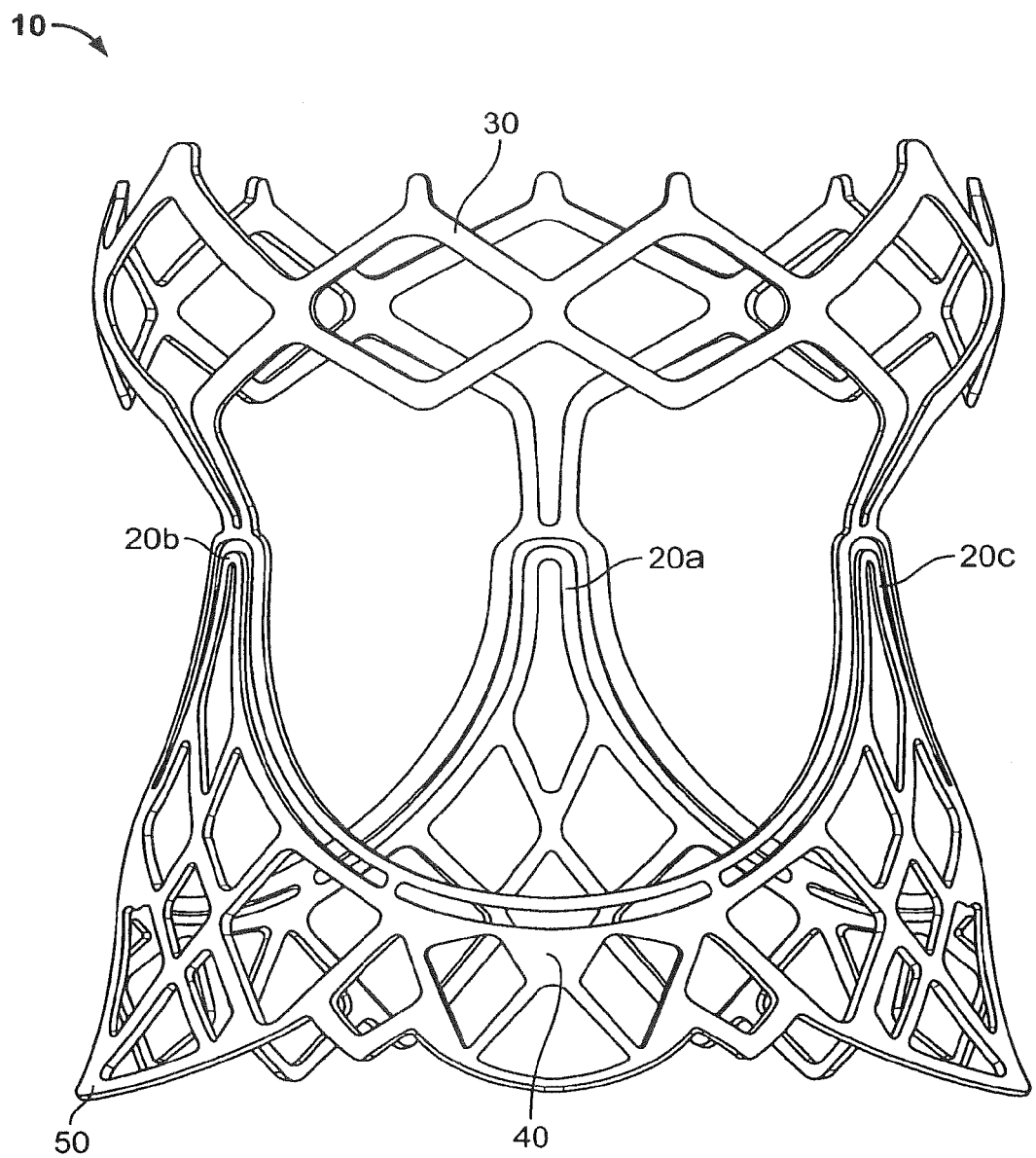
FIG. 2B is similar to FIG. 2A, but from a different angle and with parts of the background structure shown in addition to the foreground structure.

FIGS. 2A-B show an illustrative embodiment of an expanded and contoured stent 10 with skirt flare 50 on base 40 and an extra-expanded section 30 for the aorta. (Reference numbers are reused for generally similar features in different FIGS. and different embodiments. Some FIGS. do not show the rear or the complete rear of all structures to avoid over-complicating the depictions.) Attachment of leaflets (not shown) to posts 20a-c and covering of the stent are important aspects of this invention.

Figure 3A:
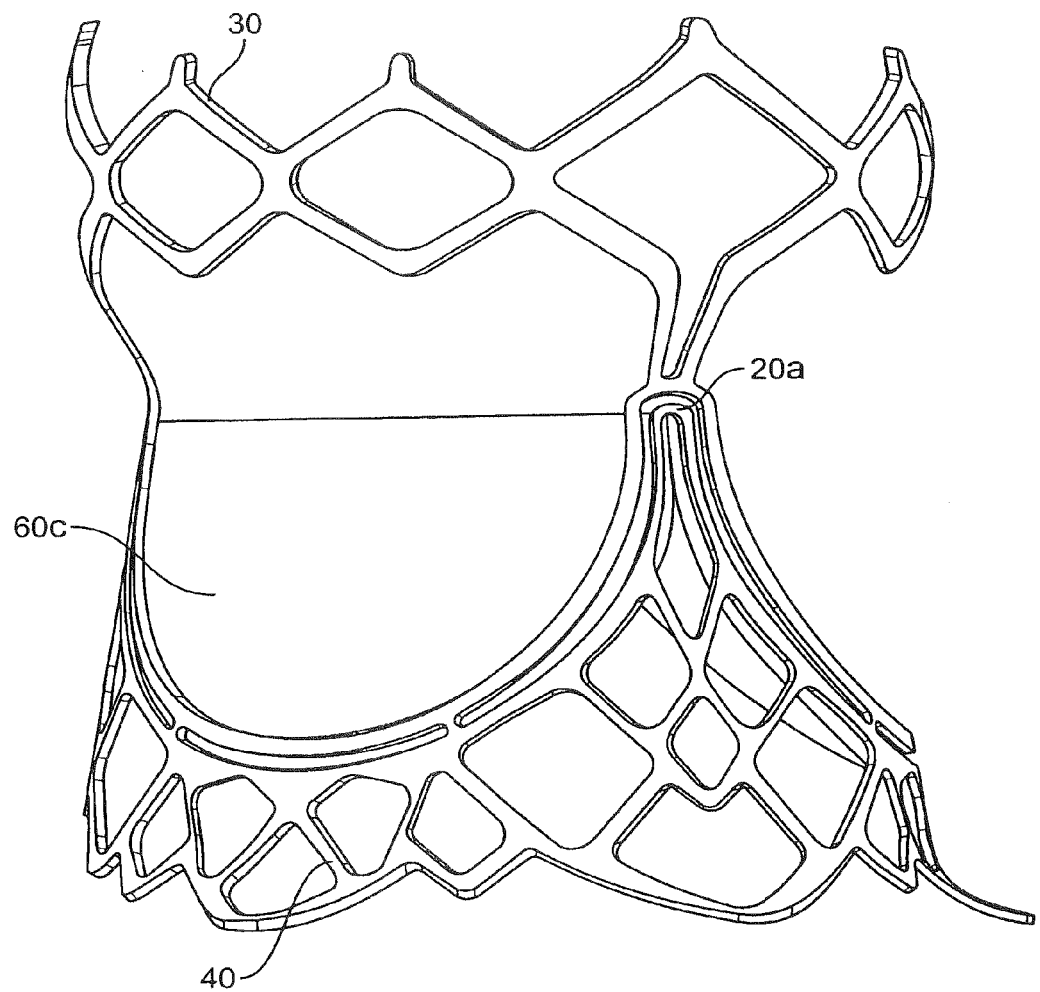
FIG. 3A is similar to FIG. 2A, but with illustrative additional components added.
Figure 3B:
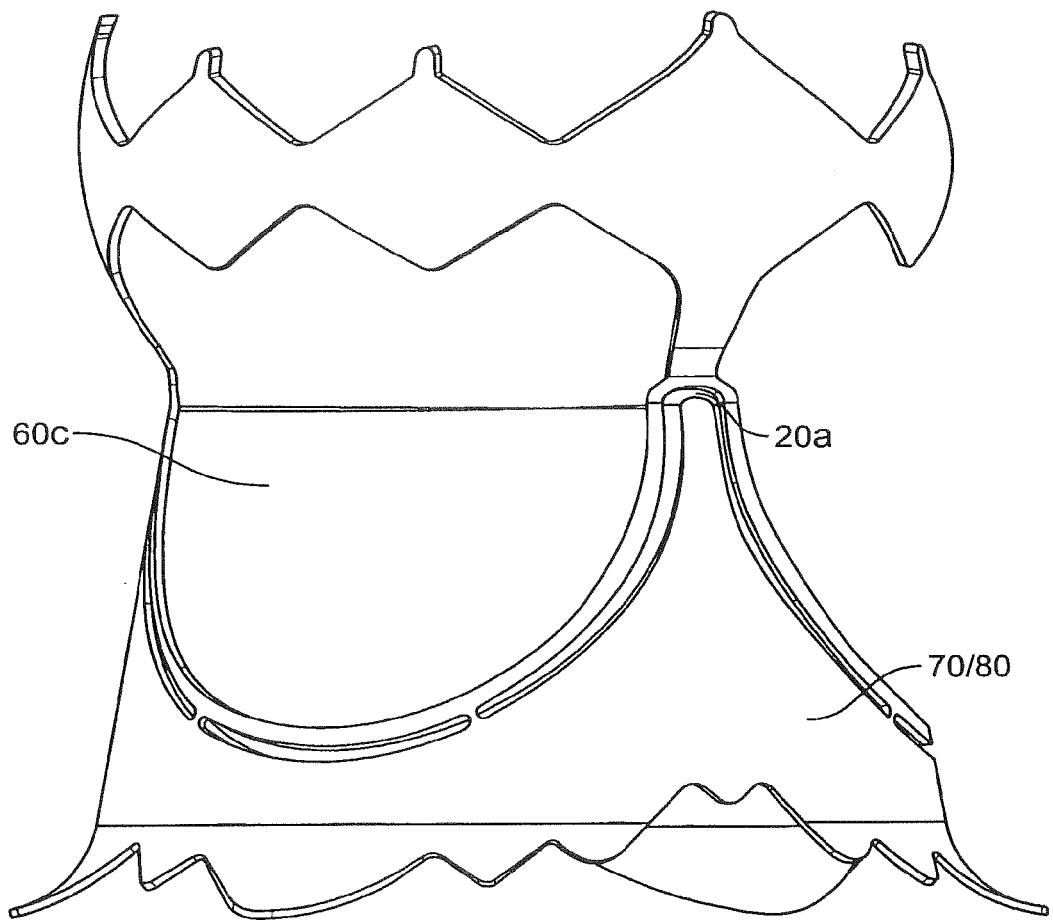
FIG. 3B is similar to FIG. 3A, but with illustrative, still further components added.

FIGS. 3A-B show an illustrative embodiment of an expanded and contoured stent 10 with valve leaflets 60a-c and buffer layer 70 and outer cuff material 80. Note that commissure posts 20 can lie perfectly vertically, or alternatively they can be angled inwardly to bias the leaflets inwardly and thereby help to keep them from hitting the prosthetic valve frame and/or the surrounding patient anatomy during opening.

Attachment steps (in any order) after a stent 10 is at a predetermined diameter and polished are generally the following:

Flexible leaflets 60a-c (e.g., polymer sheet or pericardial tissue sheet) are processed and cut to shape.
For example, tissue leaflets 60a-c can be laid flat and fixed with the use of glutaraldehyde or triglycidylamine before being treated with an anti-calcification treatment such as at least a 60% solution of ethanol.
Buffer material or materials 70 (e.g., polymer sheet or pericardial tissue sheet) are processed and cut to shape.
Cuff material 80 (e.g., polyester fabric sheet) is formed into a tube of the appropriate diameter and cut to length.
Cuff material 80 can cover the lower portion of stent 10, the entire portion of where the leaflets are attached, and/or the entire stent including an aorta section.
Intermediate materials of one or more layers (sheets) between stent 10 and leaflet material 60 may be applied for attachment, friction buffering, and tissue in-growth purposes. For example, an interface between two polymer or tissue layers may be beneficial, as compared to an unbuffered interface between leaflets 60 and stent 10, for the above-mentioned reasons (e.g., less friction on and therefore wear of leaflets 60). Lubricious polymer coating of the stent instead of just sheets may also be incorporated.
Leaflets 60 are attached to stent 10 and around the circumference of the stent base.
Specific details as to how the valve is assembled for different types of stent posts 20 are given below.

Figures 4A, 4B:
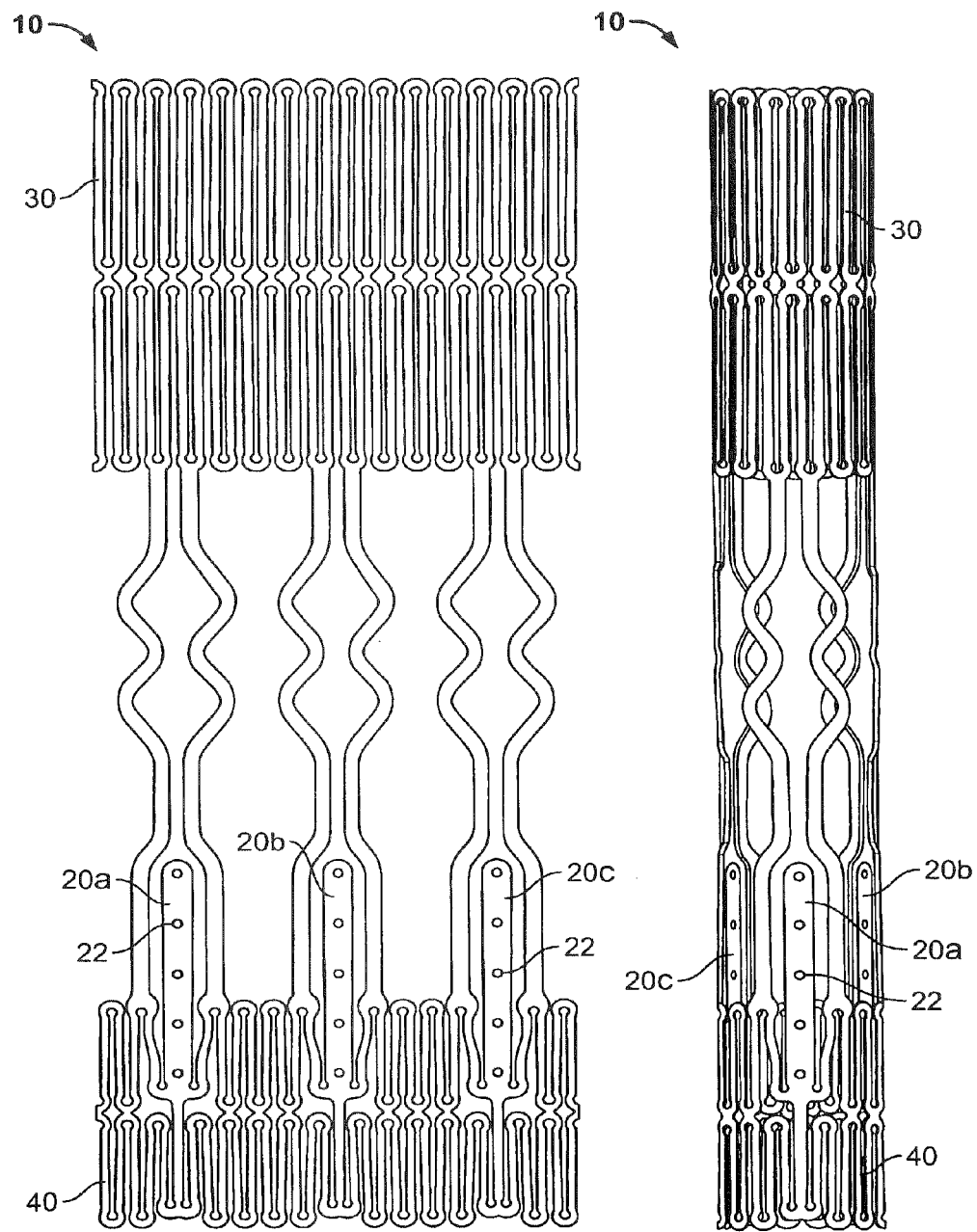
FIG. 4A is a flat development of an illustrative embodiment of what is actually a cylindrical component, which can be used in prosthetic heart valves in accordance with the invention.
FIG. 4B is an elevational view of the cylindrical component that is shown in flat-development form in FIG. 4A.

FIG. 4A shows the flat and collapsed state of a stent model used to laser-cut a part (stent) 10 from a tube (e.g., of a super-elastic metal such as nitinol or a balloon-expandable material such as cobalt chromium). FIG. 4B shows a round laser-cut part (stent) 10 in the collapsed state. This stent embodiment has independent flexing commissure posts 20a-c that are solid except for one set of eyelets 22. Note, however, that these eyelets can be converted to any orifice shape such as an elongated slot.

Figure 5A:
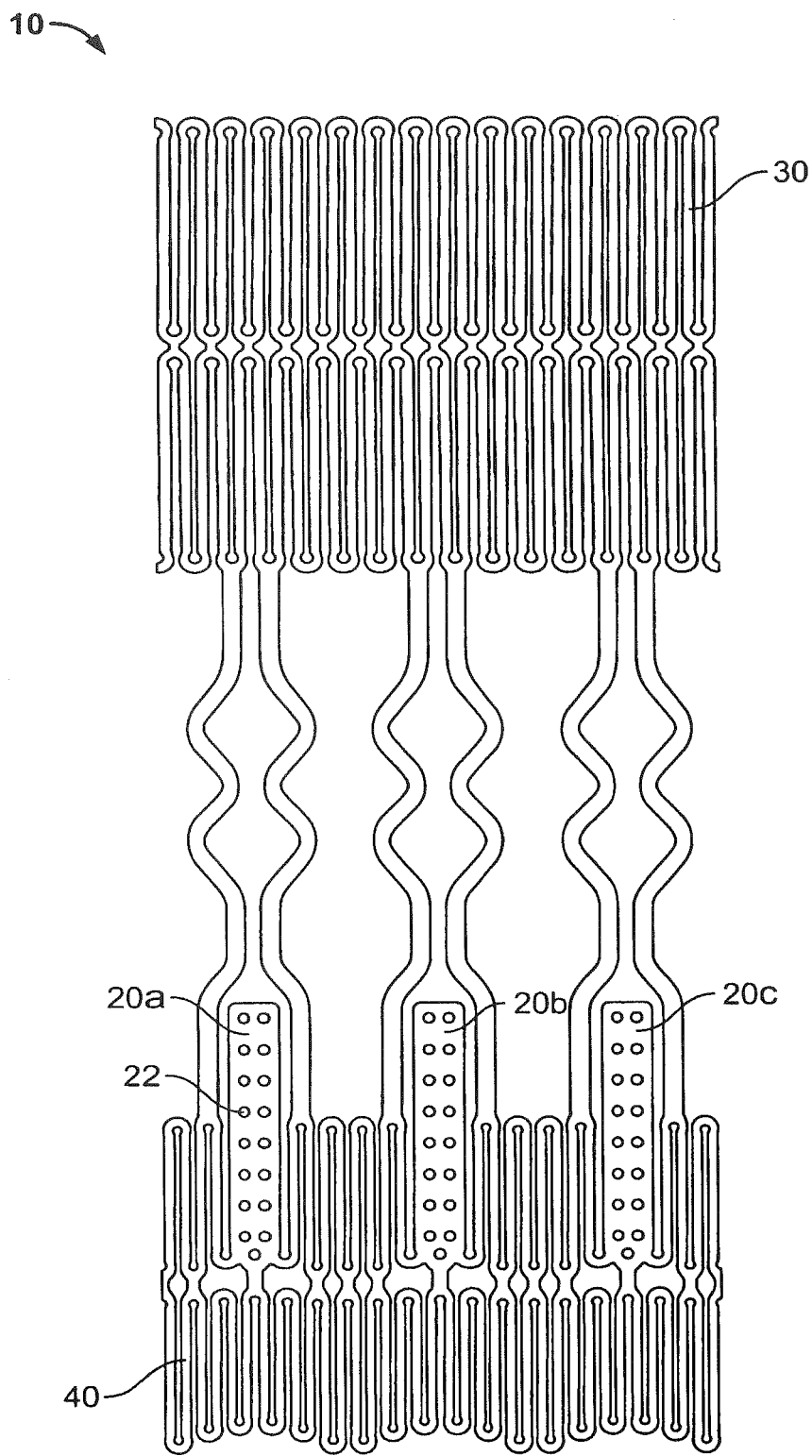
FIG. 5A is similar to FIG. 4A for another illustrative embodiment.
Figure 5B:
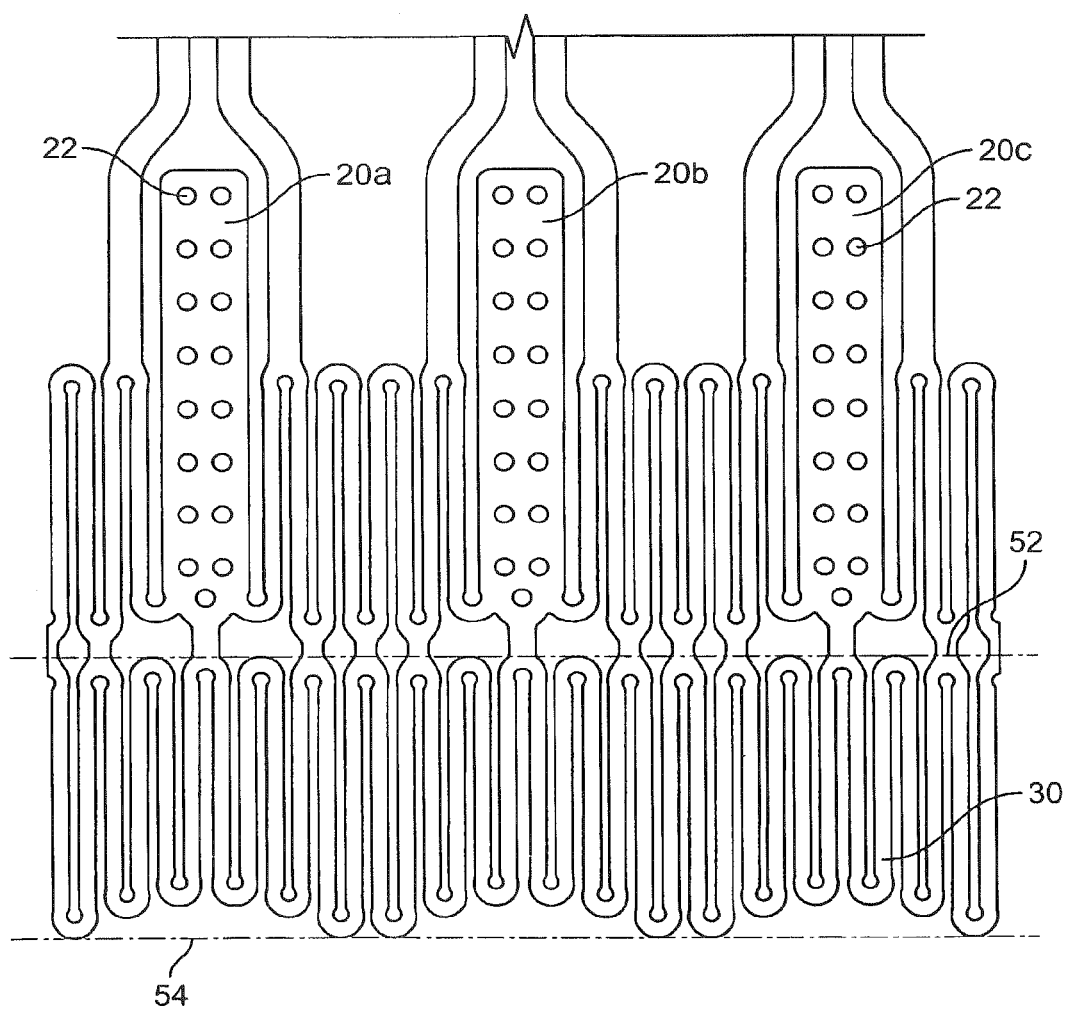
FIG. 5B is an enlargement of a portion of FIG. 5A.

FIGS. 5A-B show the flat and collapsed state of a stent model used to laser cut a part (stent) 10 from a tube and a close-up of the independent commissure posts 20a-c. This stent 10 has independent flexing posts 20a-c that are solid with two sets of eyelets 22. However, these eyelets could be converted to any orifice shape such as elongated slots. Note the bend line 52 of the skirt 50 and the base line 54 of the stent discussed in connection with later FIGS.

Figure 6:
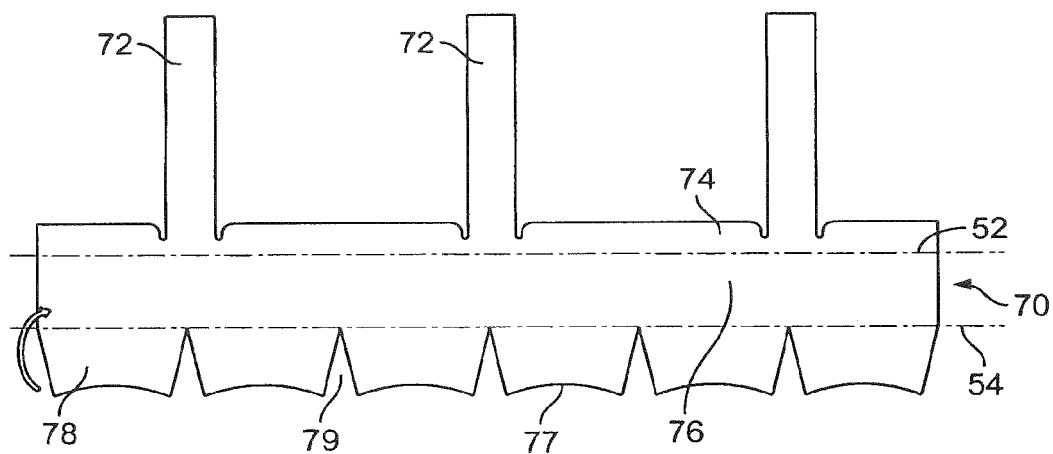
FIG. 6 is an elevational view of an illustrative embodiment of another component that can be used in prosthetic heart valves in accordance with the invention.

FIG. 6 shows a buffering layer 70 that outlines the inner surface of a stent 10 (actually stent portion 40) and posts 20a-c to ensure that there is no contact between the leaflets 60 and any other material. Each rectangular section 72 is sutured to the inner diameter of a respective one of posts 20. Top lip 74 covers the inner portion of the stent cells above bend line 52 (see also FIG. 5B). Bottom lip 76 covers the inner portion of the stent cells below bend line 52 to the bottom 54 of the stent (see also FIG. 5B). If section 78 is present, it can be wrapped around the bottom edge 54 of the stent from the inner diameter to the outer diameter to be terminated at the bottom stent edge or farther up. Note that the triangular cut-outs 79 in this section allow for flexible movement of the edge and actually will meet when wrapped around the bottom edge, while the rounded extreme bottom edge sections 77 will meet to form one continuous circular path around the stent. The triangular cut-outs 79 also allow for a minimized chance of tearing during expansion and contraction of the valve.

Figure 7:
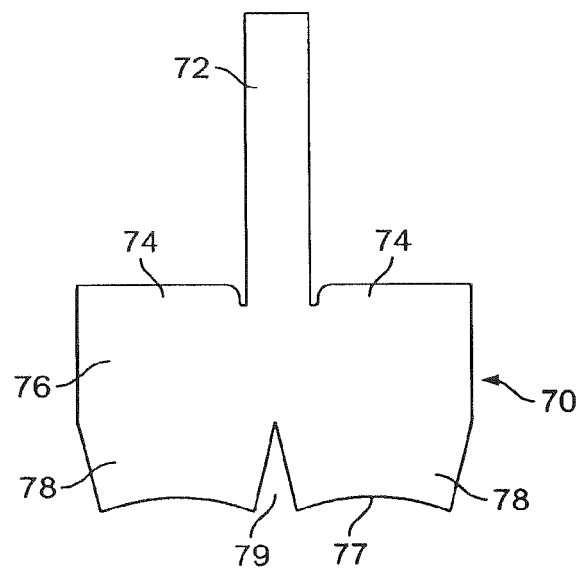
FIG. 7 is similar to FIG. 6 for another illustrative embodiment.

FIG. 7 shows that the buffering layer 70 of this and all presented designs in this invention disclosure can be made from three single sections as shown in this FIG. (in contrast to one single piece as shown in FIG. 6).

Figure 8:
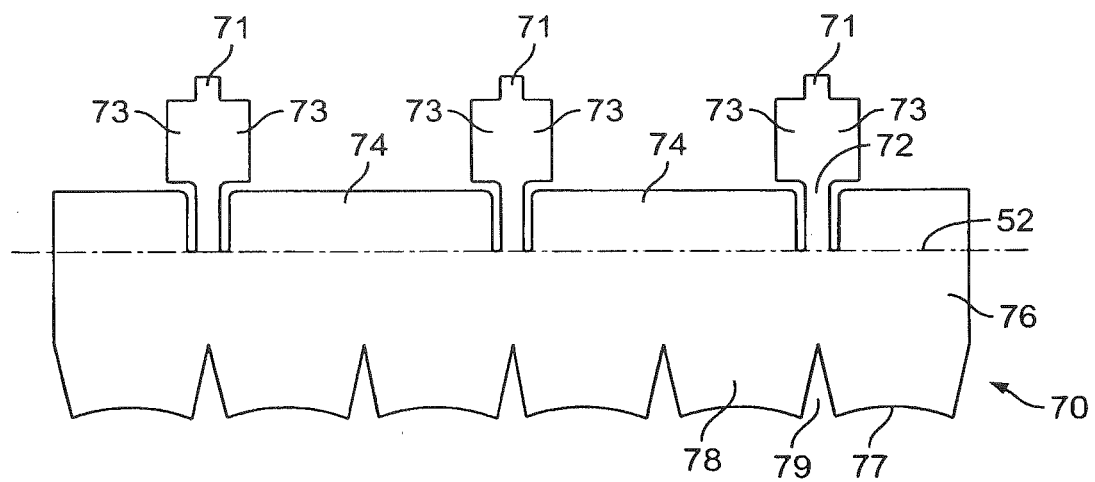
FIG. 8 is similar to FIG. 7 for still another illustrative embodiment.

FIG. 8 shows additional features that can be included in buffering designs in accordance with the invention. (See FIG. 6 for general features that apply to all buffering designs of the invention.) Top flaps 71 wrap around the tops of the posts 20 from the inner diameter (ID) to the outer diameter (OD). Side flaps 73 wrap around the left and rights sides of each post 20 from the ID to the OD and are secured by sutures.

Figure 9:
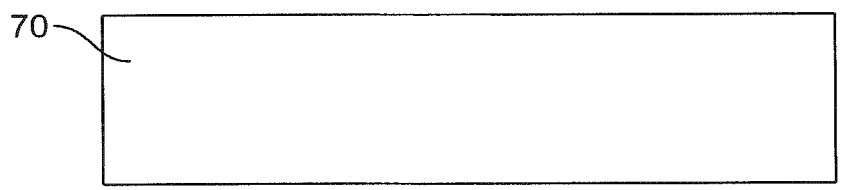
FIG. 9 is similar to FIG. 8 for yet another illustrative embodiment.

FIG. 9 shows that in areas of high complexity, individual buffering strips 70 of various sizes and shapes can be wrapped about the stent frame and sutured in place. FIG. 9 shows a generic rectangular strip 70 as an example. A rectangular strip can be rolled to form a cylinder of a desired height to cover any portion of the stent as well.

Figure 10:
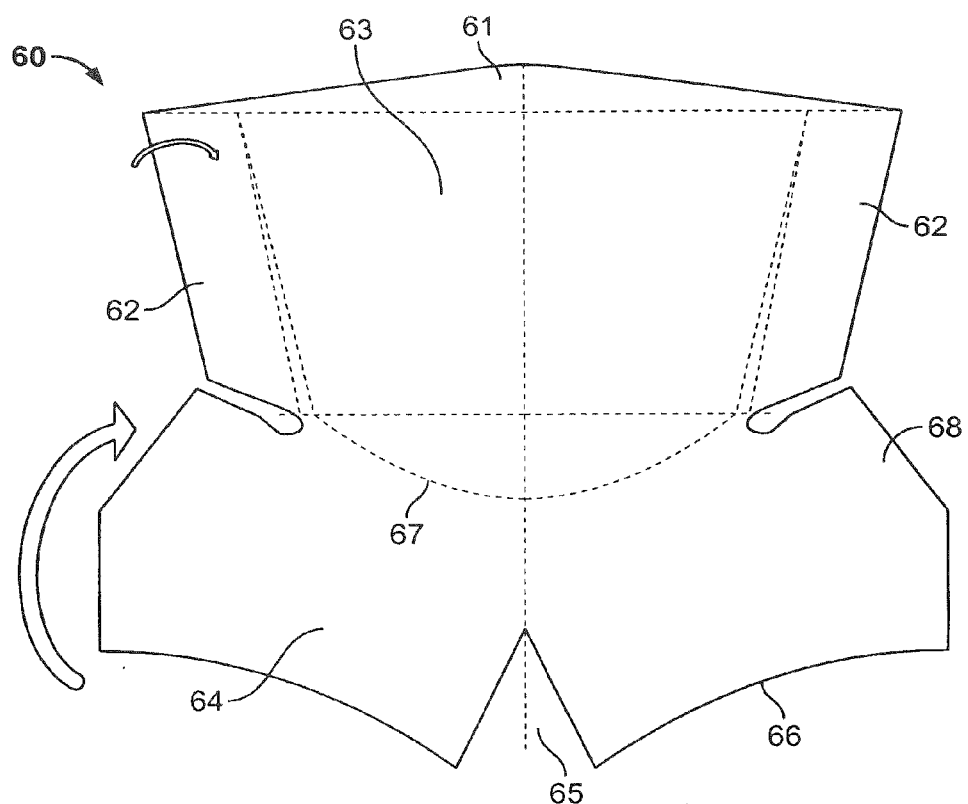
FIG. 10 is an elevational view of an illustrative embodiment of still another component that can be used in prosthetic heart valves in accordance with the invention.

FIG. 10 shows a single leaflet design 60 that is the foundation for many of the following leaflet designs in this disclosure. Material 61 above the top-most horizontal dotted line is for redundant coaptation where all three leaflets 60a-c meet under back-pressure. (The various dotted lines are shown primarily for reference, although they can also actually appear on the leaflet (either temporarily or permanently) as a visual guide or aid for use during assembly of a valve.) Side flaps 62 bend at the angled lines and provide an area to suture to the commissure post 20 ID. Note that since the leaflet may be cut from a flat sheet, there may not be a belly-shaped contour in the leaflet body 63; but when the angled side flaps 62 are attached to a vertical post 20, this allows for the top portion of the leaflet to be closer to the central axis of the stent than the bottom portion, thus creating central coaptation. Side flaps 62 wrap around the left and right sides of the commissure posts 20 from the ID to the OD and are sutured down. Bottom flap 64 covers the ID portion of the stent cells below the bend line 52 to the bottom 54 of the stent. If this section is present, it can be wrapped around the bottom edge 54 of the stent from the inner diameter to the outer diameter to be terminated at the bottom stent edge or farther up, depending on its length. Note that the triangular cut-out 65 in this section allows for flexible movement of the edge and actually will meet when wrapped, while the rounded lower edge sections 66 will meet to form one continuous circular path around the stent. If desired, the material along curve 67 can be sutured down to form a natural belly shape for the leaflet. The bottom side flap 68 allows for some overlapping of adjacent leaflets to ensure that the inflow skirt edge is fully sealed. Triangular cut-outs 65 also allow for a minimized chance of tearing during expansion and contraction of the valve.

Figure 11:
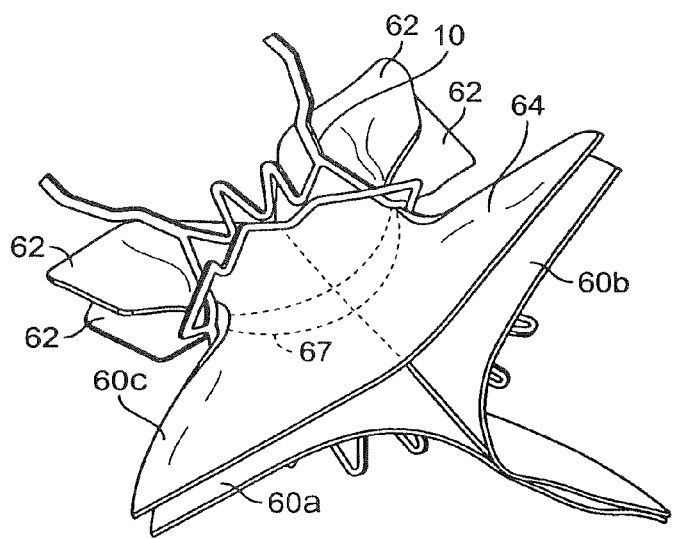
FIG. 11 is a simplified perspective view of an illustrative embodiment of an assembly of several components in accordance with the invention.

FIG. 11 shows three single leaflets 60*a-c* being attached to stent 10. The bottom flaps 64 and side flaps 62 can easily be seen before attachment occurs.

Figure 12C:
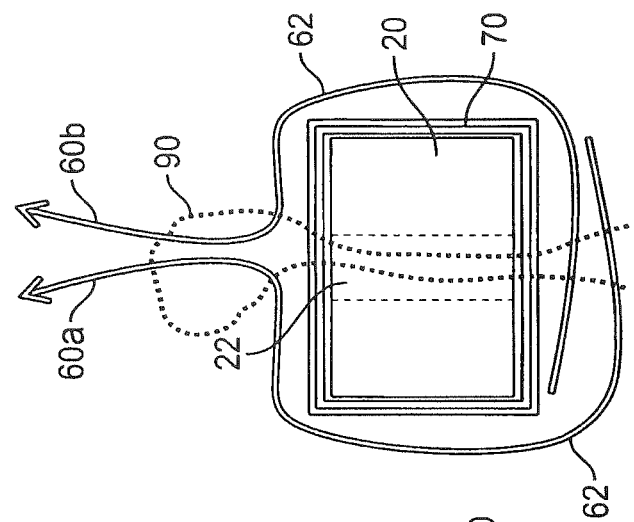
FIG. 12C is similar to FIG. 12B for still another illustrative embodiment.
Figure 12B:
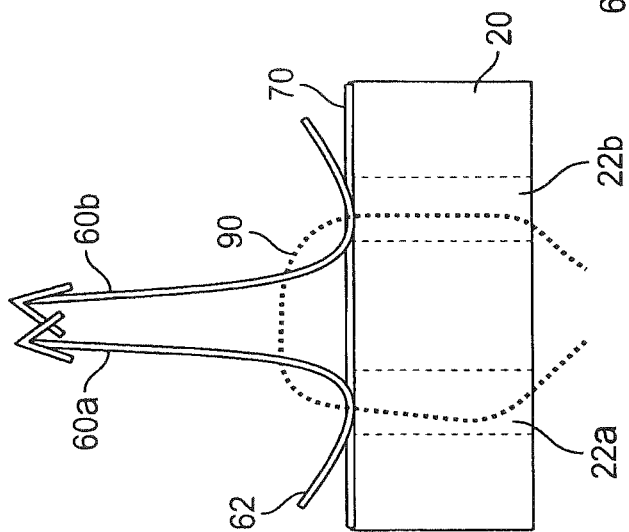
FIG. 12B is similar to FIG. 12A for another illustrative embodiment.
Figure 12A:
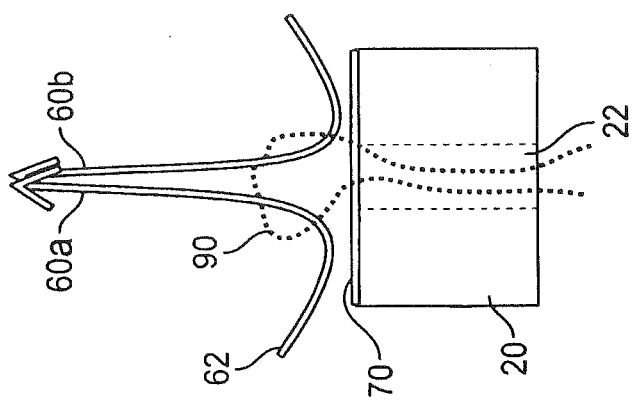
FIG. 12A is a simplified, partial, top view of an illustrative embodiment of an assembly of several components in accordance with the invention.

FIGS. 12A-C show three illustrative methods for leaflet and ancillary component assembly. Each of these FIGS. shows a top view of a commissure post 20 on the stent. (The commissure post is the large rectangle 20 in each of these FIGS.) In FIGS. 12A and 12C the commissure post has a single set of orifices 22. In FIG. 12B the commissure post has two sets of orifices 22*a* and 22*b*. In FIGS. 12A and 12B a buffering layer 70 is only on the ID surface of the post (which is the upper surface as viewed in these FIGS.). In FIG. 12C buffering layer 70 is wrapped all the way around the post. Lines 60*a* and 60*b* illustrate representative leaflets, and the arrows at the top ends indicate that the leaflet material continues beyond what is seen in the FIG. toward the central axis of the valve. The dotted lines 90 indicate a suture passing through the eyelet(s) 22 and through the leaflets 60. Major features to note are as follows: (1) a buffering layer 70 between the stent 10 and the leaflets 60 reduces abrasion, (2) leaflets 60 are sutured together to minimize any post gapping, (3) suture knots are on the OD of the post so as not to interfere with leaflet movement/abrasion, and (4) free ends 62 of the leaflets are curled back (e.g., toward the center of the valve) to provide an additional buffering layer. Note that in FIG. 12C the leaflets can only be wrapped around the post from the ID to the OD (as at 62) if there is enough room between stent cells when the valve is collapsed.

Figure 13:
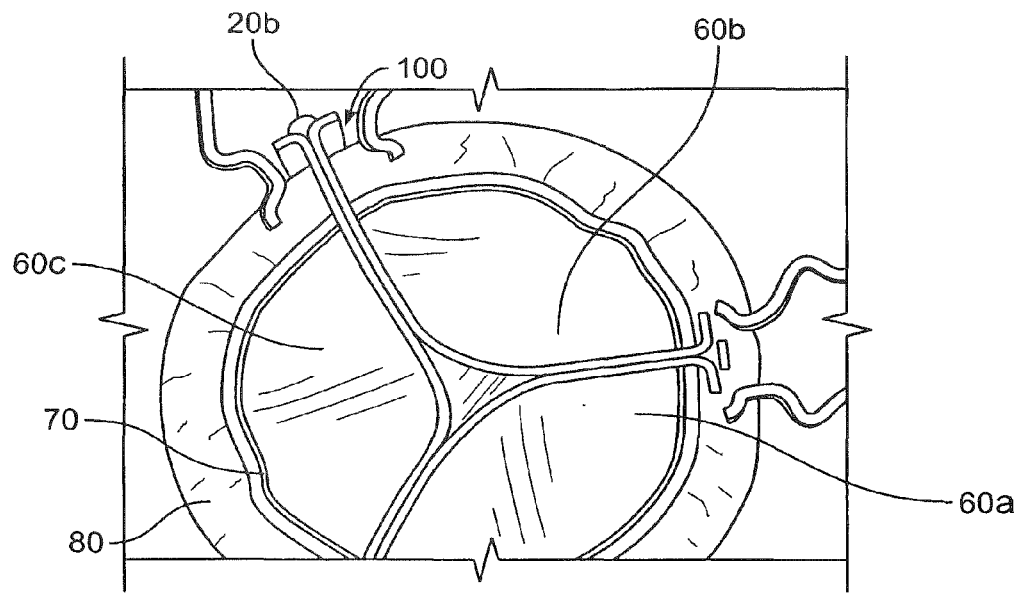
FIGS. 13 and 14 are each generally similar to FIG. 11.

FIG. 13 shows that on the fabric covering 80 on the ID of the stent there is a thin buffering material 70 to protect the leaflets 60 from abrading against the other valve surfaces. The lack of post gapping and the curled back leaflet edge before it is trimmed can be seen here at 100 (see also FIG. 12A).

Figure 14:
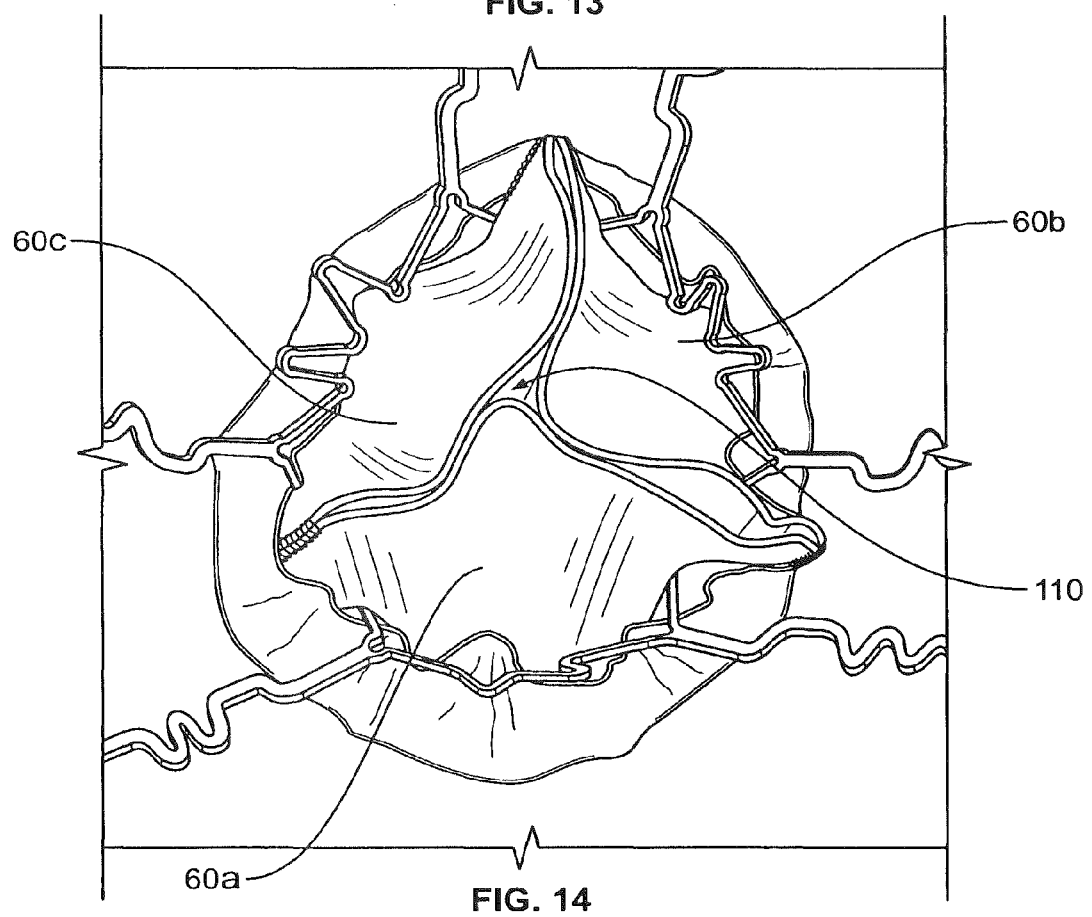

FIG. 14 shows how angled side flaps (62 of FIG. 10) allow leaflets 60*a-c* to coapt along the central axis 110. Note that under blood flow back-pressure, the leaflets will close tightly together with redundant coaptation.

Figure 15A:
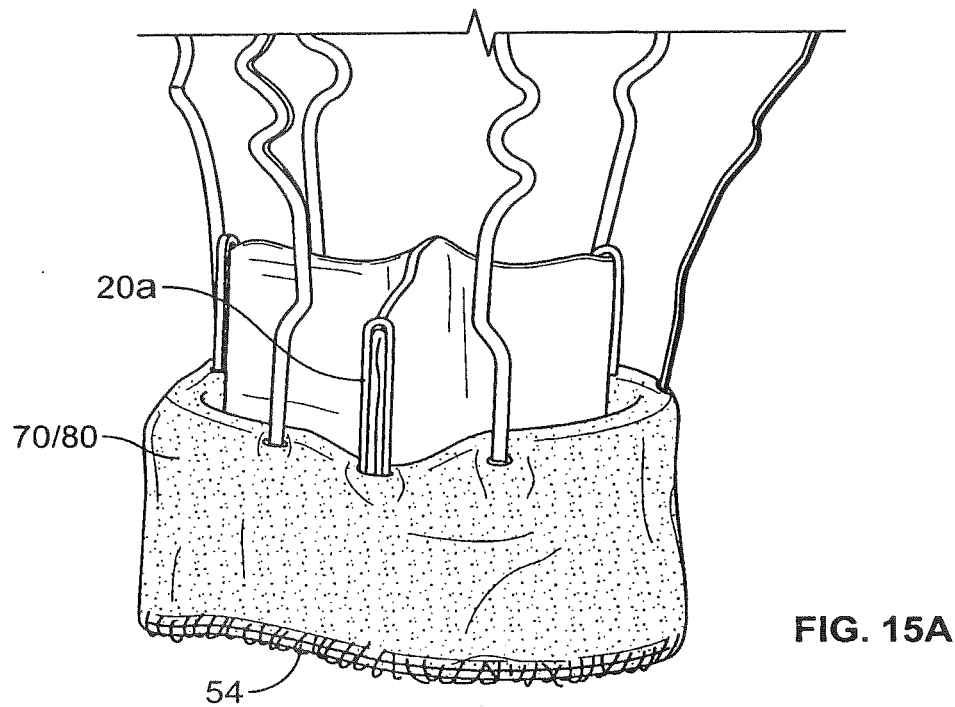
FIG. 15A is a simplified, partial, elevational view of an illustrative embodiment of an assembly of several components in accordance with the invention.
Figure 15B:
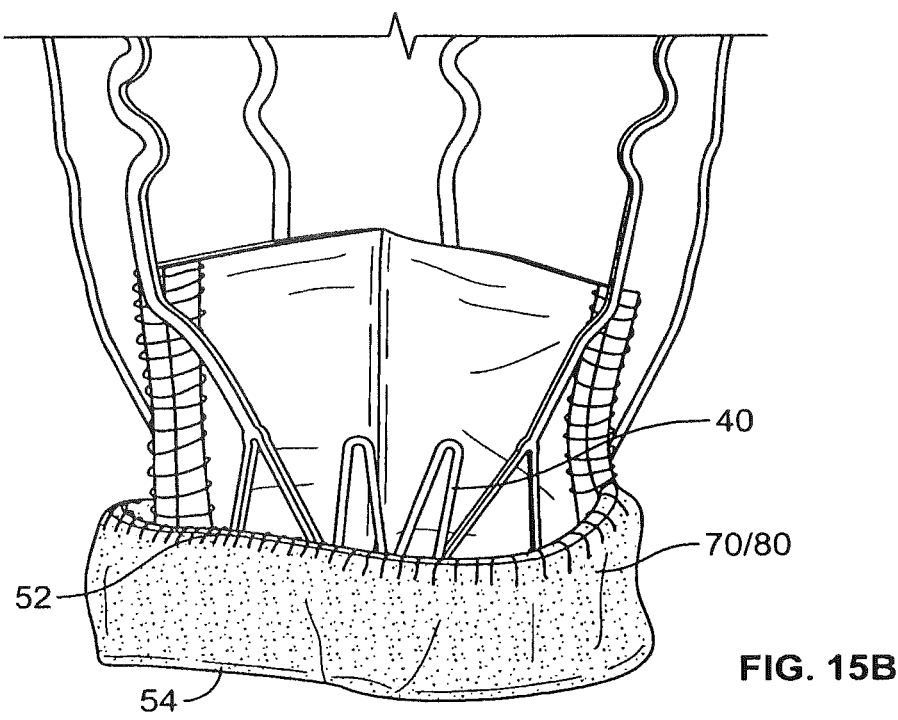
FIG. 15B is another view of the same general kind as FIG. 15A.

FIGS. 15A-B show two different valve variations that have a few key differences. FIG. 15A has a cuff and buffer section 70/80 that covers all of the expanding cells of stent portion 40. In FIG. 15B structure 70/80 goes half of the way up the stent cells 40 to approximately the bend line 52, which may leave metal exposed for leaflet contact during opening. FIG. 15A has a buffering layer and leaflets that terminate at the lower edge 54 of the stent, whereas the buffering layer and leaflets of FIG. 15B completely wrap over the bottom edge 54 and are anchored near bend line 52. Any or all of these features can be combined.

Figure 16:
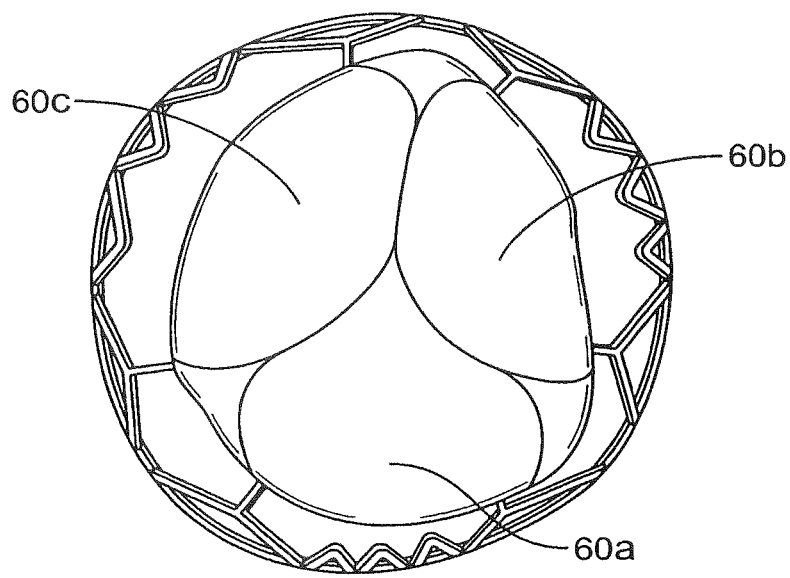
FIG. 16 is a bottom view of an illustrative embodiment of an assembly of several components in accordance with the invention.

FIG. 16 shows that there is a complete seal from the leaflets 60 and buffering layer all of the way from the stent ID around the edge of the stent base skirt to allow for a complete seal.

Figure 17:
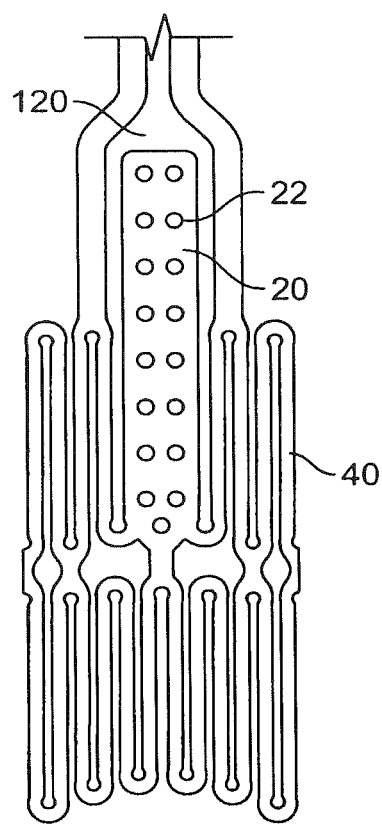
FIG. 17 is similar to FIG. 5B for another illustrative embodiment.

FIG. 17 shows that to allow for more transfer of leaflet load to the stent posts 20 (as opposed to almost entirely through point loads from the sutures 90 on the stent ID), sutures and/or leaflet material may need to be passed over the top of the post 20 and secured to the OD as indicated at 120.

Figure 18A:
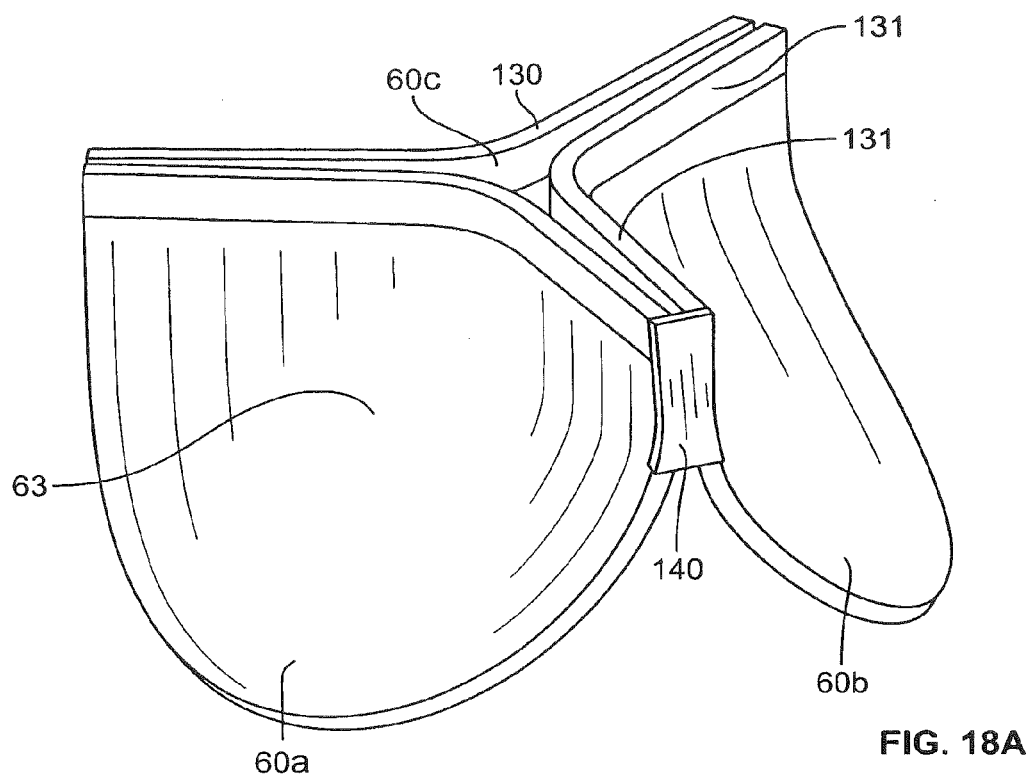
FIG. 18A is a simplified isometric or perspective view of an illustrative embodiment of an assembly of several components in accordance with the invention.
Figure 18B:
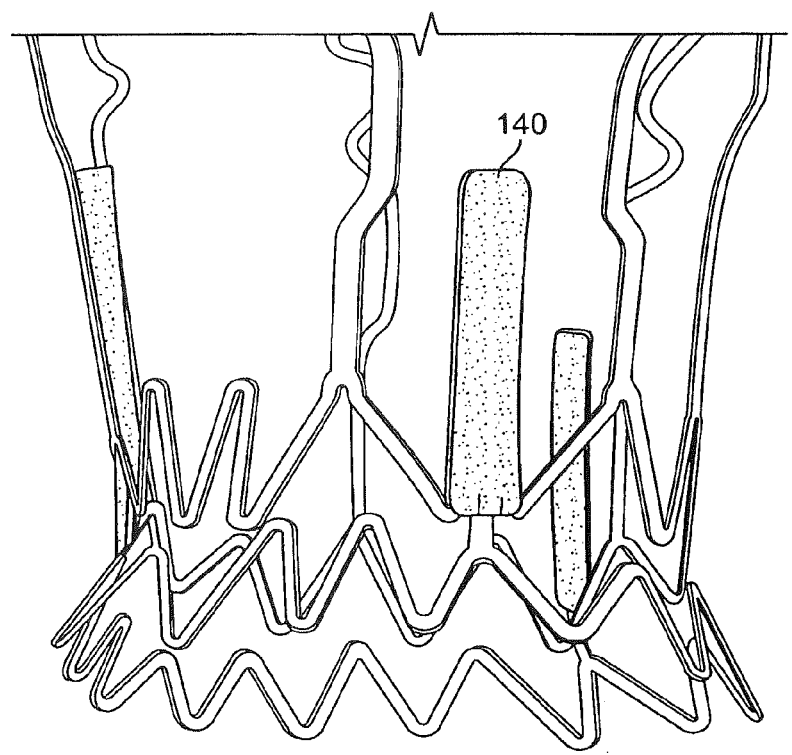
FIG. 18B is a simplified, partial, elevational view of an illustrative embodiment of several components in accordance with the invention.

FIGS. 18A-B show that to allow for more transfer of leaflet load (high-stress region 130 near leaflet free edge) to the stent post 20 (as opposed to almost entirely through point loads from the sutures 90), individual leaflets 60*a-c* can be secured to caps 140 placed over the post tops. Caps 140 can be made from fabric, polymer, and/or tissue components.

Figure 19:
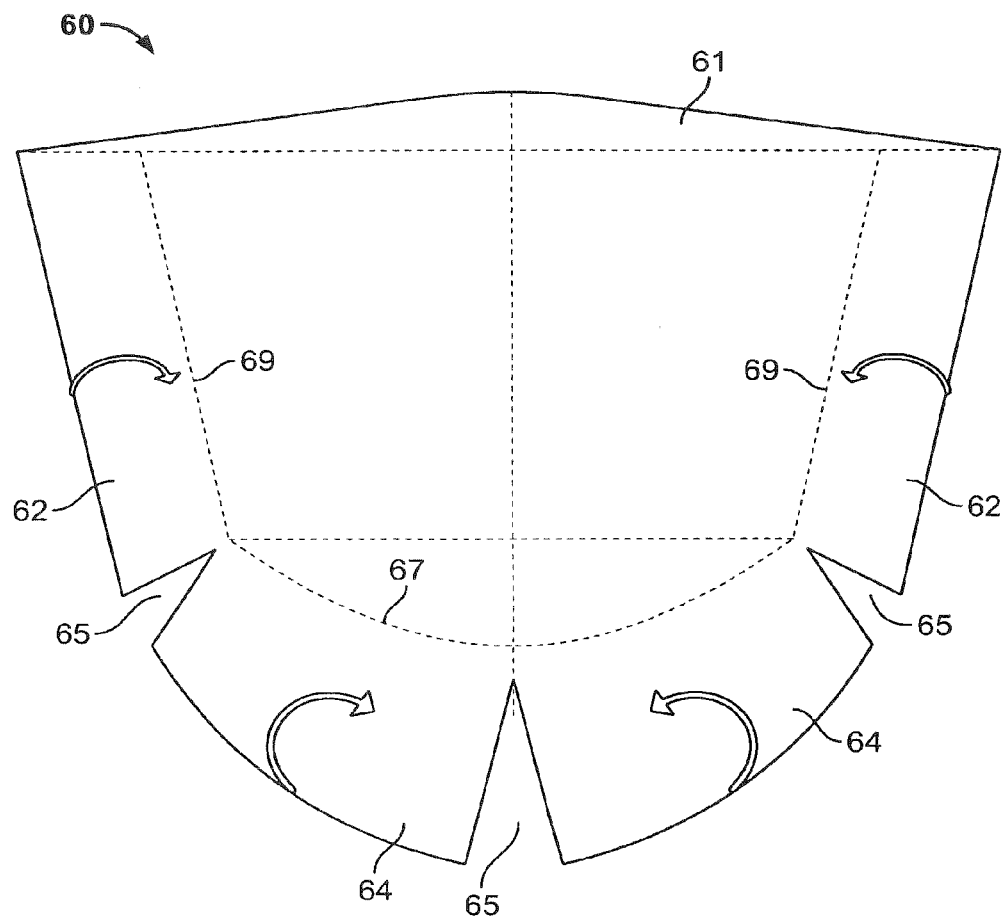
FIG. 19 is similar to FIG. 10 for another illustrative embodiment.

FIG. 19 shows another single leaflet design in which many of the same features as described in FIG. 10 can be utilized. The primary difference in this design is that the edge 62/64 is curled back onto the OD of the leaflet along the illustrated indicator lines 67/69, instead of folded around the base of the stent. So instead of the leaflet edge sealing for inflow of the stent skirt, this design forms a pocket under back-pressure, with no seams along the suture line. For a 3D illustration see the next FIGS. As with the previous design, when these flaps are folded back, the triangular sections 65 close so the leaflet does not buckle. Since these flaps are folded back up against the leaflet OD, when the leaflet opens, the flaps 64 actually form a buffer between the upper base stent portion 40 and the leaflet.

Figure 20A:
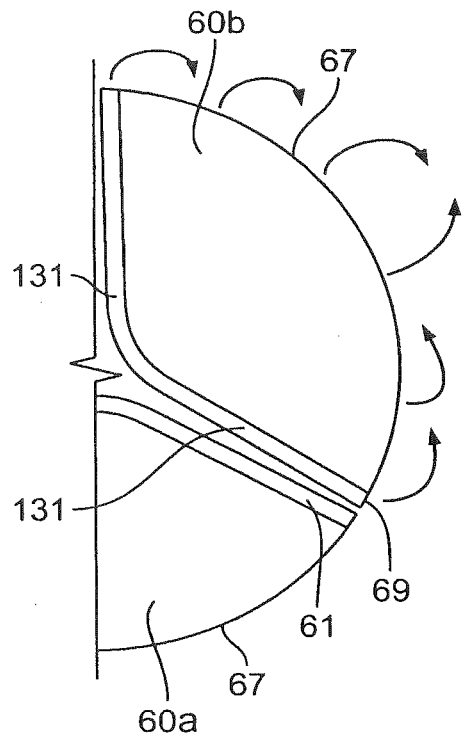
FIG. 20A is a simplified, partial, top view of an illustrative embodiment of an assembly of several components in accordance with the invention.
Figure 20B:
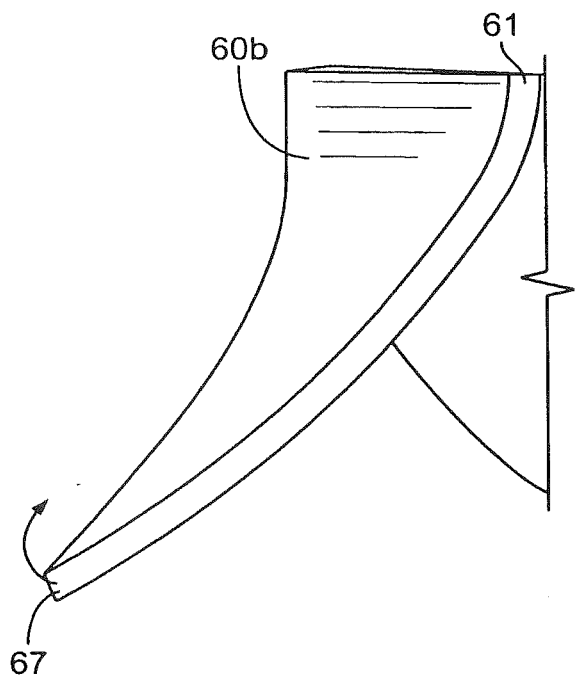
FIG. 20B is a simplified sectional view of part of what is shown in FIG. 20A.

FIGS. 20A-B shows 3D views of single leaflets 60. FIG. 20A is a top view cross section, and FIG. 20B is a side view cross section. The arrows indicate where the leaflet flaps 62/64 are folded back onto the leaflet OD for one representative leaflet 60*b*. Note that the curled-back design illustrated in FIGS. 12A-B is similar, except that in this design it runs along the entire edge 67/69 instead of just along the post.

Figure 21:
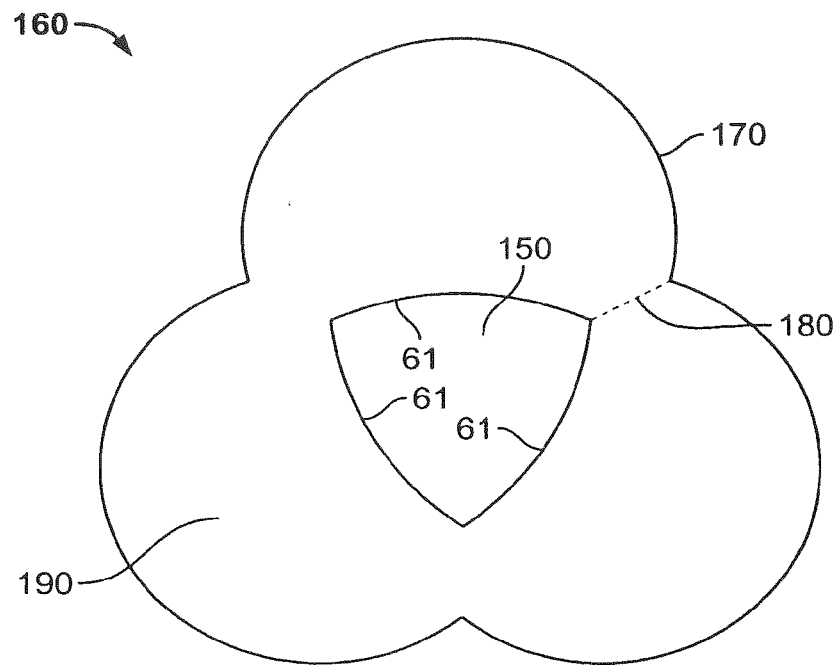
FIG. 21 is similar to FIG. 19 for another illustrative embodiment.

FIG. 21 shows a flat cutout of a continuous leaflet 160. Instead of three single leaflets 60*a-c* mating together to form an orifice 150, this design achieves this with one single continuous piece 160 of leaflet material. The indicated edge 170 is sewn to the stent ID in a similar manner as already described. Dashed line 180 indicates where leaflet material 160 is creased to form a commissure and attached to a post 20. When the flat portion 190 of this design is pushed toward the central axis, it forms a belly as shown in the next FIG.

Figure 22:
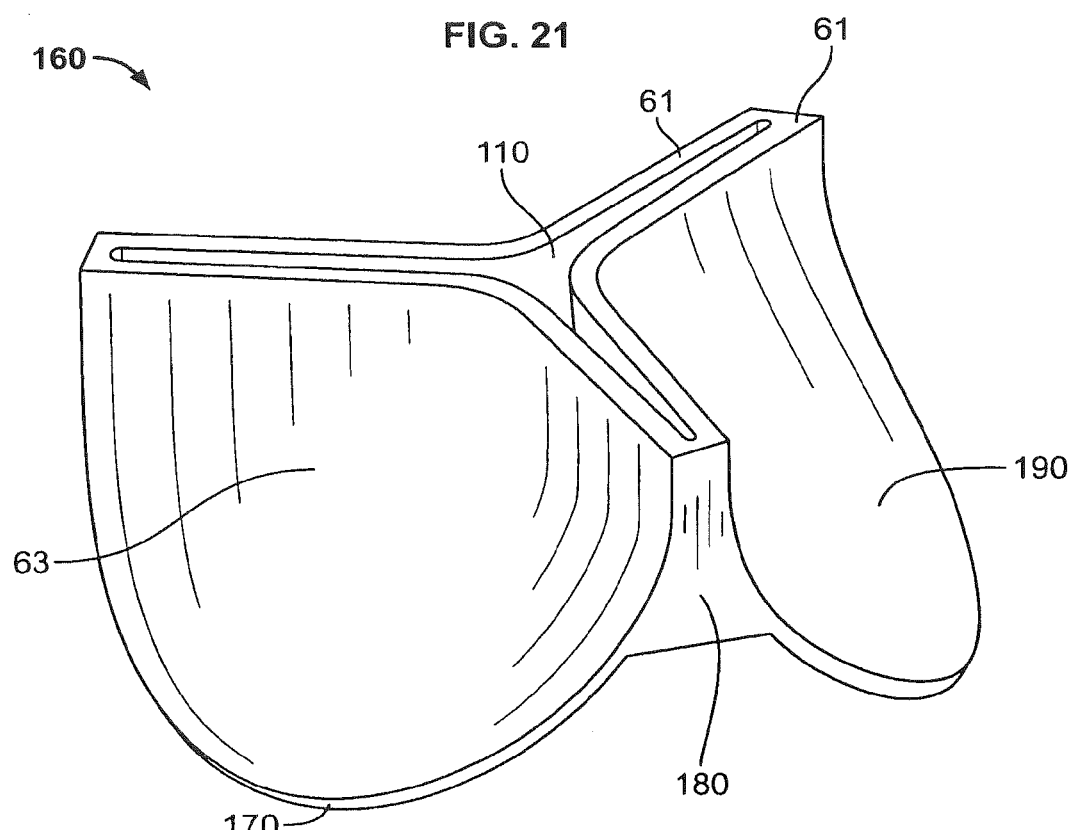
FIG. 22 is similar to FIG. 18A for another illustrative embodiment.

FIG. 22 shows a folded 3D illustration of continuous leaflets material 160. See the above discussion of FIG. 21 for item descriptions.

Figure 23A:
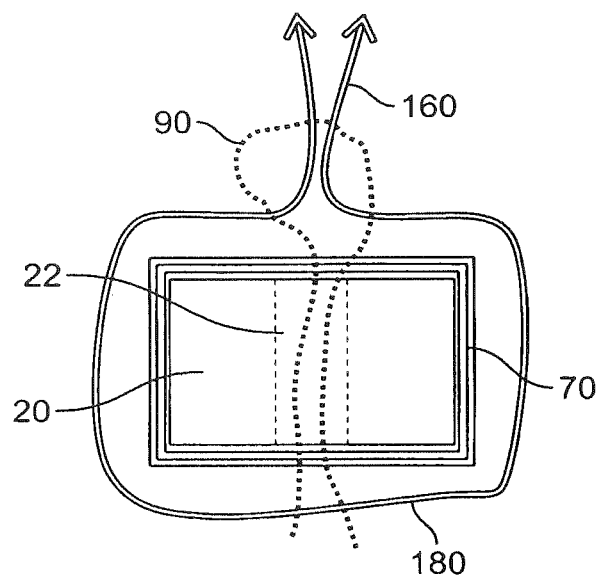
FIG. 23A is similar to FIG. 12C for another illustrative embodiment.
Figure 23B:
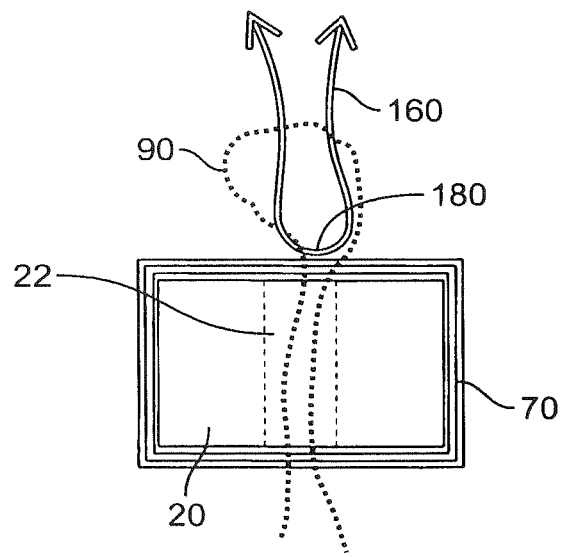
FIG. 23B is similar to FIG. 23A for another illustrative embodiment.

FIGS. 23A-B show two methods for leaflet 160 and ancillary component assembly. These are views similar to FIGS. 12A and 12C, with the same reference numbers used again for similar components. Major features to note are as follows: (1) a buffering layer 70 between the stent 20 and the leaflet material 160 reduces abrasion, (2) leaflets 60 (from continuous leaflet structure 160) are sutured together to minimize any post gapping, (3) suture knots are on the OD of the post 20 so as not to interfere with leaflet movement/abrasion, and (4) bottom edge of the leaflets are curled back up toward the center of the valve to allow for an additional buffering layer (analogous to the folding along line 67 in FIGS. 20A and 20B). Note that the main difference in attachment techniques is that either the leaflet material 160 wraps around the entire stent post (FIG. 23A) if there is enough room between cells when the valve is collapsed, or the leaflet material 160 is folded on the post ID only (FIG. 23B) in a continuous manner.

Figure 24A:
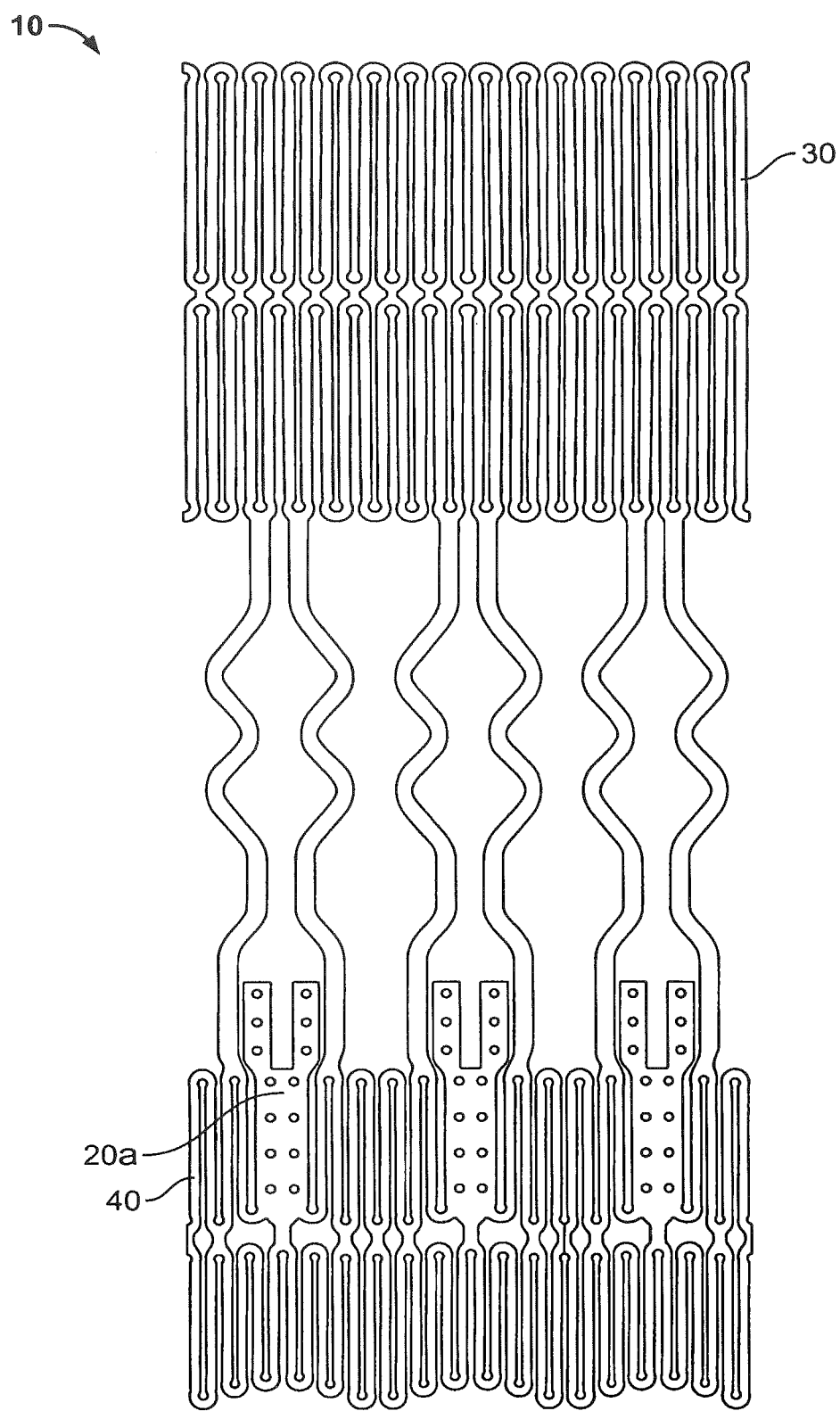
FIG. 24A is similar to FIG. 5A for another illustrative embodiment.
Figure 24B:
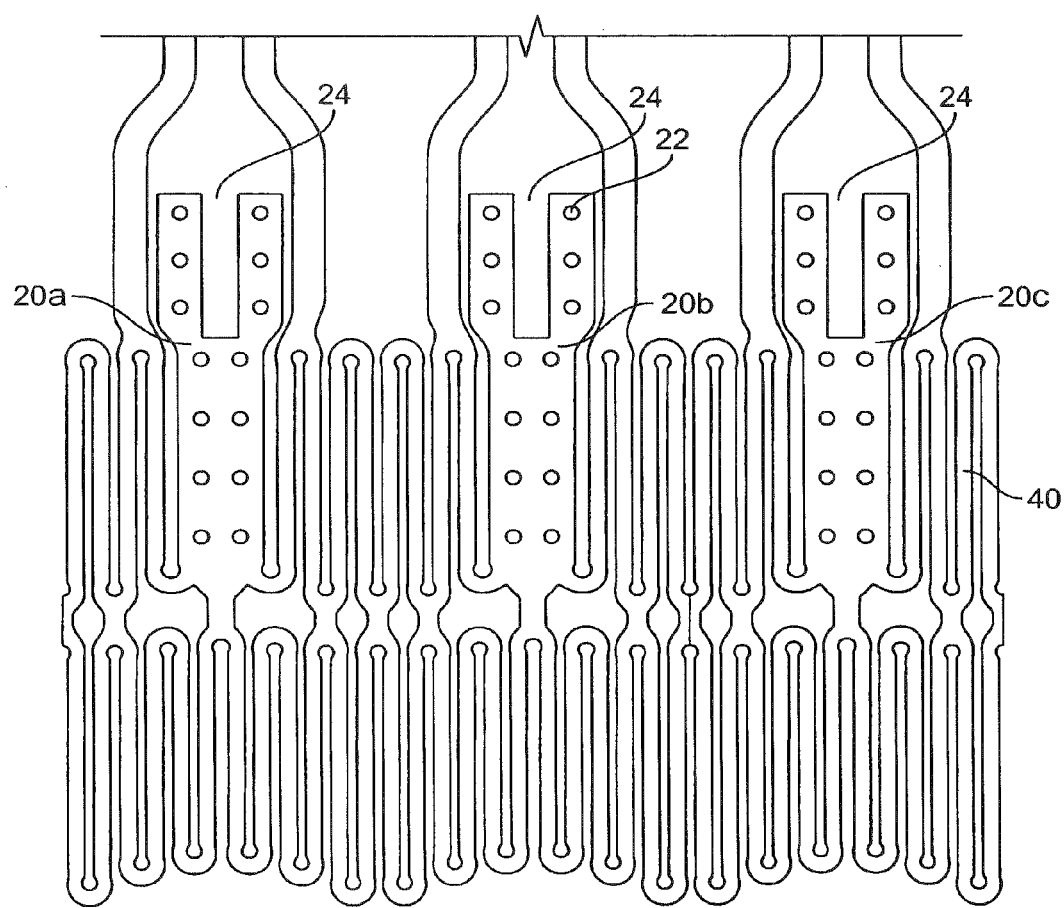
FIG. 24B is similar to FIG. 5B for another illustrative embodiment.

FIGS. 24A-B show the flat and collapsed state of a stent model used to laser cut a part (stent 10) from a tube and a close-up of the independent posts 20. This stent has independent flexing posts 20 that are solid, with two sets of eyelets 22, and an open section 24 at the top that forks (bifurcates) into two separate portions. See FIGS. 1-5 for general features that are applicable to this and other designs.

A buffering layer 70 that can outline the ID of this stent 10 can be seen in FIGS. 6-8, but would have a fork-shaped top.

Figure 25A:
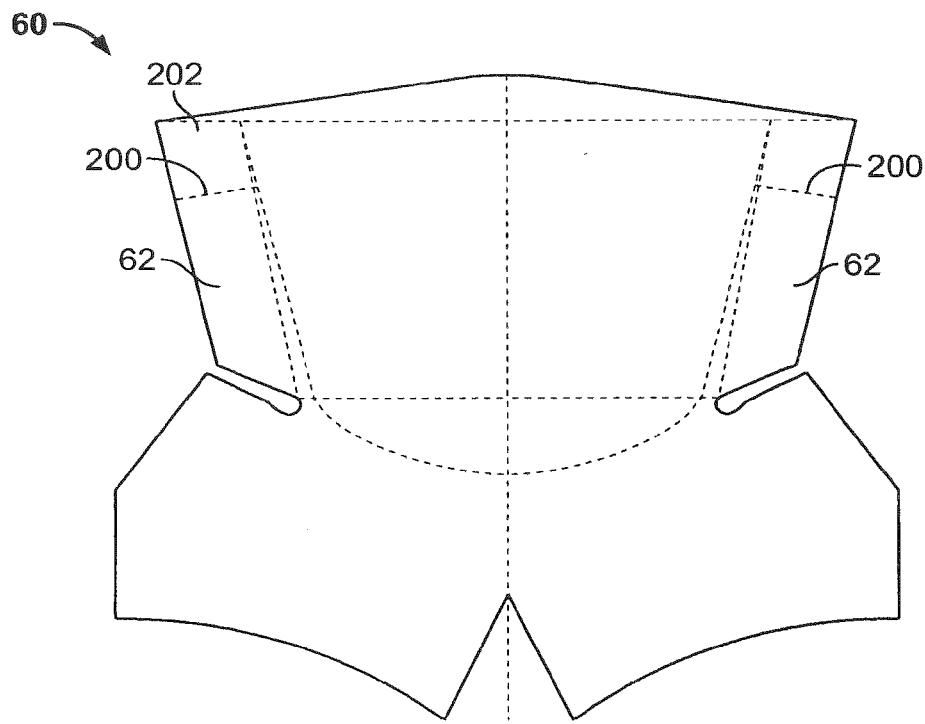
FIGS. 25A and 25B are each similar to FIG. 21 for other illustrative embodiments.
Figure 25B:
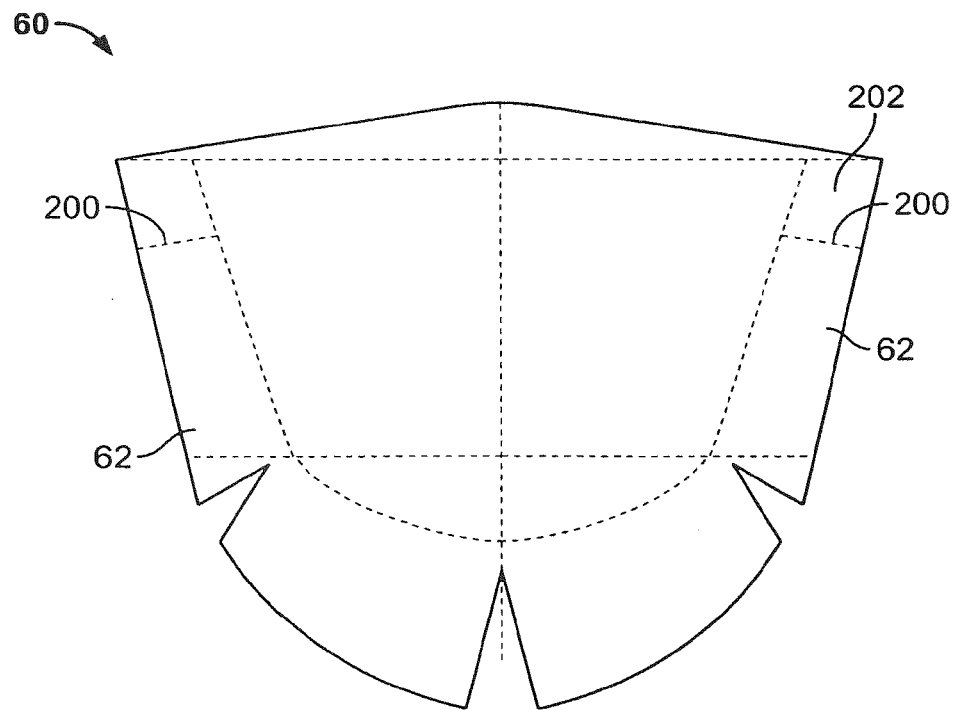

FIGS. 25A-B show single leaflet designs (with many of the same features as conveyed in FIGS. 10 and 19) that can be used for this stent design. The main difference is that the side flaps 62 have a slit 200 in them that allows the flap to wrap around the OD of the fork (on both sides of open section 24) at the top of the stent post 20.

Figure 26A:
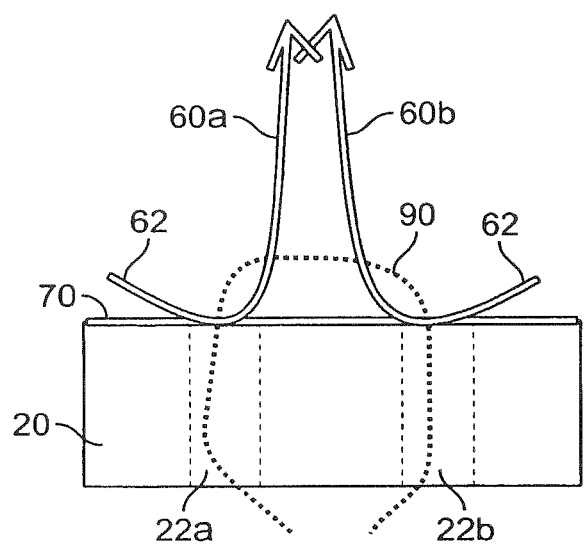
FIGS. 26A and 26B are each similar to FIG. 23B for other illustrative embodiments.
Figure 26B:
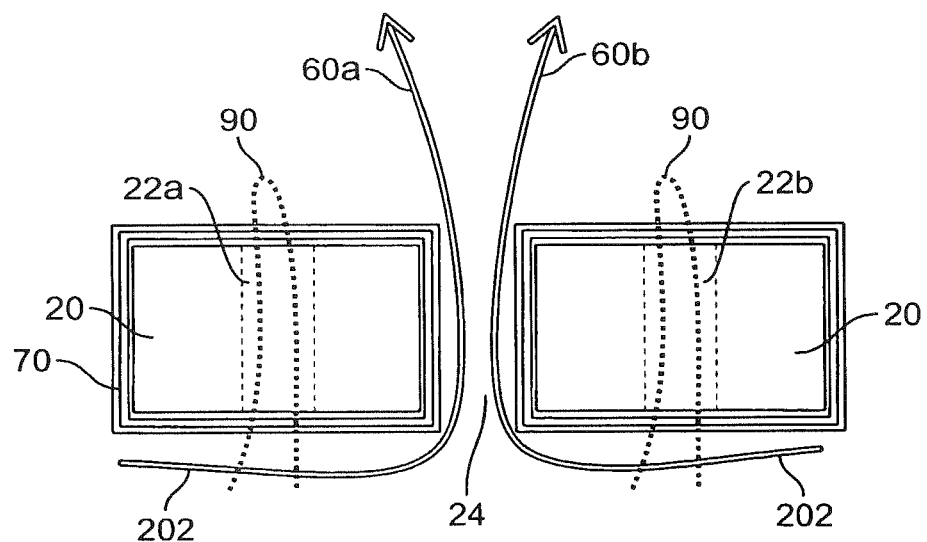

FIGS. 26A-B show two methods for leaflet 60 and ancillary component assembly. Once again, these are views that are similar to FIGS. like 12 and 23, with the same reference numbers being used again for similar components. Major features to note are as follows: (1) a buffering layer 70 between stent 10 and leaflets 60 reduces abrasion, (2) leaflets 60 are sutured together (using sutures 90) to minimize any post gapping, (3) suture knots are on the OD of the post 20 so as not to interfere with leaflet movement/abrasion, (4) free ends 62 of leaflets 60 are curled back toward the center of the valve to provide an additional buffering layer in FIG. 26A, (5) the gap 24 between forked posts 20 is just large enough for leaflet thicknesses to eliminate post gapping, and (6) the leaflets attached to the OD as in FIG. 26B allow for stresses caused from blood flow back-pressure to be transferred to the stent frame 10 instead of point loads at suture attachments.

Figure 27:
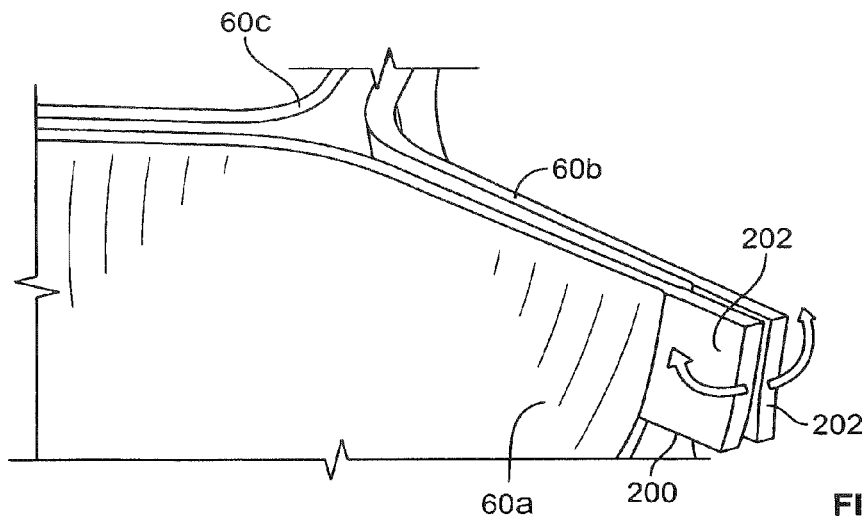
FIG. 27 is similar to FIG. 22 for another illustrative embodiment.

FIG. 27 shows a 3D view of individual leaflets 60 and the top portion 202 of the side flaps (above slit 200 in FIG. 25A or 25B) that wrap around the forked top section of the stent post 20.

Figure 28:
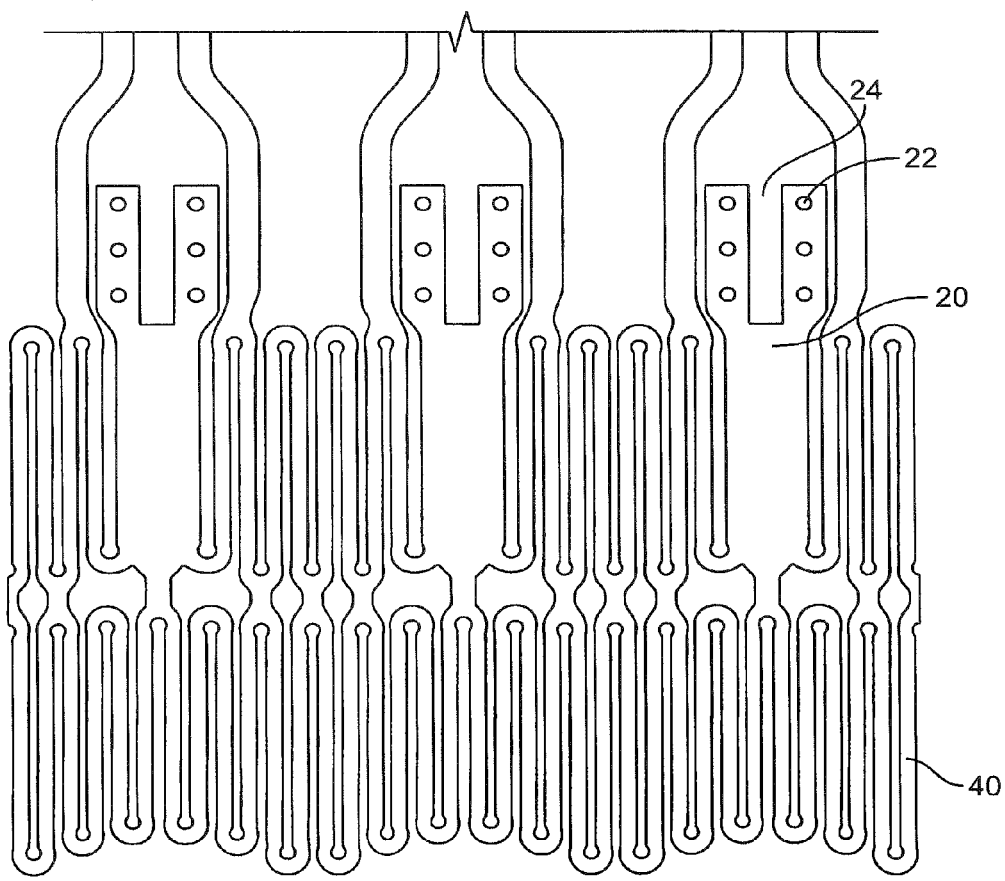
FIG. 28 is similar to FIG. 24B for another illustrative embodiment.

FIG. 28 shows that another variation of this stent design is to eliminate the eyelets 22 on the lower portion of posts 20. If there are no orifices to attach the leaflet flaps 62 to the posts, the leaflet flaps can be sutured together along the length of this lower section and/or through cuff material surrounding the expandable stent portion.

Figure 29A:
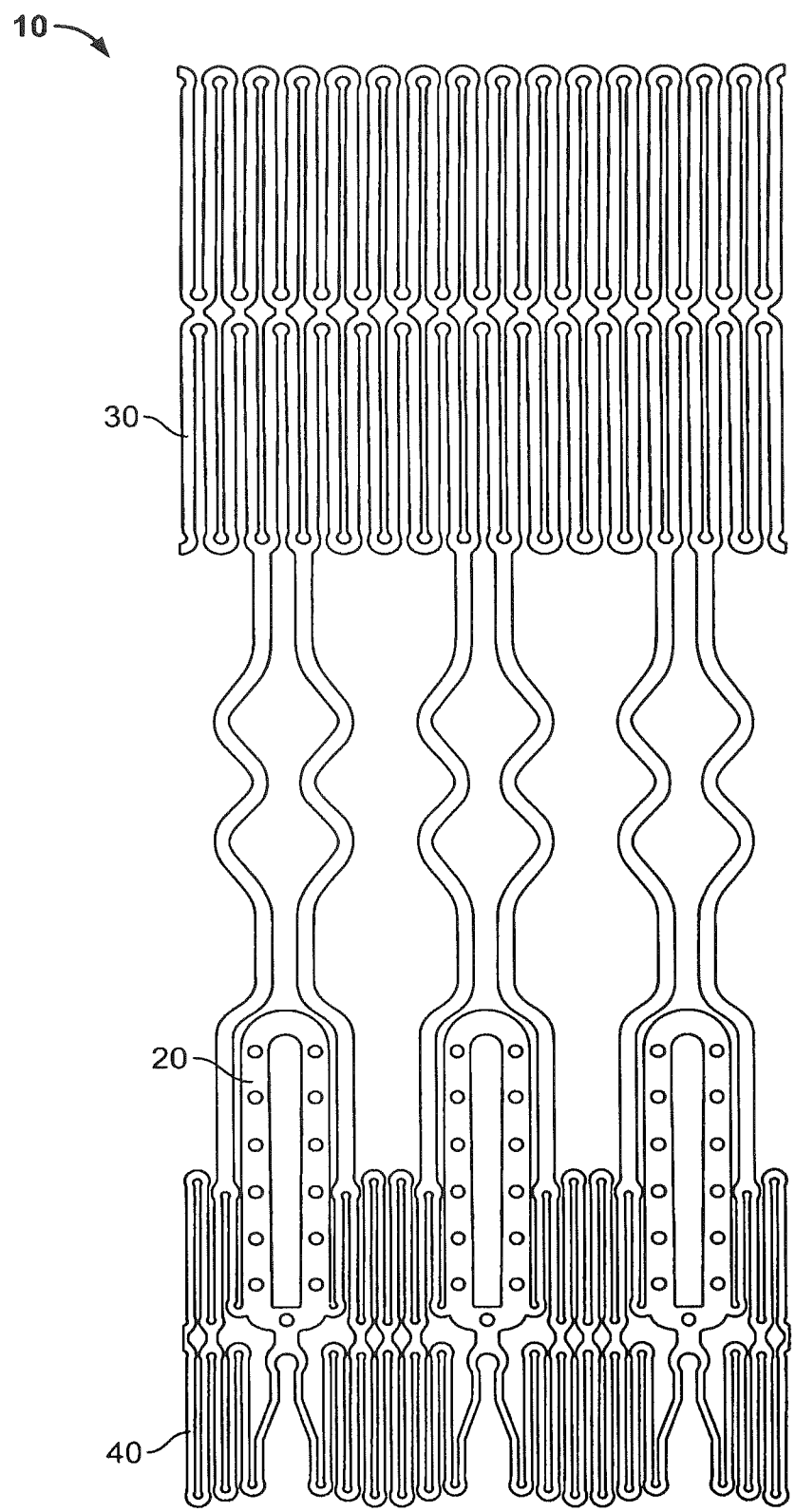
FIGS. 29A and 29B are respectively similar to FIGS. 24A and 24B for another illustrative embodiment.
Figure 29B:
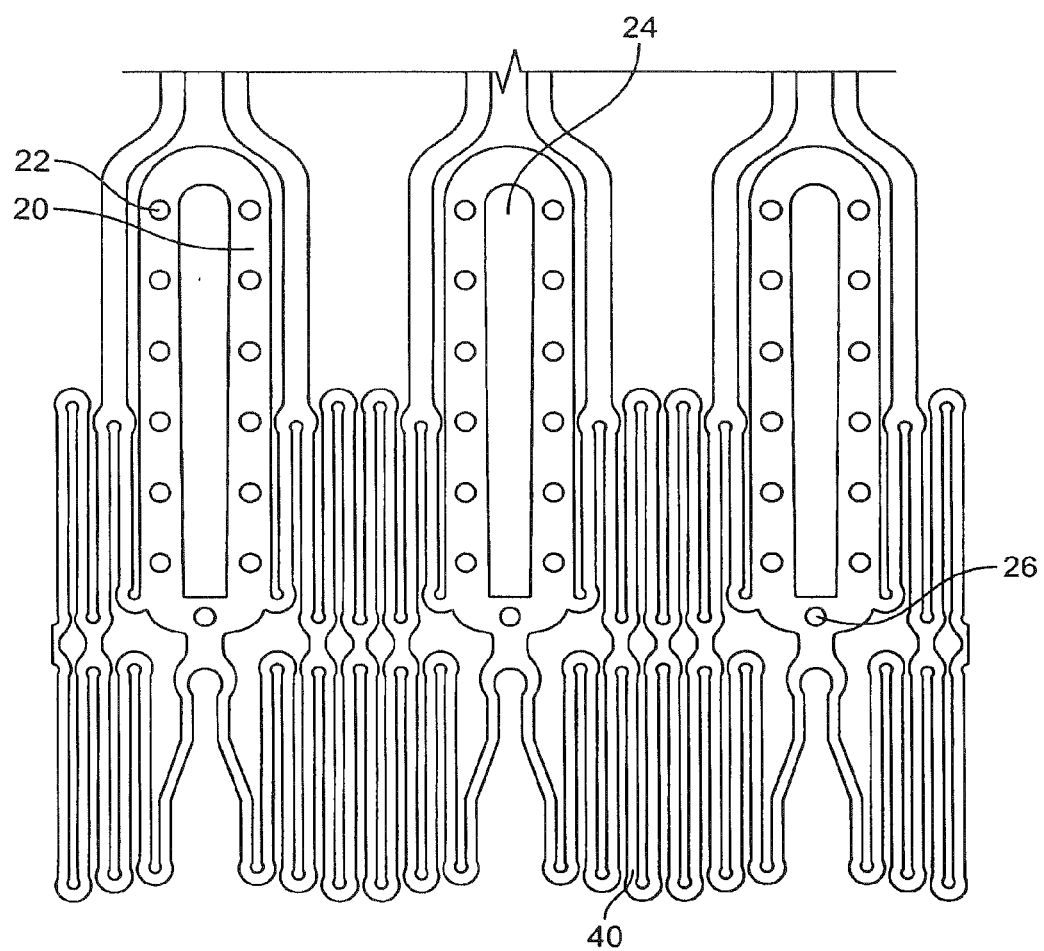

FIGS. 29A-B show the flat and collapsed state of a stent model used to laser cut a part (stent 10) from a tube and a close-up of the independent posts 20. This stent has independent flexing posts 20 that are open in the middle 24 (i.e., bifurcated) with two sets of eyelets 22. It also has a terminating single eyelet 26 for anchoring the leaflet base and other materials. See again FIGS. 1-5 for general features that are applicable to this and other designs.

Figure 30:
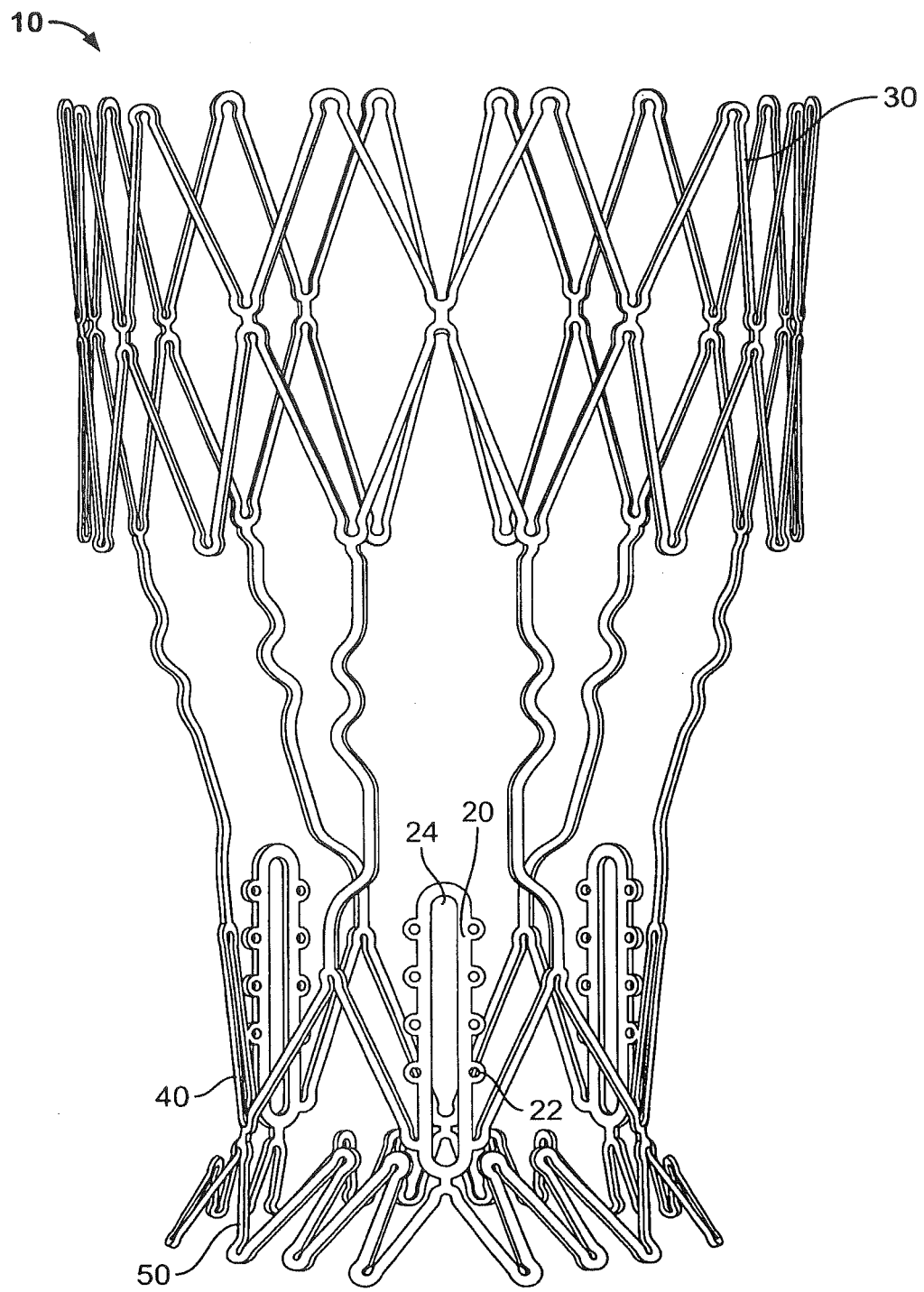
FIG. 30 is similar to FIG. 1A for another illustrative embodiment.

FIG. 30 shows an example of a design variation with the non-expanding open stent post 20 and flared skirt 50.

Figure 31:
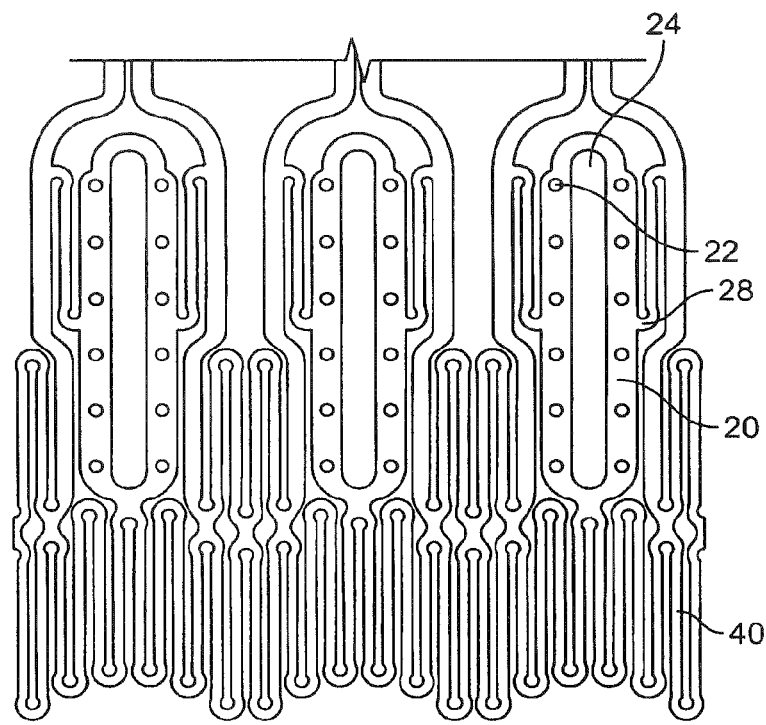
FIG. 31 is similar to FIG. 29B for another illustrative embodiment.

FIG. 31 shows a close-up of the flat and collapsed state of a stent model used to laser cut a part (stent 10) from a tube with independent commissure posts 20. This stent has independent flexing posts 20 that are open in the middle (i.e., at 24), with two sets of eyelets 22. Additionally, this design has a connection 28 higher up on the stent posts 20, thus making the posts less cantilevered and therefore possibly less flexible if needed. However, the valve assembly is not disrupted when internally mounting the leaflets through the center slot 24 of the stent posts. See again FIGS. 1-5 and 29 for general features that are applicable to this and other designs.

Figure 32:
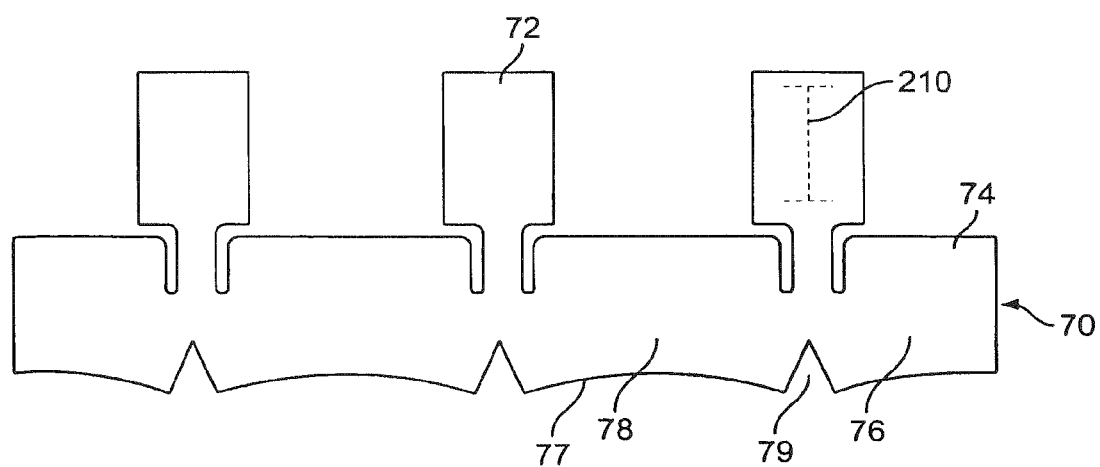
FIG. 32 is similar to FIG. 8 for another illustrative embodiment.

FIG. 32 shows a buffering layer design including features that can be in addition to those shown in FIG. 6. Rectangular flaps 72 outline the ID of stent posts 20. An "I" shaped slit 210 is cut through material 70 and the resulting flaps are wrapped through the middle portion 24 of the stent post 20 from the ID to the OD, then secured in place.

Figure 33A:
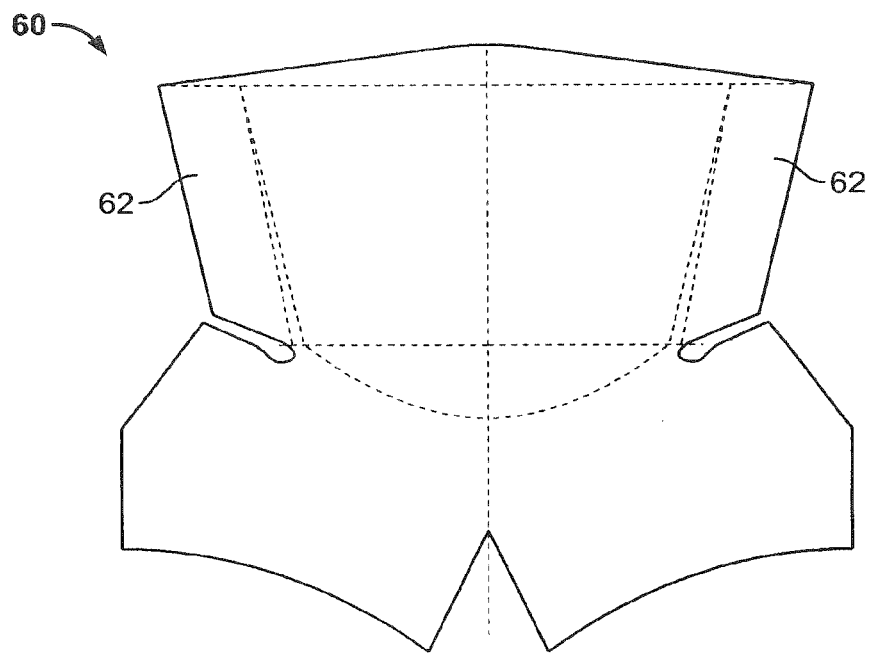
FIGS. 33A and 33B are each similar to FIG. 25B for other illustrative embodiments.
Figure 33B:
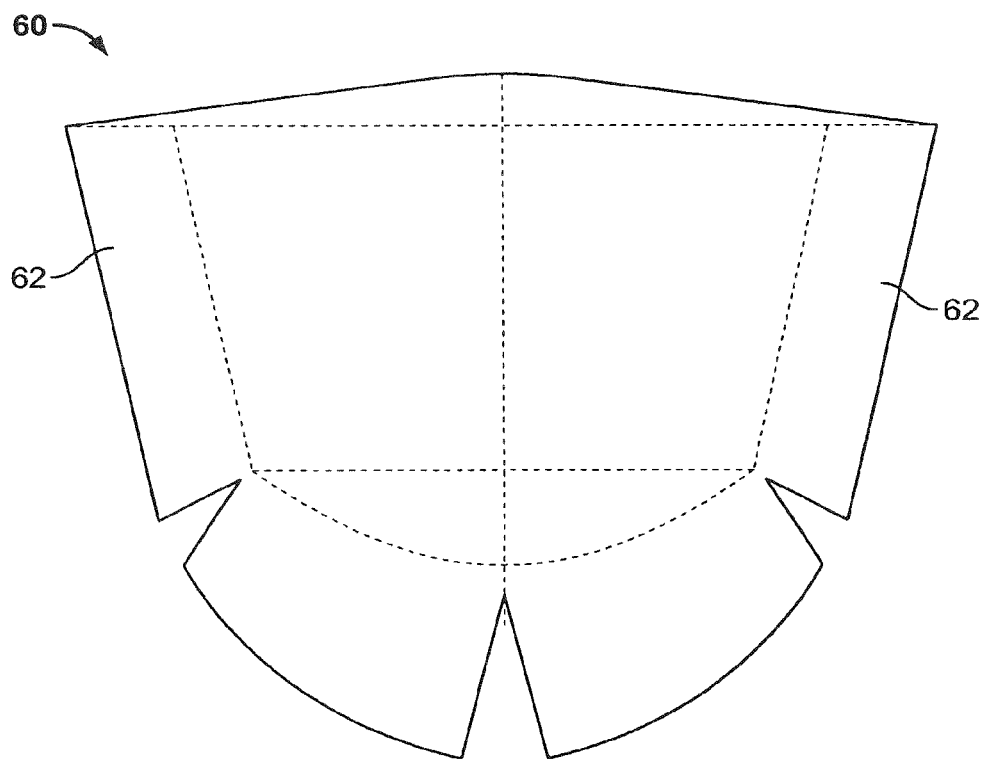

FIGS. 33A-B show single leaflet designs, with many of the same features as conveyed in FIGS. 10 and 19, which can be applied to this stent design. The main difference is that the entire side flaps 62 pass through the middle slot (24 of FIG. 29) and around to the OD, where it is secured (see next FIG.).

Figure 34:
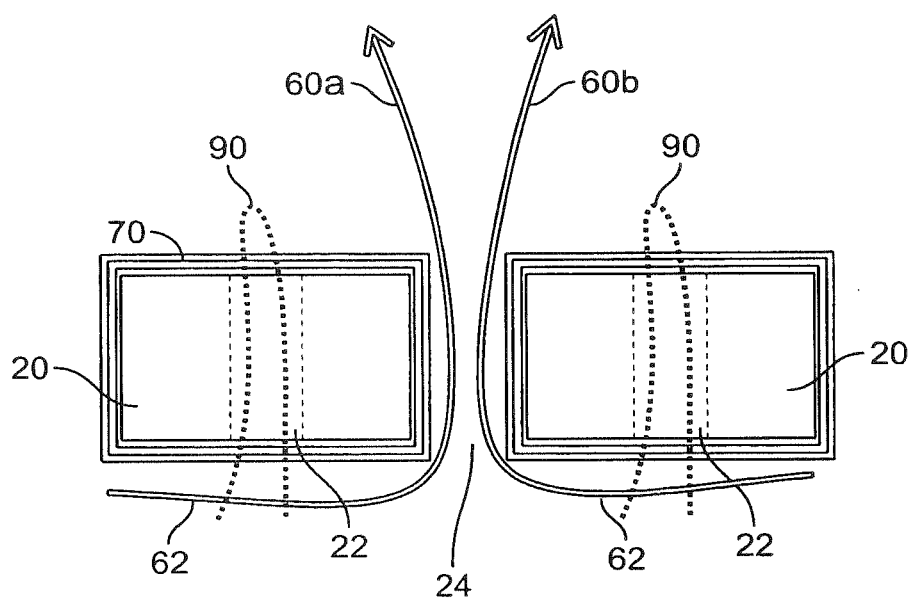
FIG. 34 is similar to FIG. 26B for another illustrative embodiment.

FIG. 34 shows one method for leaflet and ancillary component assembly. Once again, this is a view similar to FIGS. like 12 and 23, with the same reference numbers being used again for similar elements. Major features to note are as follows: (1) a buffering layer 70 between the stent 10 and the leaflets 60 reduces abrasion, (2) the gap 24 between sides of the post 20 is just large enough for leaflet thicknesses to eliminate post gapping, (3) suture knots (associated with sutures 90) are on the OD of the post 20 so as not to interfere with leaflet movement/abrasion, and (4) the leaflets 60 attached to the OD of posts 20 allow for stresses caused by blood-flow back-pressure to be transferred to the stent frame instead of point loads at suture attachments.

Figure 35A:
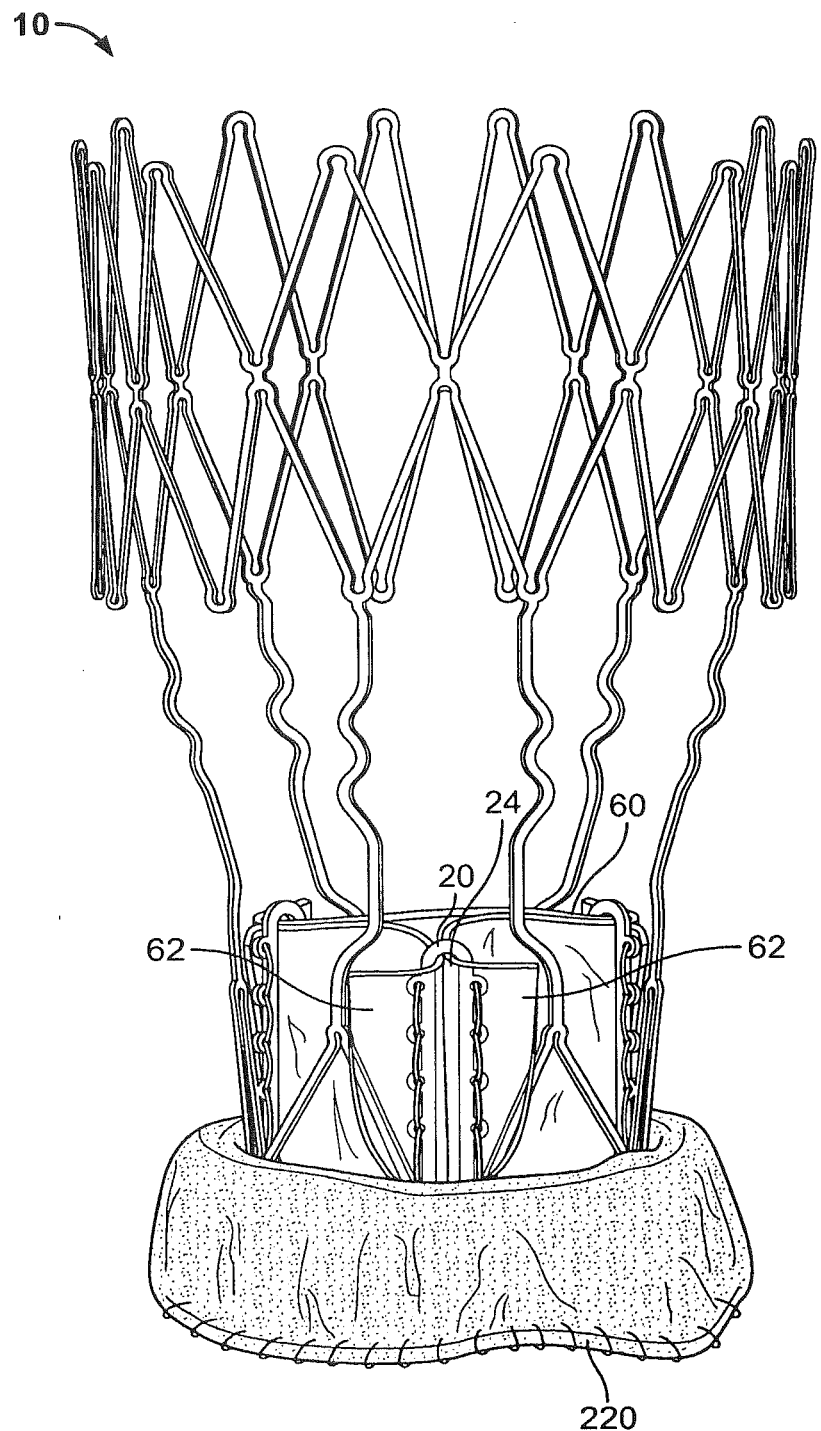
FIGS. 35A and 35B are each similar to FIG. 15B for another illustrative embodiment.
Figure 35B:
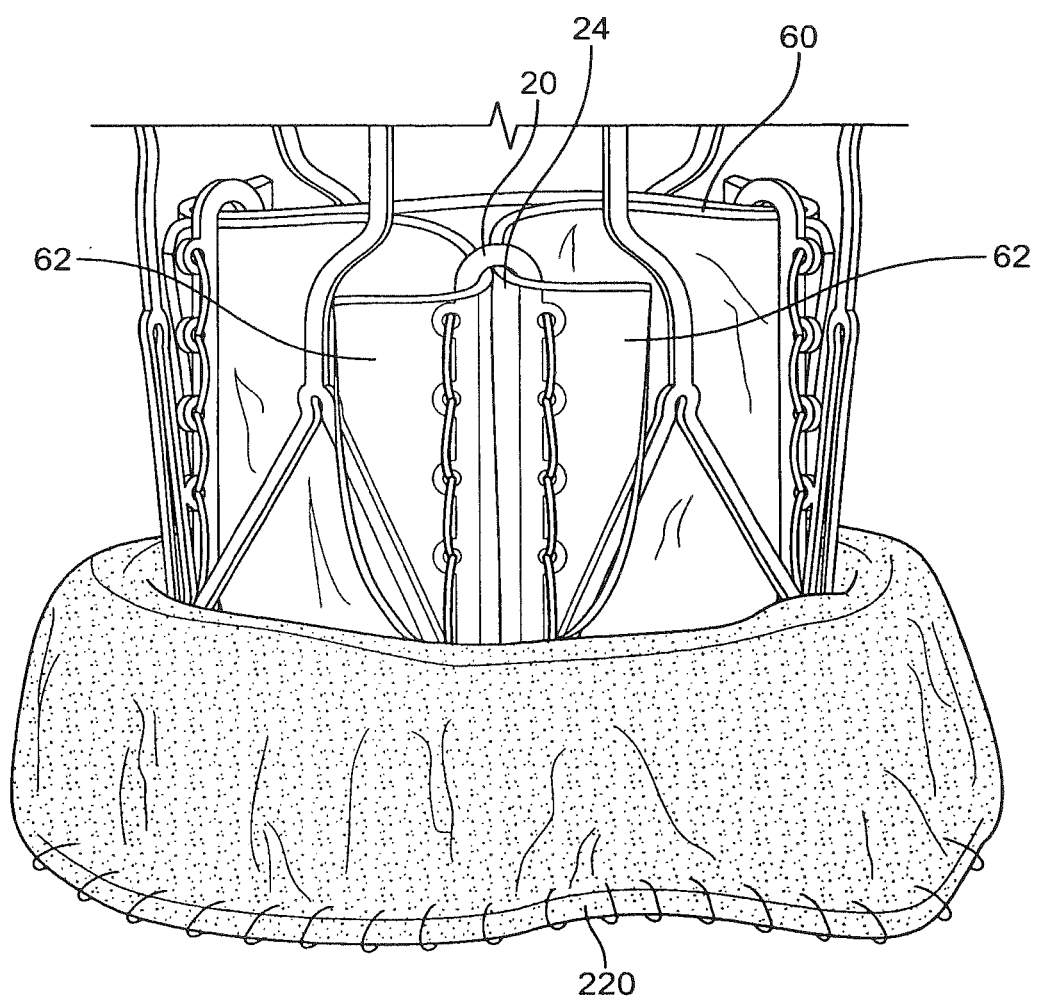

FIGS. 35A-B show an example of this type of design with single leaflets 60 pulled through a center slot 24 and wrapped around to the OD of the stent post 20. Also note that the buffering material 70 and leaflets 60 wrap slightly around the stent base as indicated at 220. In some areas these FIGS. show the leaflet material as though transparent.

Figure 36:
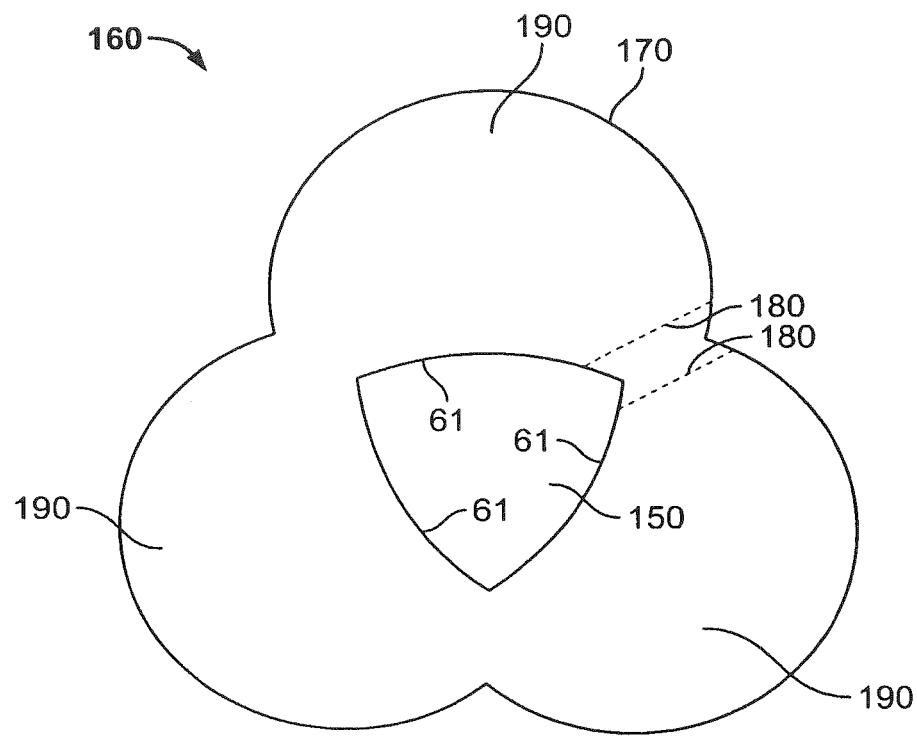
FIG. 36 is similar to FIG. 21 for another illustrative embodiment.

FIG. 36 shows a flat cutout of a continuous leaflet 160. Instead of three single leaflets 60 mating together to form an orifice 150, this design achieves this with one single continuous piece 160. The indicated edge 170 is sewn to the stent ID in a similar manner as already described. Dashed lines 180 indicate where one representative commissure of the leaflets is creased and pulled through the central slot 24 of the post 20. When the flat portion 190 of this design is pushed toward the central axis, it forms a belly as shown in previous FIGS.

Figure 37:
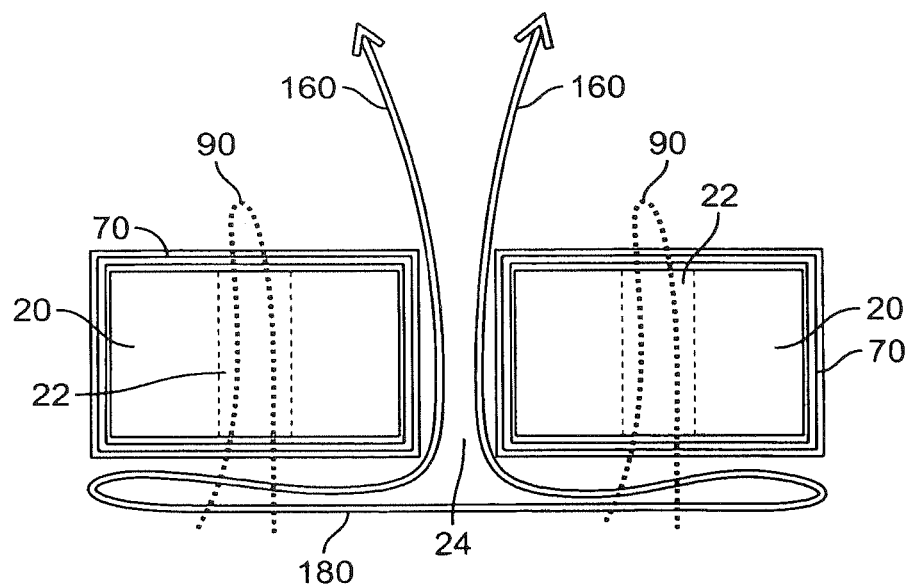
FIG. 37 is similar to FIG. 34 for another illustrative embodiment.

FIG. 37 shows one method for leaflet and ancillary component assembly. Again, FIG. 37 is a view similar to FIGS. like 12 and 23, and the same reference numbers are used in all FIGS. of this type to indicate similar components. Major features to note are as follows: (1) a buffering layer 70 between the stent 10 and the leaflets 160 reduces abrasion, (2) the gap 24 between sides of the post 20 is just large enough for leaflet thicknesses to eliminate post gapping, (3) suture knots (associated with sutures 90) are on the OD of the post 20 so as not to interfere with leaflet 160 movement/abrasion, (4) the leaflets 160 attached to the OD (at 180) allow for stresses caused from back-pressure to be transferred to the stent frame 10 instead of point loads at suture attachments, and (5) the leaflet 160 is fully sealed at the commissures 20.

Figure 38A:
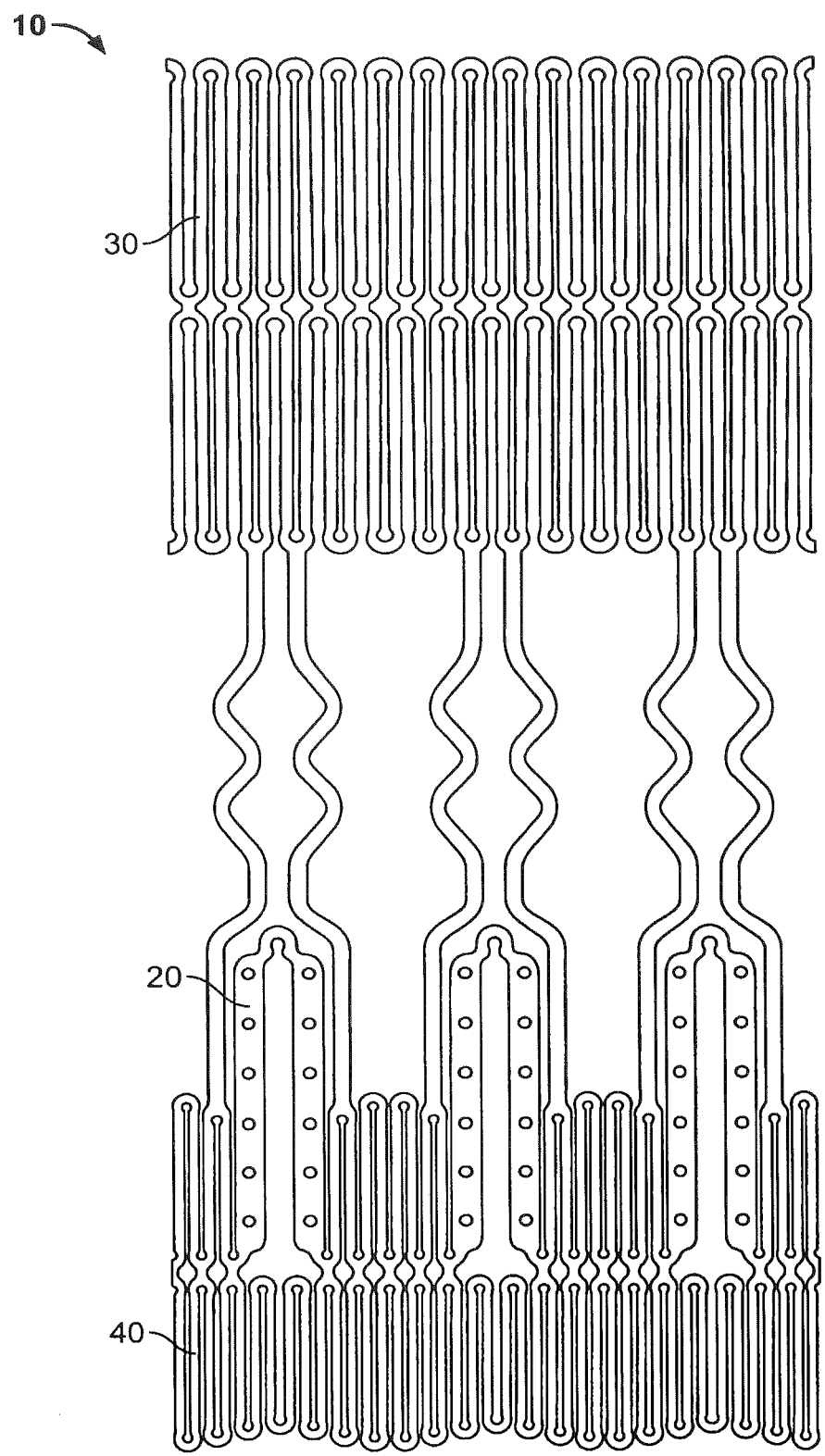
FIGS. 38A and 38B are respectively similar to FIGS. 29A and 29B for another illustrative embodiment.
Figure 38B:
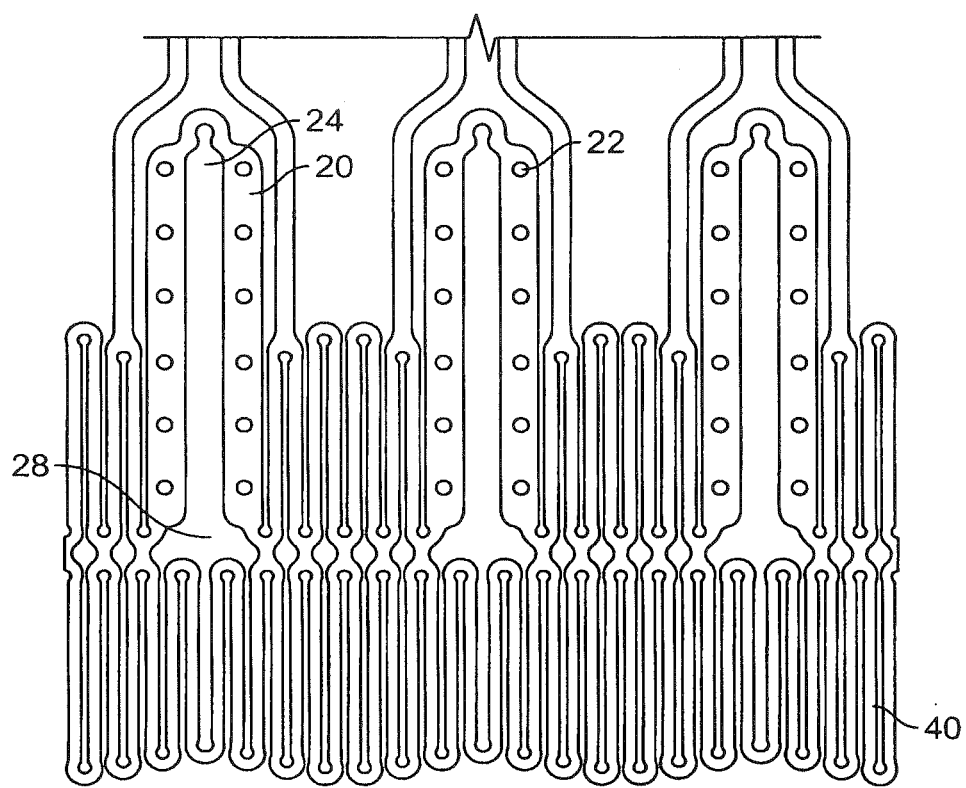

FIGS. 38A-B show the flat and collapsed state of a stent model used to laser cut a part (stent 10) from a tube and a close-up of the independent commissure posts 20. This stent has independent flexing posts 20 that are open in the middle 24 with two sets of eyelets 22. Additionally, this design has an opening 28 at the bottom of the slot 24, which allows the post 20 to expand into a triangular shape. See again FIGS. 1-5 for general features that are applicable to this and other designs.

Figure 39:
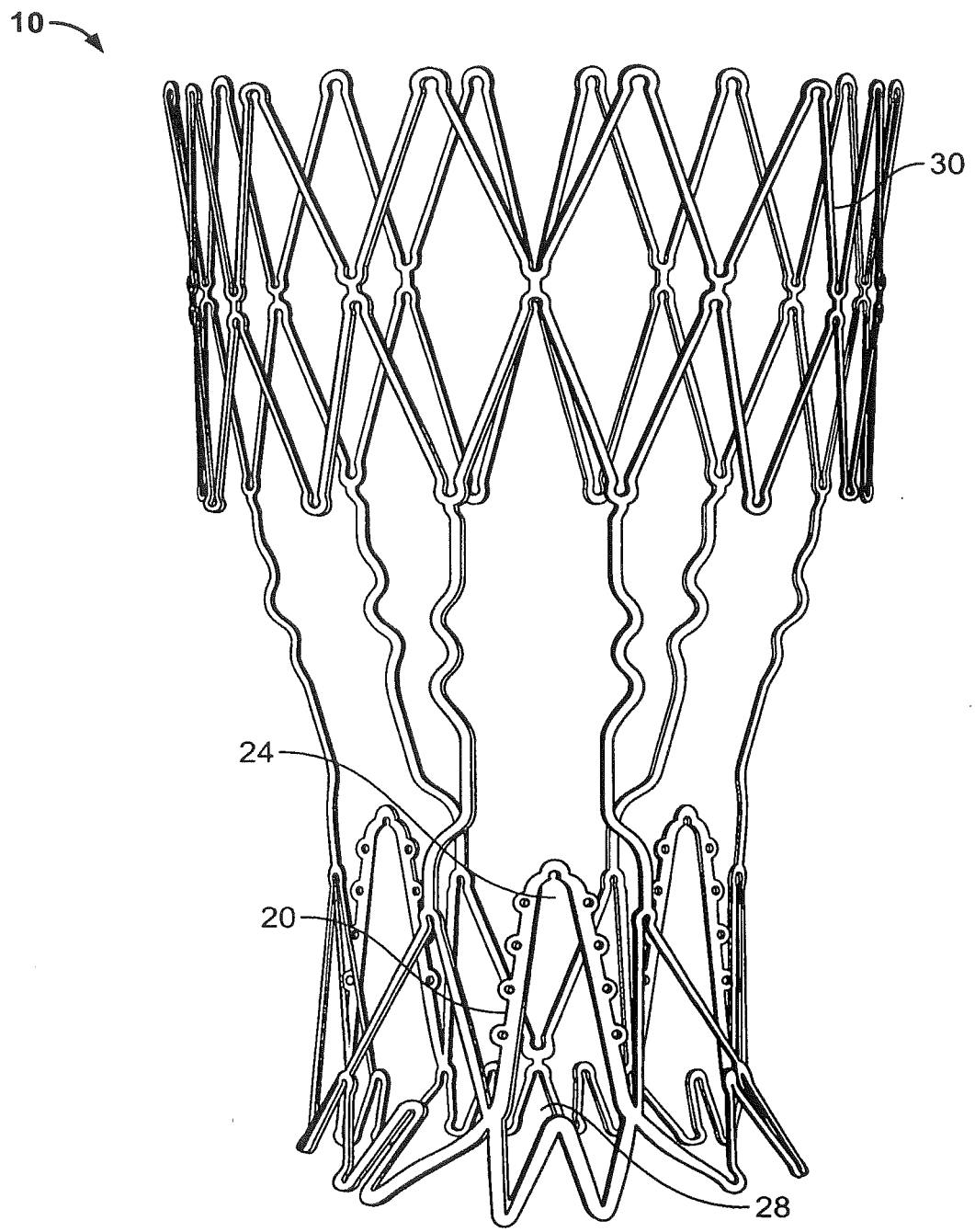
FIG. 39 is similar to FIG. 30 for another illustrative embodiment.

FIG. 39 shows an example of a stent variation with a central vertical slot 24 when in a collapsed state that was formed into a triangular opening 24/28 in an expanded state. The triangular opening of this post 20 more closely mimics the contoured shape of a native valve than, say, a vertical non-expanding post.

Figure 40:
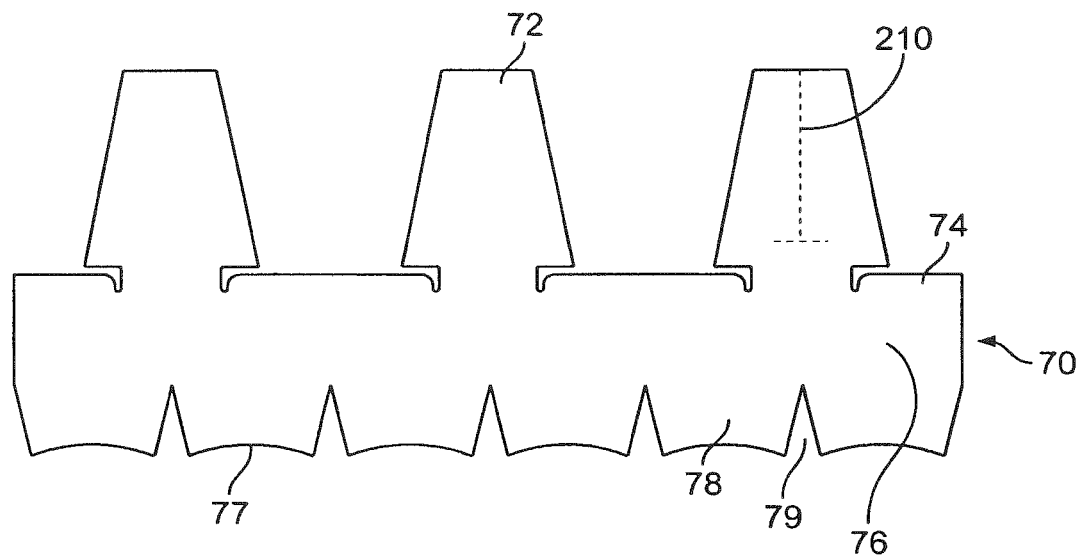
FIG. 40 is similar to FIG. 32 for another illustrative embodiment.

FIG. 40 shows a buffering layer design including features that can be in addition to those shown in FIG. 6. The upwardly extending post flaps 72 outline the ID of stent posts 20 when those posts are expanded into a triangular shape (e.g., as shown at 24/28 in FIG. 39). A slit 210 is cut through buffering material 70 and the resulting flaps are wrapped through the middle portion 24/28 of the stent posts 20 from the ID to the OD, then secured in place.

Figure 41A:
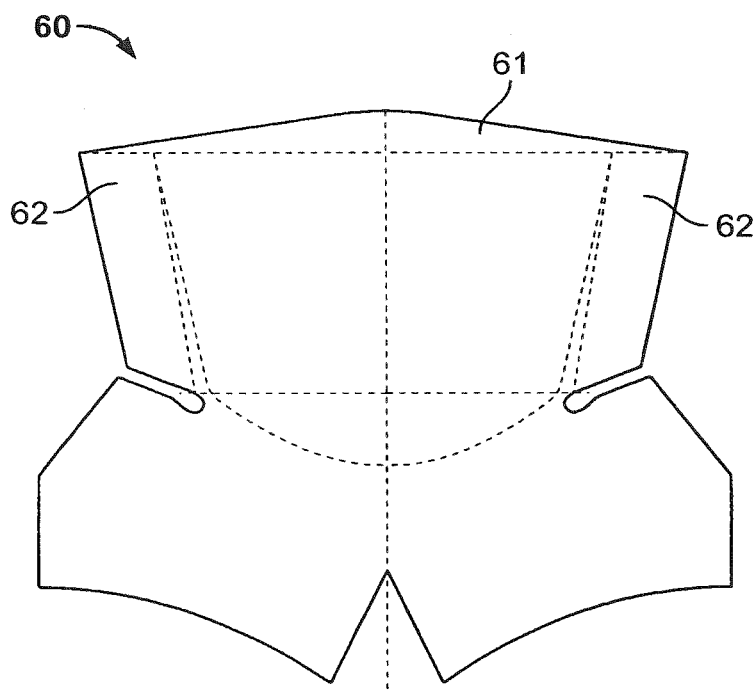
FIGS. 41A and 41B are each similar to FIG. 33B for other illustrative embodiments.
Figure 41B:
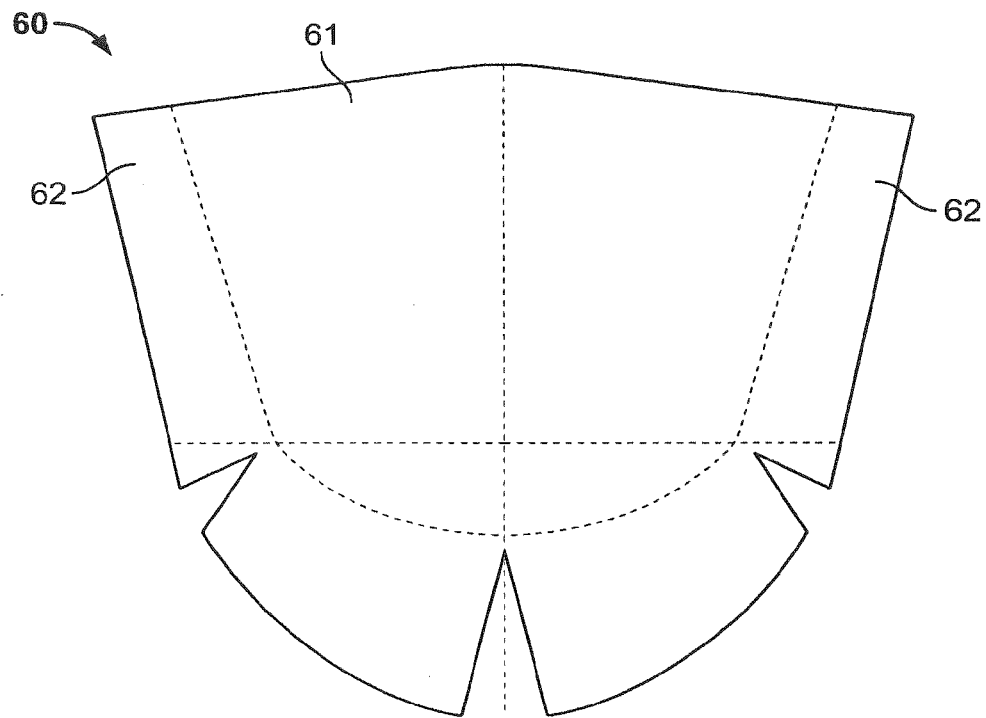

FIGS. 41A-B show single leaflet designs, with many of the same features as conveyed in FIGS. 10 and 19, which can be applied to this stent design. The main difference is that the side flaps 62 at the commissures are spread apart (due to the triangular stent post opening 24/28), thus additional sealing measures are needed.

Figure 42:
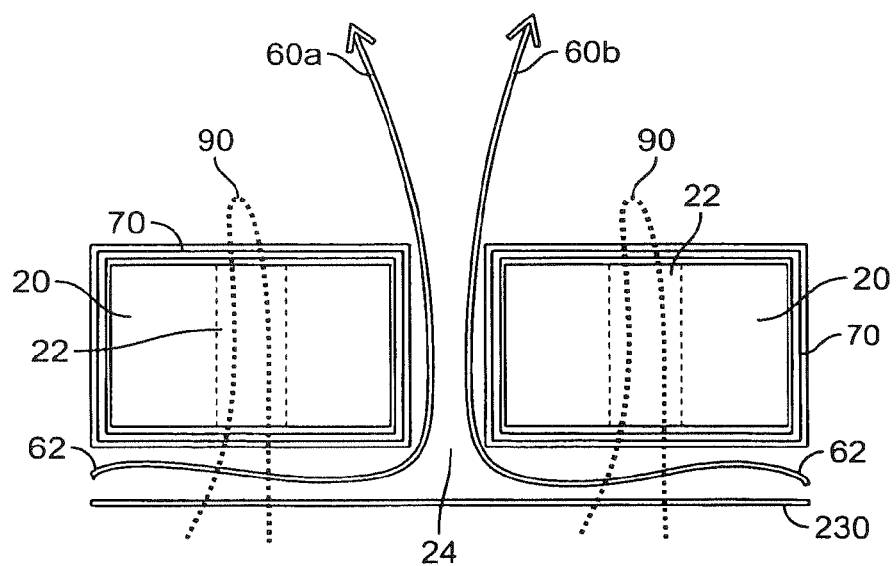
FIG. 42 is similar to FIG. 37 for another illustrative embodiment.

FIG. 42 shows one method for leaflet and ancillary component assembly. This is yet another FIG. similar to FIGS. like 12 and 23, and which uses the same reference numbers for similar elements. In addition, line 230 indicates a patch having the same or similar material properties as elements 70 or 60 that seals the triangular opening 24/28 in the posts 20. Major features to note are as follows: (1) a buffering layer 70 between the stent 10 and the leaflets 60 reduces abrasion, (2) suture knots (associated with sutures 90) are on the OD of the post 20 so as not to interfere with leaflet movement/abrasion, (3) the leaflets 60 attached to the OD via flaps 62 allow for stresses caused from back-pressure to be transferred to the stent frame 10 instead of point loads at suture attachments 90, and (4) the triangular-shaped posts 20/24/28 more closely mimic the contour shape of a native valve, thus functioning more optimally.

Figure 43:
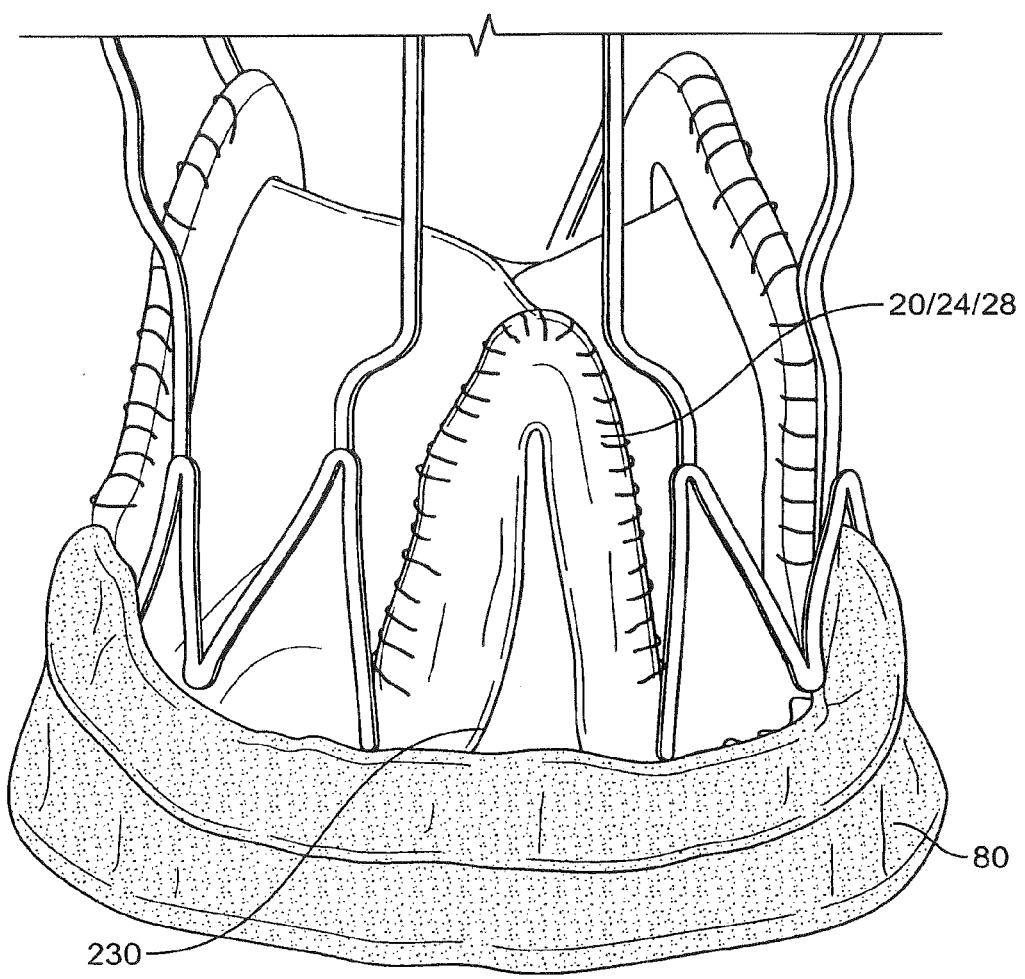
FIG. 43 is similar to FIG. 35B for another illustrative embodiment.

FIG. 43 shows an example of a stent variation with an open expanding post 20 that results in a triangular commissure area 24/28 that more closely mimics the contour shape of a native valve. A patch 230 is sutured through the eyelets 22 and around the base of the stent 10 to ensure a sealed environment. Note also that there is a double layer of cuff material 80 on the stent OD to aid in better sealing and tissue in-growth when pushed against native aortic root tissue.

Figure 44:
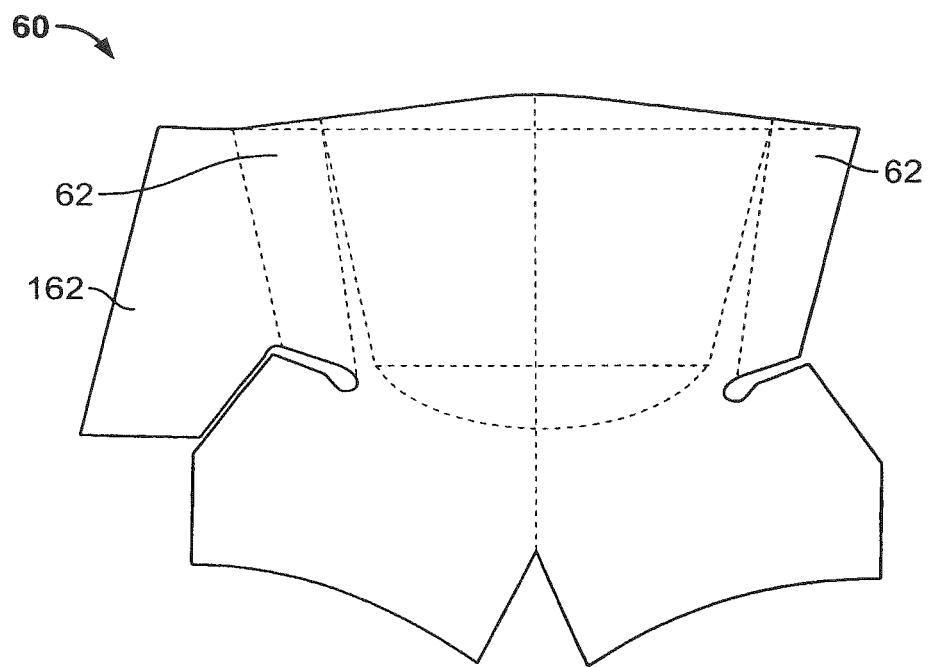
FIG. 44 is similar to FIG. 41B for another illustrative embodiment.

FIG. 44 shows a single leaflet design, with many of the same features as conveyed in FIG. 10, which can be applied to this stent design. The main difference is that one side flap 62 has an extension 162 that is used to seal the triangular-shaped opening.

Figure 45:
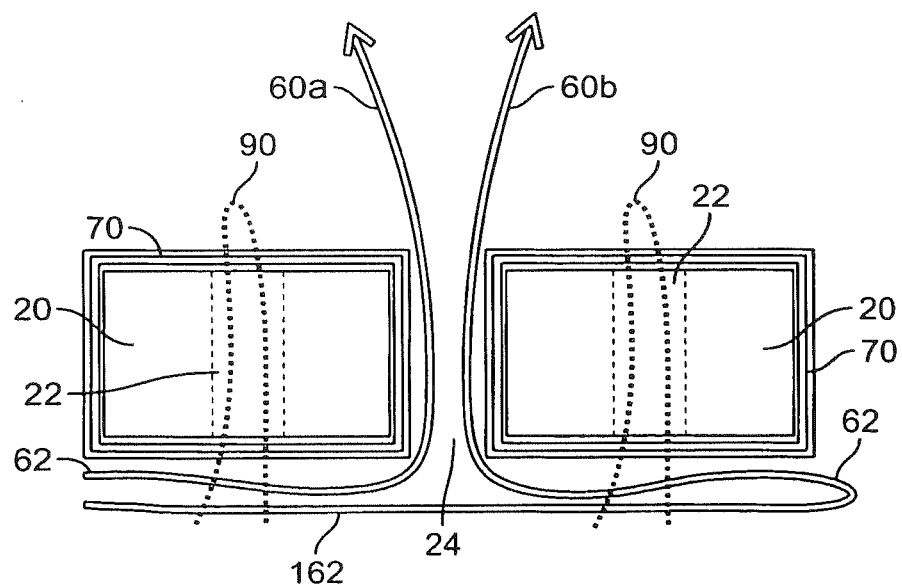
FIG. 45 is similar to FIG. 42 for another illustrative embodiment.

FIG. 45 shows one method for leaflet and ancillary component assembly. This is again similar to FIG. 42, and the same reference numbers are used for similar elements in both of these FIGS. Major features to note are as follows: (1) a buffering layer 70 between the stent 10 and the leaflets 60 reduces abrasion, (2) suture knots are on the OD of the post 20 so as not to interfere with leaflet movement/abrasion, (3) the gap 24 is large enough for leaflet thicknesses to eliminate post gapping, (4) the leaflets 60 attached to the OD of post 20 allow for stresses caused from blood flow back-pressure to be transferred to the stent frame 10 instead of point loads at suture attachments 90, and (5) the doubling back of the one leaflet at 162 aids in sealing the triangular stent post opening 24/28.

Figure 46:
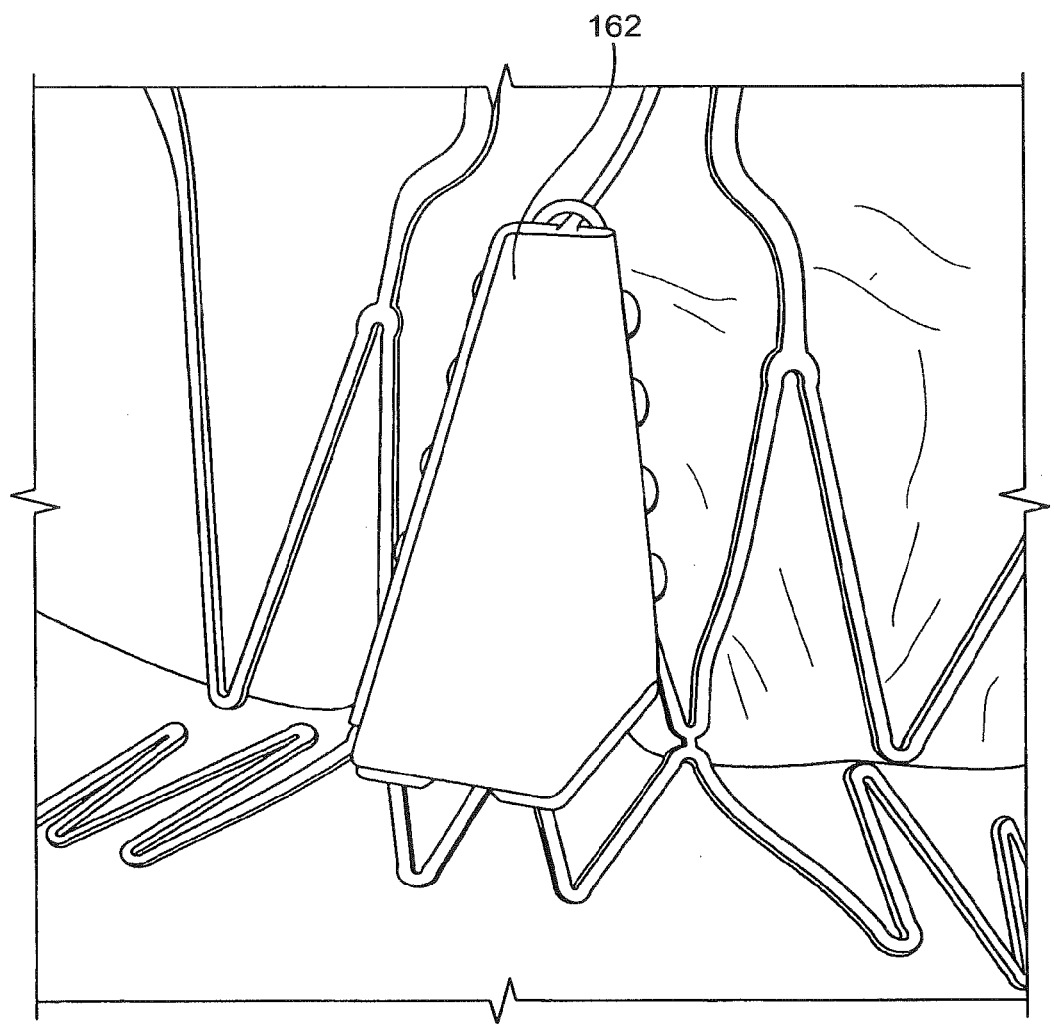
FIG. 46 is similar to FIG. 43 for another illustrative embodiment.

FIG. 46 shows an example of a single leaflet design with an enlarged triangular side flap 162 that is doubled back over itself to aid in sealing the triangular expanded post opening 24/28. FIG. 46 omits depiction of the sutures that are typically used to secure the leaflet and flap material to the stent frame.

Figure 47:
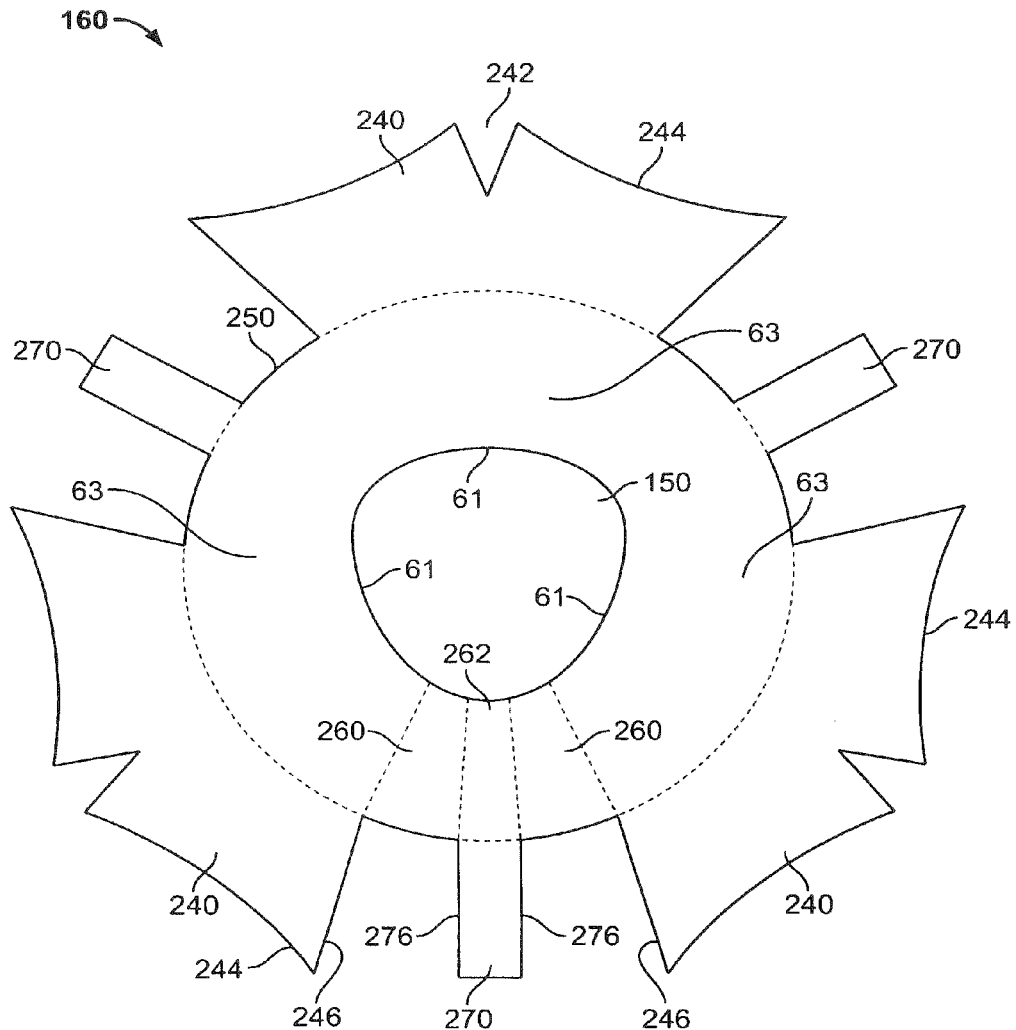
FIG. 47 is similar to FIG. 36 for another illustrative embodiment.

FIG. 47 shows a flat cutout of a continuous leaflet 160 with several features that aid in the attachment and sealing for an expanding post 20/24/28 design. Flaps 240 with triangular cutouts 242 are wrapped around the base of the stent 10. Edge 250 is sutured to the stent 10 to form the base of the leaflet belly. Edge 244 is secured around the base of the stent 10. Sections 260 are pulled through the triangular post opening 24/28, folded around the OD of the post 20, and doubled back on themselves. Sections 262 cover up the triangular openings 24/28. Flaps 270 extend toward the base of the stent to enhance sealing of covers 262 and are joined to the other flaps 240 along their edges 246 and 276. See the next FIG. for more detail.

Figure 48:
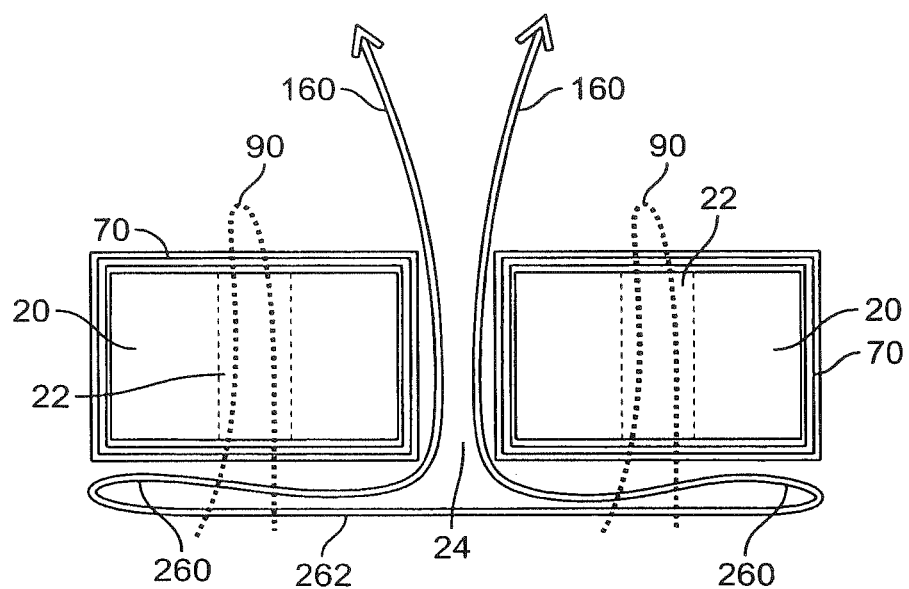
FIG. 48 is similar to FIG. 5 for another illustrative embodiment.

FIG. 48 shows one method for leaflet and ancillary component assembly. This is again similar to FIG. 45, and again uses the same reference numbers for similar elements. Major features to note are as follows: (1) a buffering layer 70 between the stent 10 and the leaflets 160 reduces abrasion, (2) the gap 24 between sides of the posts 20 at the upper apex of the triangular stent post opening is just large enough for leaflet thicknesses to eliminate post gapping at that location, (3) suture knots are on the OD of the post 20 so as not to interfere with leaflet movement/abrasion, (4) the leaflets 160 attached to the OD of post 20 allow for stresses caused from blood flow back-pressure to be transferred to the stent frame 10 instead of point loads at suture attachments 90, and (5) the leaflets 160 are fully sealed at the triangular commissures 20/24/28 as indicated at 262.

Figure 49:
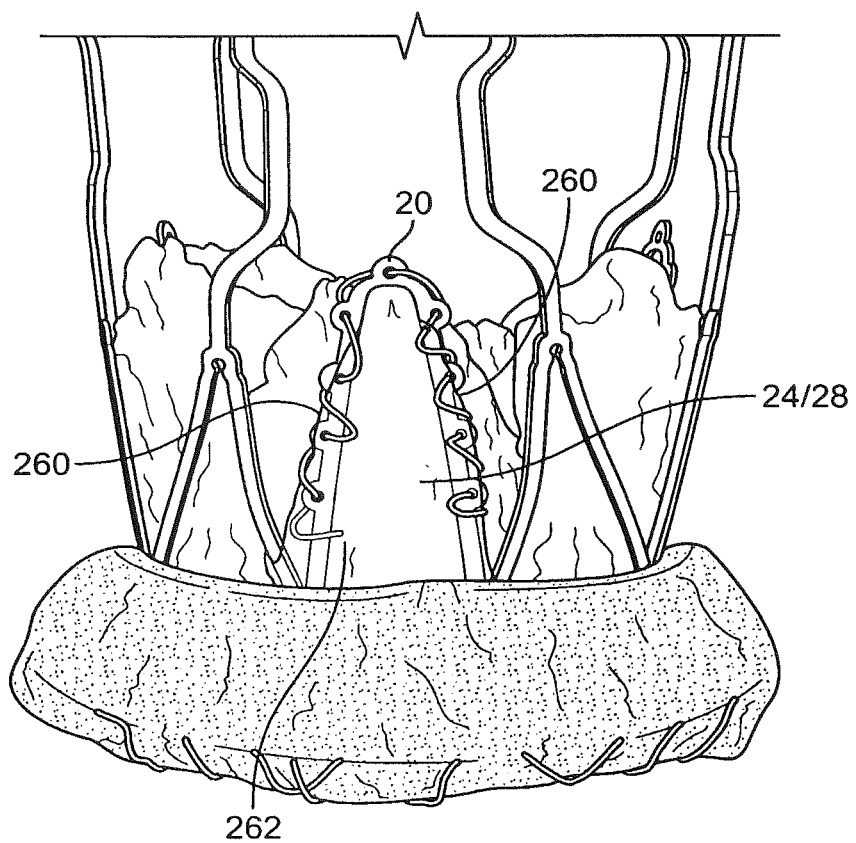
FIG. 49 is similar to FIG. 46 for another illustrative embodiment.

FIG. 49 shows an example of a single leaflet design doubled over itself at the edges 260 with a triangular section 262 in the middle to achieve a continuous tight seal.

Figure 50:
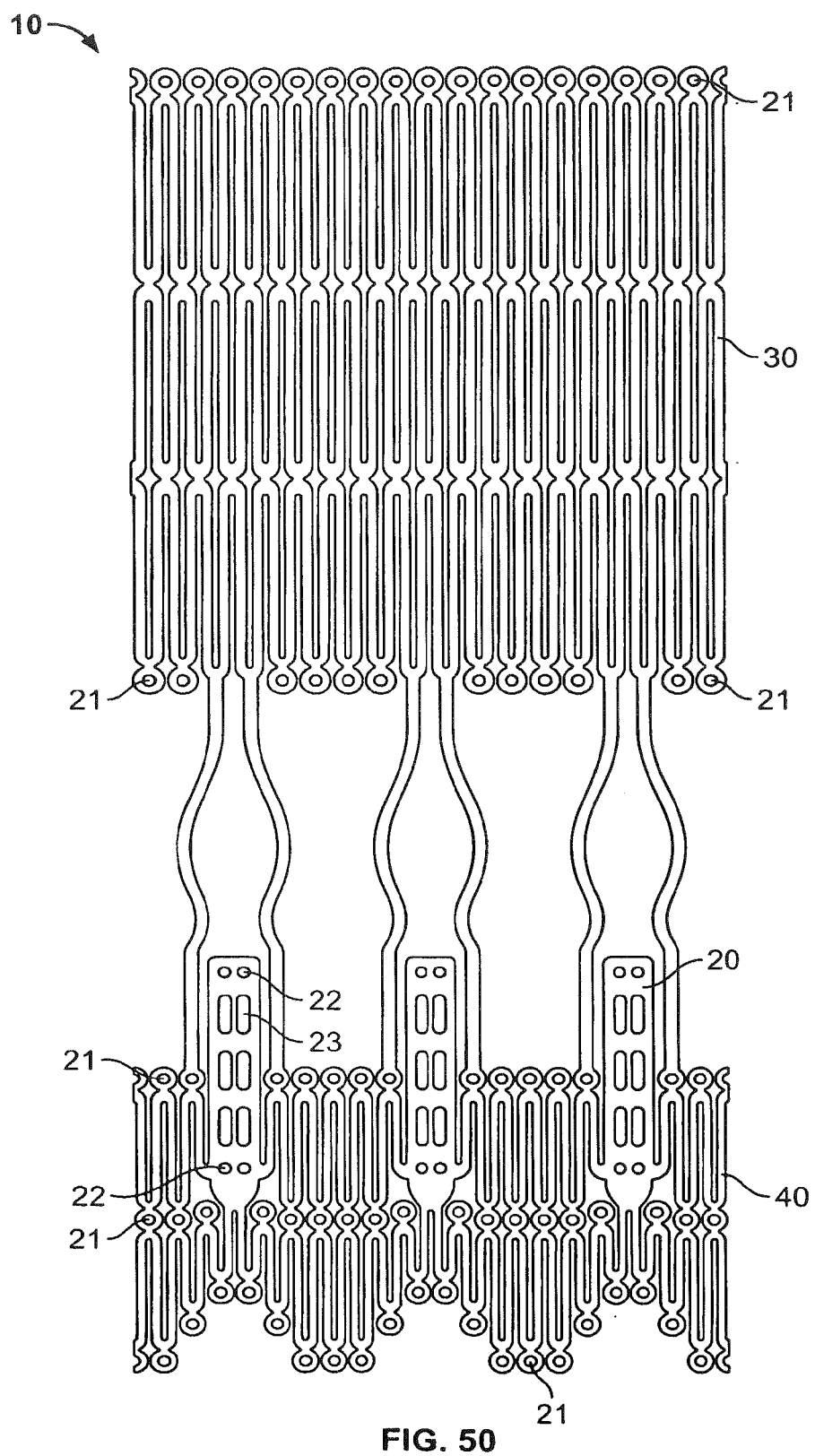
FIG. 50 is similar to FIG. 38A for another illustrative embodiment.
Figure 51:
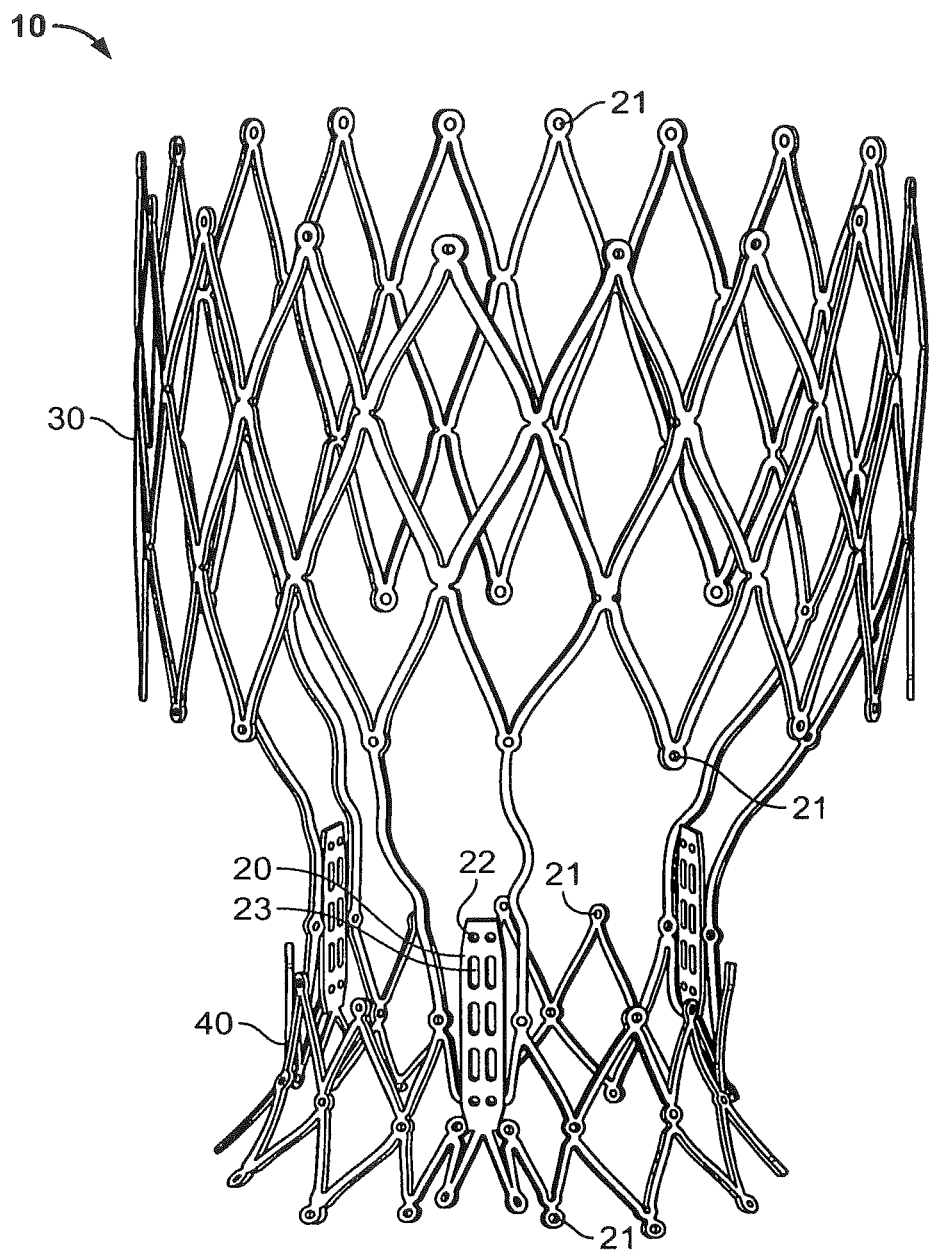
FIG. 51 is similar to FIG. 39 for another illustrative embodiment.

FIG. 50 shows further development of structures like those shown in FIGS. 5A and 5B. FIG. 50 shows a combination of eyelets 22 and slots 23 (already mentioned as a possibility earlier in this specification). The top and bottom post eyelets 22 anchor the leaflets 60 into position, and the slots 23 allow for easier assembly and multiple passes of a stitching needle. FIG. 50 shows the metal structure 10 in a flat or planar depiction and in its collapsed condition or configuration. Again, there is a combination of eyelets 22 and slots 23 on the commissure posts 20 for leaflet 60 attachment. Eyelets 21 in other areas can be variously used to attach leaflets 60, cuff material 80, and/or buffering material 70. FIG. 51 shows the FIG. 50 structure in its expanded state.

Figure 52:
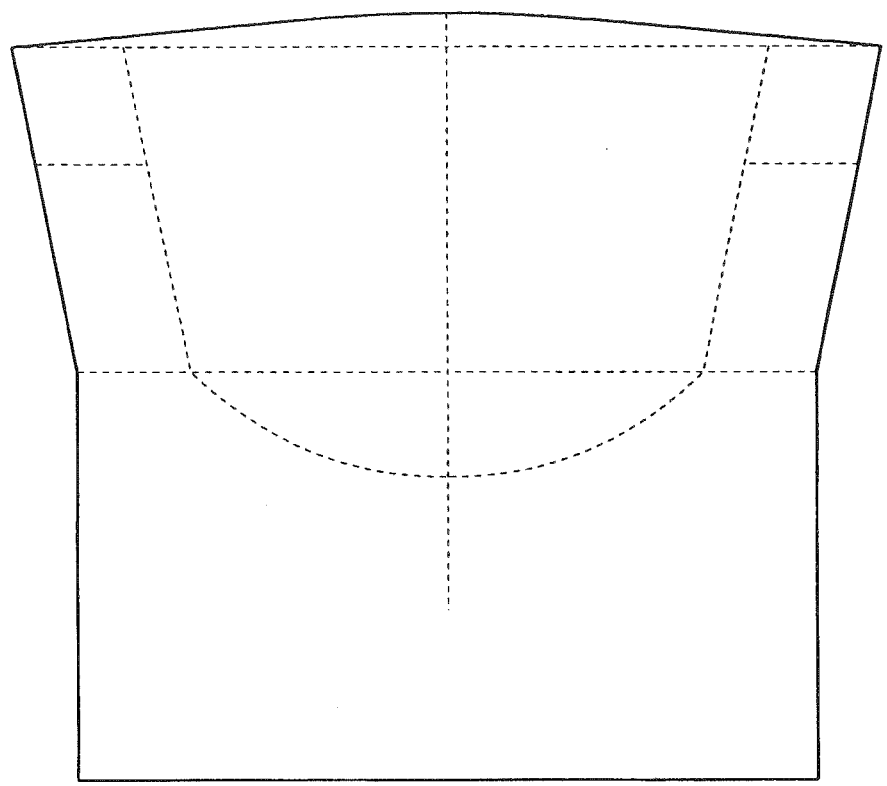
FIG. 52 is similar to FIG. 44 for another illustrative embodiment.

FIG. 52 shows an illustrative simplification of a single leaflet design of the general type that is shown in FIGS. 10 and 19. This simplified version allows the technician to assemble and trim the valve as needed, since there can be a variability in how the tissue behaves. This design also reduces the amount of openings to enhance sealing. The same principles apply as are discussed above in connection with FIGS. 10 and 19. Note also that this design can be used for FIGS. 10 and 19 valves, and then trimmed to the shape of the stent 10 if needed.

Figure 53A:
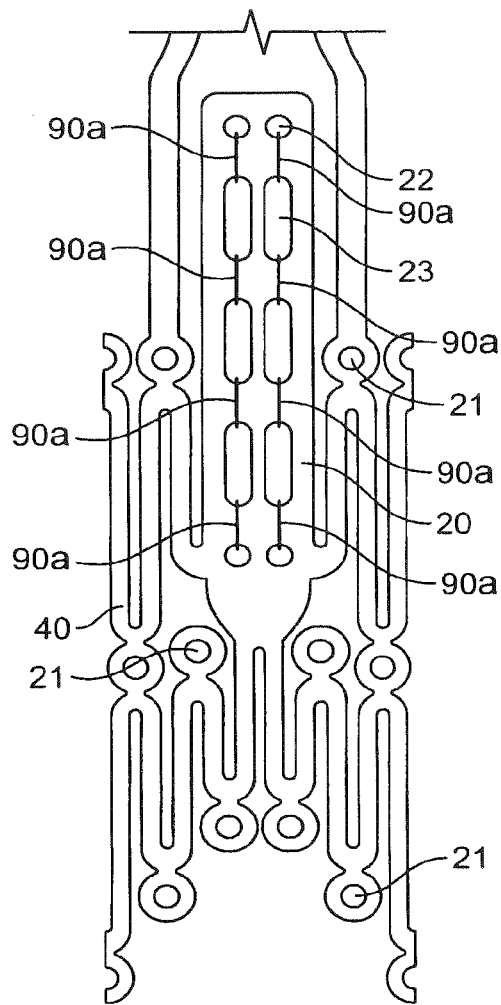
FIGS. 53A and 53B are each similar to FIG. 7 for other illustrative embodiments.
Figure 53B:
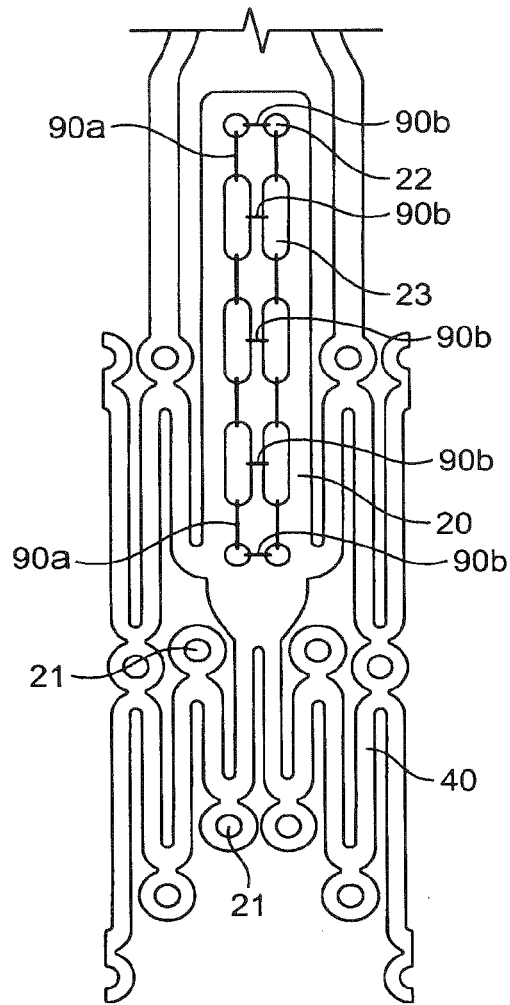

FIGS. 53A and 53B show further development of structures of the type that are shown in FIGS. 12A-C. In particular, FIGS. 53A and 53B show the front (outer diameter) view of a straight solid commissure post 20 and suture attachment 90a and/or 90b for leaflets 60. Note that these basic concepts can be used on the other post designs. FIG. 53A shows sutures 90a only looped around the stent material in the vertical direction. FIG. 53B shows sutures 90a in the vertical direction and sutures 90b in the horizontal direction, which is more indicative of what is shown in the top views of FIGS. 12A-C.

Figure 54:
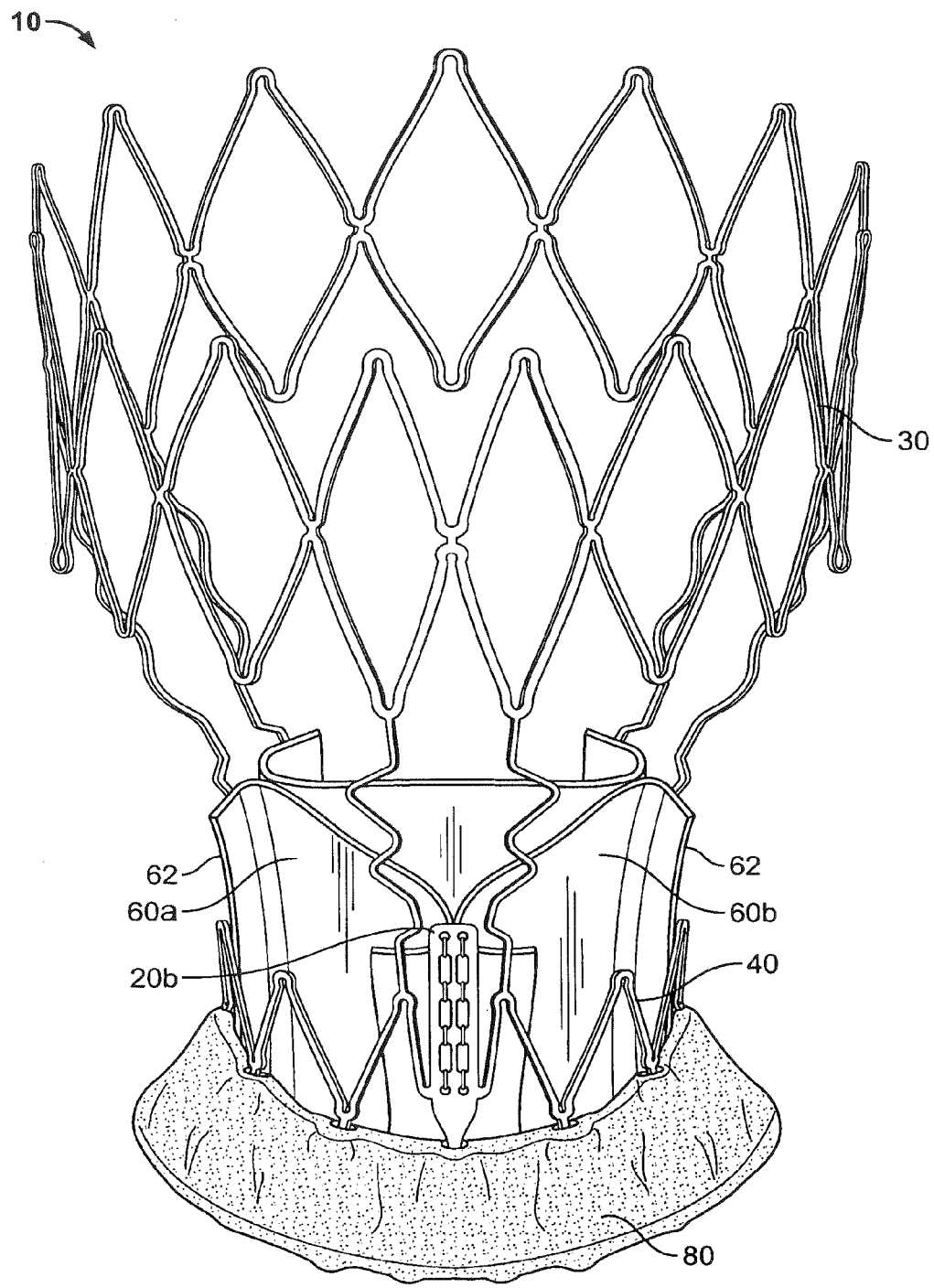
FIG. 54 is similar to FIG. 35A for another illustrative embodiment.
Figure 55:
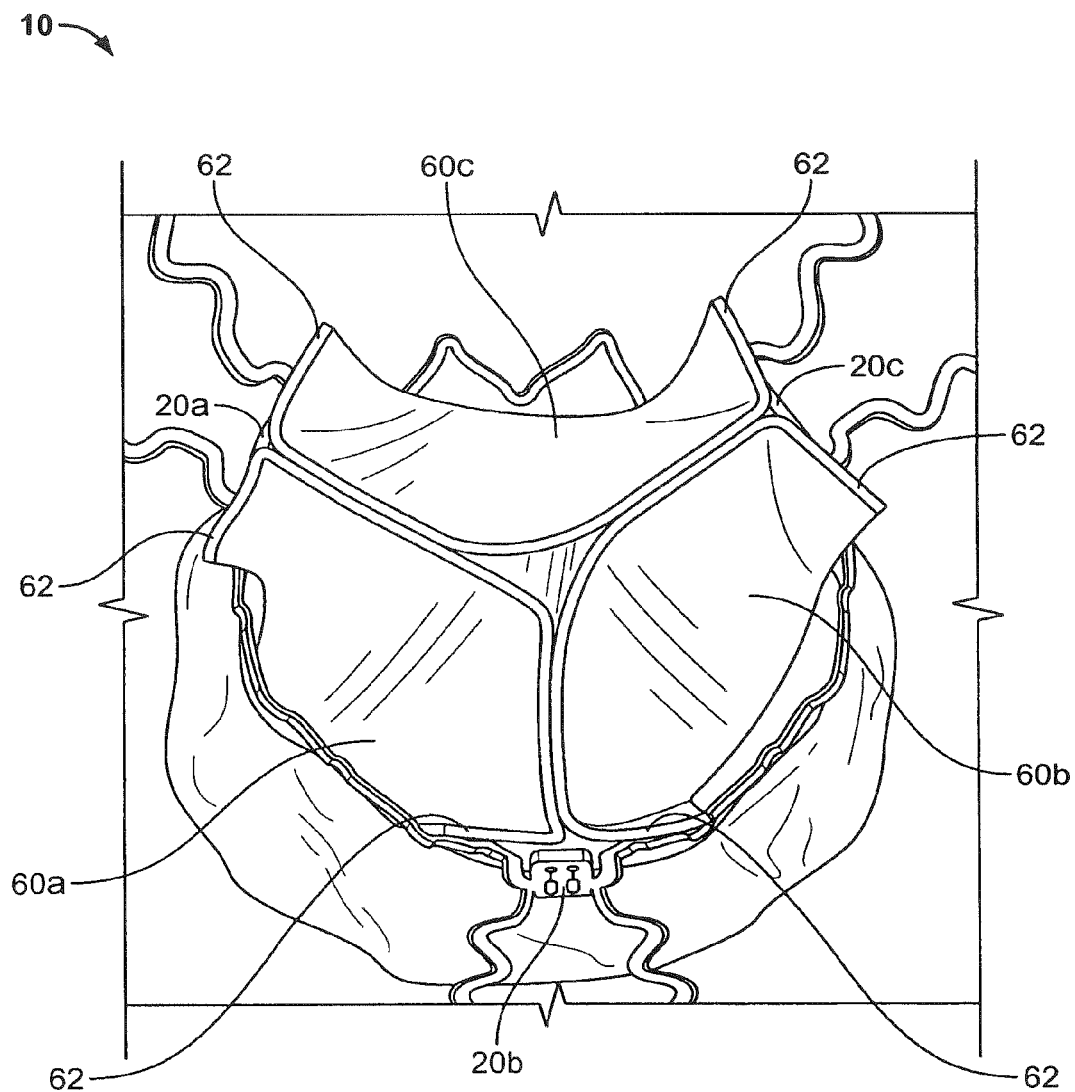
FIG. 55 is similar to FIG. 13 for another illustrative embodiment.
Figure 56:
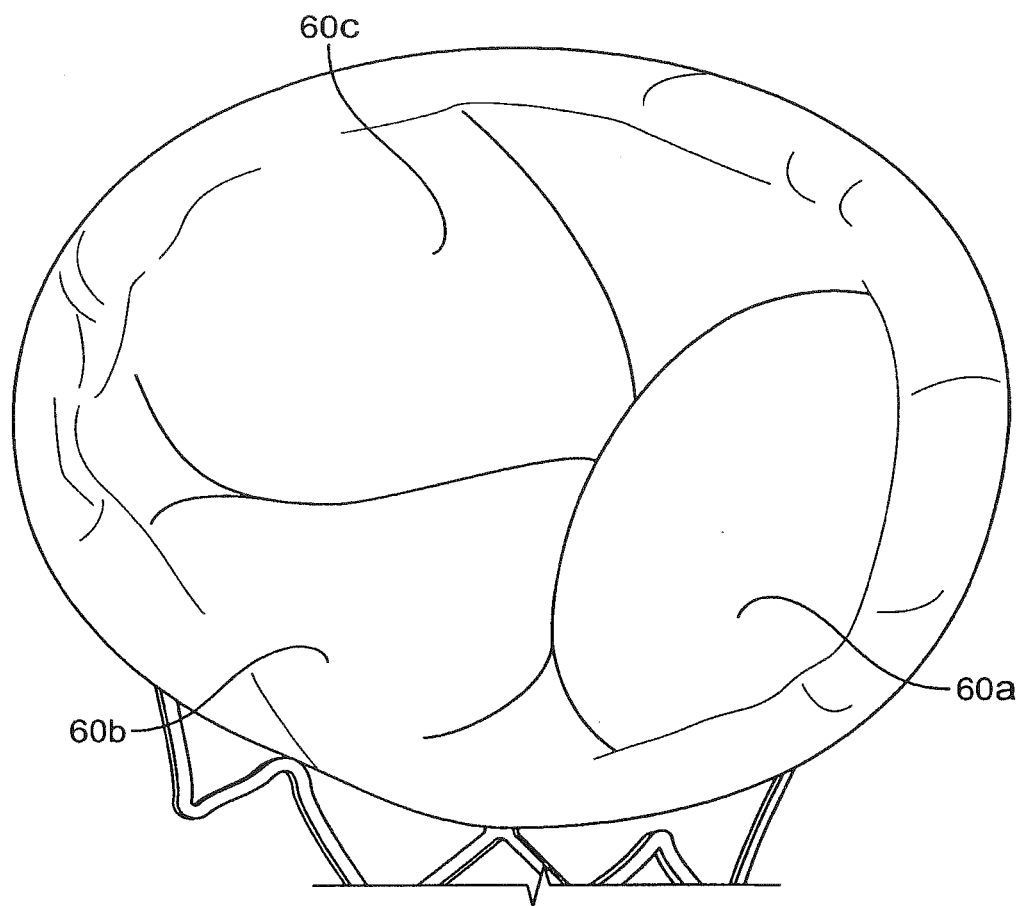
FIG. 56 is similar to FIG. 16 for another illustrative embodiment.
Figure 57:
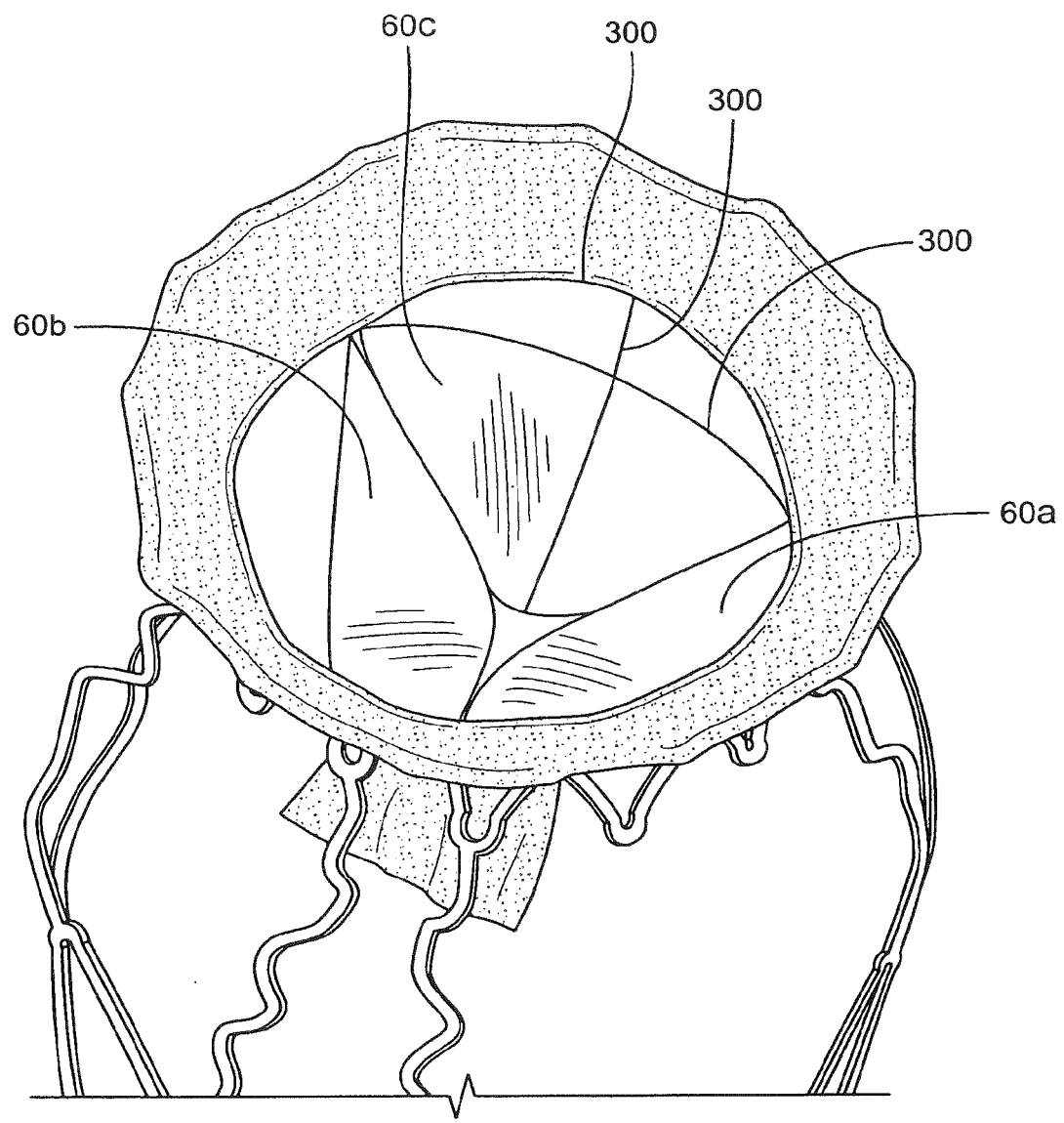
FIG. 57 is similar to FIG. 56 for another illustrative embodiment.

FIGS. 54-57 show further development of structures of the general type shown in FIGS. 13-16. FIGS. 54-57 are examples of modified stents 10 with tissue structures added. FIG. 54 is a side view of a valve with tissue leaflet 60 attachment like FIG. 53A. FIG. 55 is a top view similar to FIG. 13, but with tissue leaflets 60. FIG. 56 is a bottom view with leaflet tissue wrapped around the bottom edge. (This leaflet tissue may also be over other layers of fabric and/or buffer material, depending on the design of the valve.) FIG. 57 is a bottom view with tissue terminated at the bottom edge. Note also that the traces 300 for the leaflet shape are shown. These traces 300 can be temporary (or permanent) markings on the leaflet material to help the assembly technician properly shape and assemble the valve.

Figure 58:
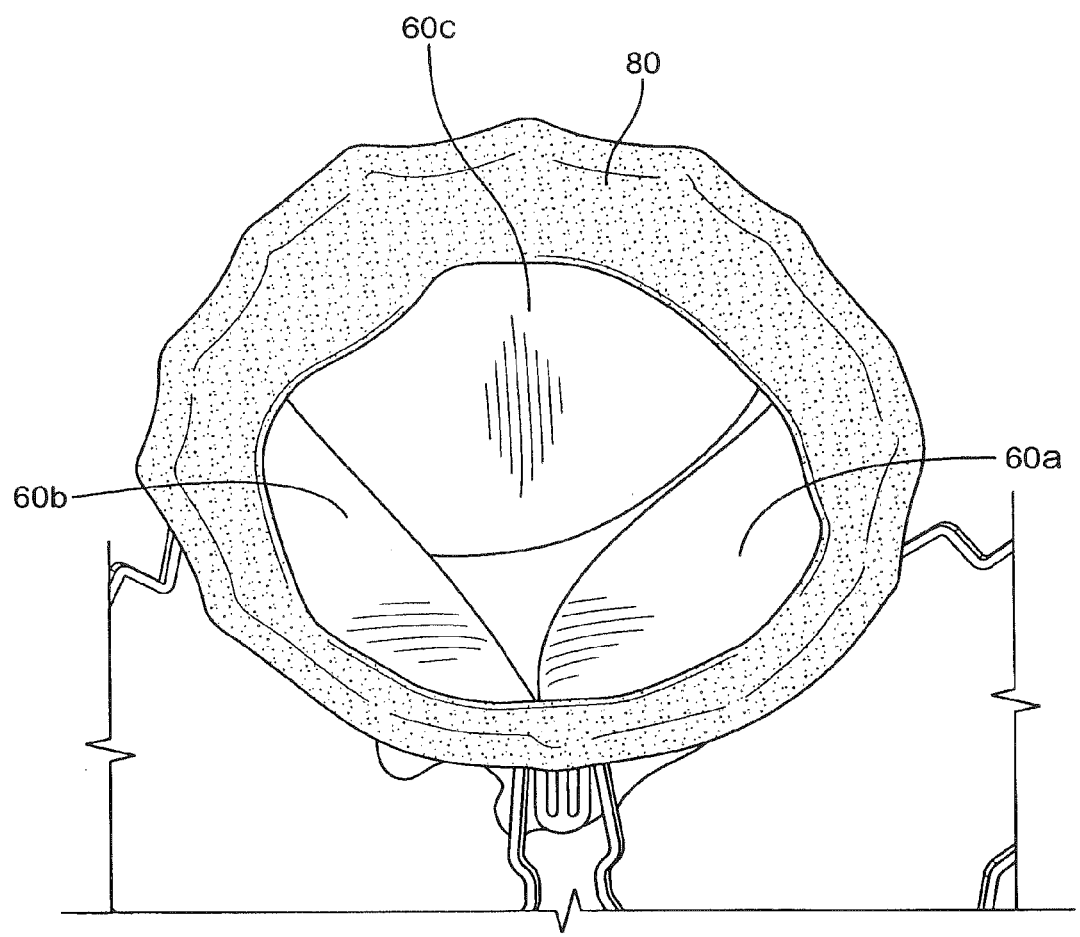
FIG. 58 is similar to FIG. 57 for another illustrative embodiment.
Figure 59:
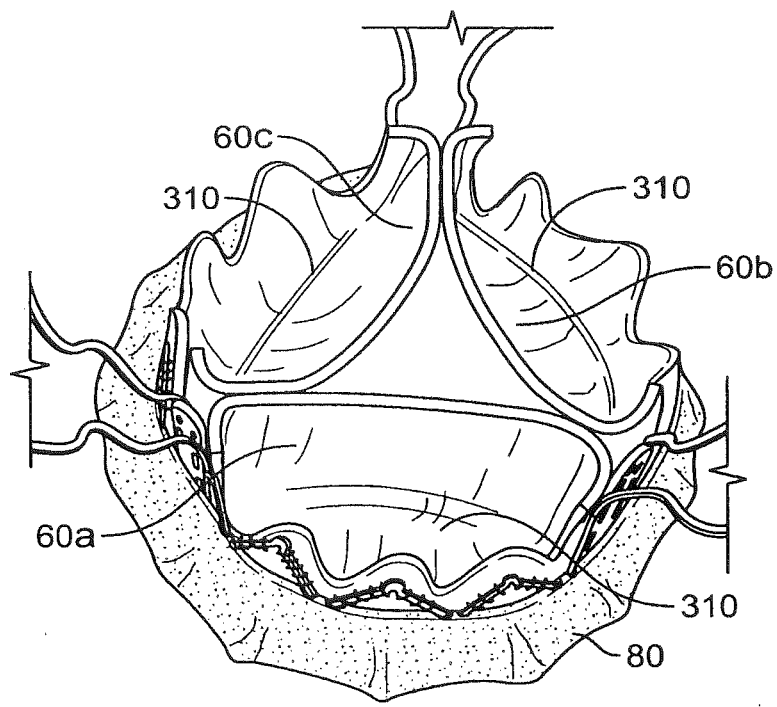
FIG. 59 is similar to FIG. 55 for another illustrative embodiment.
Figure 60:
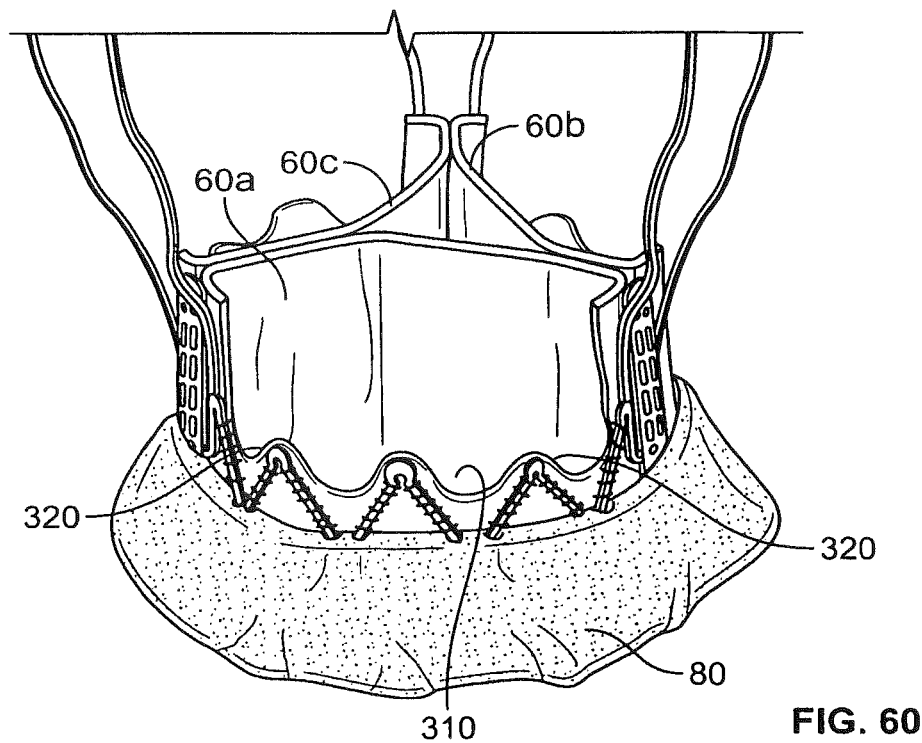
FIG. 60 is similar to FIG. 54 for another illustrative embodiment.

FIGS. 58-60 show further development of structures like those shown in FIG. 20. FIGS. 58-60 show valves built with this concept to further clarify how the valve actually looks. FIG. 58 is a bottom view of leaflets folded to form pockets when the free edges of the leaflets are coapting. FIG. 59 is a top view showing continuous pockets 310. FIG. 60 is a side view showing continuous pockets 310 and the rolled up leaflets trimmed to the outline of the stent at 320. Buffer and cuff material can also be shaped to outline the contour of the expandable stent portion.

Figure 61:
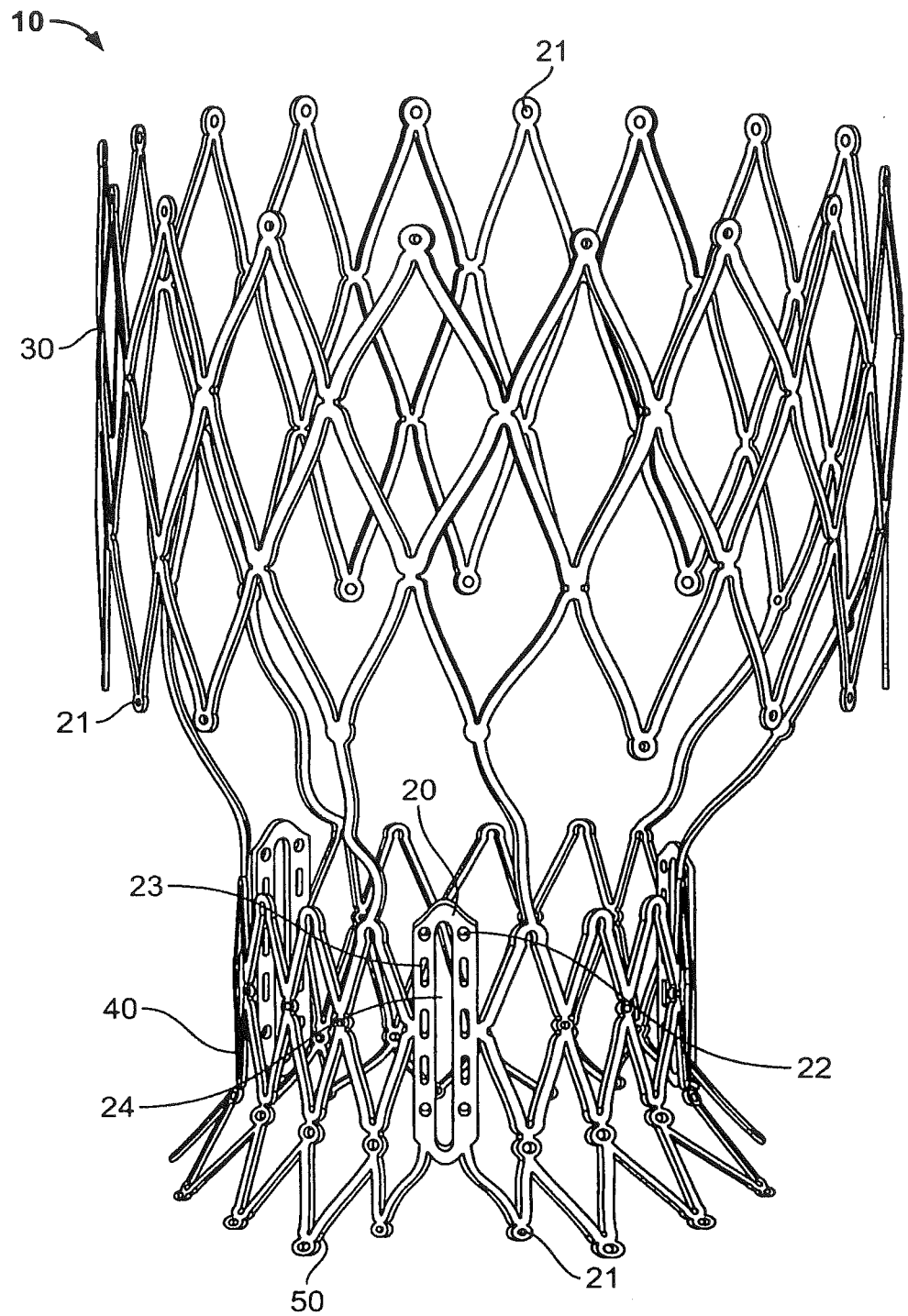
FIG. 61 is similar to FIG. 51 for another illustrative embodiment.

FIG. 61 shows further development of structures like those shown in FIGS. 30 and 31. FIG. 61 shows a further developed version of a nitinol part (stent) 10 that has been expanded. This design also incorporates eyelets 22 and slots 23, as well as eyelets 21 in various locations around the stent for attachment. Note that this design also has an extra row of closed-perimeter, open-centered, circumferentially collapsible/expandable cells on the bottom section 40/50 as compared to the earlier examples.

FIG. 62 shows a single leaflet shape 60 which may have several advantages. For example, as compared to some leaflet shapes described earlier in this specification, the FIG. 62 shape can reduce the amount of leaflet tissue that needs to be collapsed when the prosthetic valve is collapsed. This can help the prosthetic valve collapse to a smaller size for less invasive delivery into a patient. This leaflet shape can also help to redistribute high stress areas in the base of the valve belly where tear-out might otherwise tend to occur. All of these modifications can improve valve function and durability.

As in some earlier-described embodiments, lines 300 are indicator lines on leaflet 60 to help with assembly of the leaflet into a prosthetic valve. In addition, some of these lines serve to demarcate certain portions of the leaflet in the following discussion. Line 300a-b is a line along which leaflet material outside the line can be folded in on leaflet material inside the line. Especially line 300b is also a line along which the base of the leaflet may be sutured to other structure of the valve. For example, this may result in securing the base of the leaflet through cuff material 80 of the valve. This arrangement helps to distribute stresses at the base of the leaflet (e.g., in the area indicated generally by reference number 400) upwardly along curve 300b (e.g., into the areas indicated generally by reference number 410) to spread out these stresses and prevent them from concentrating right at the leaflet base. For example, FIG. 64 shows how leaflet material 62b outside indicator line 300b may be folded up outside the remainder of a leaflet 60. This produces a doubled-over layer of leaflet material, which can be sutured through (including to other structure of the valve) using sutures 90 to improve durability.

Returning to FIG. 62, and also now referring to a representative prosthetic valve commissure post 20 as shown in FIG. 63 for use with the FIG. 62 leaflet, leaflet flap portion 62a may be positioned relative to post 20 so that portion 62a sits above the top-most horizontal eyelet 23a in post 20. Leaflet flap portion 62c is then positioned between horizontal eyelet 23a and the top-most vertical eyelet 23d in post 20. Below flap section 62c is a further leaflet flap section 62d, which is positioned for attachment (e.g., via sutures) to three vertical eyelets 23d in the upper portion of stent post 20. Dotted line 420 in FIG. 63 indicates the approximate boundary of leaflet flap portion 62d when thus secured to post 20. The area of post 20 below eyelets 23d can be used as additional area for, e.g., cuff 80 attachment, hiding suture knots, and other features.

As compared to some earlier-described leaflet embodiments, the FIG. 62 leaflet can include less leaflet material outside indicator line 300b. As noted earlier, this can help reduce the amount of leaflet material in the valve and thereby facilitate collapsing the valve to a smaller circumferential size.

Figure 65:
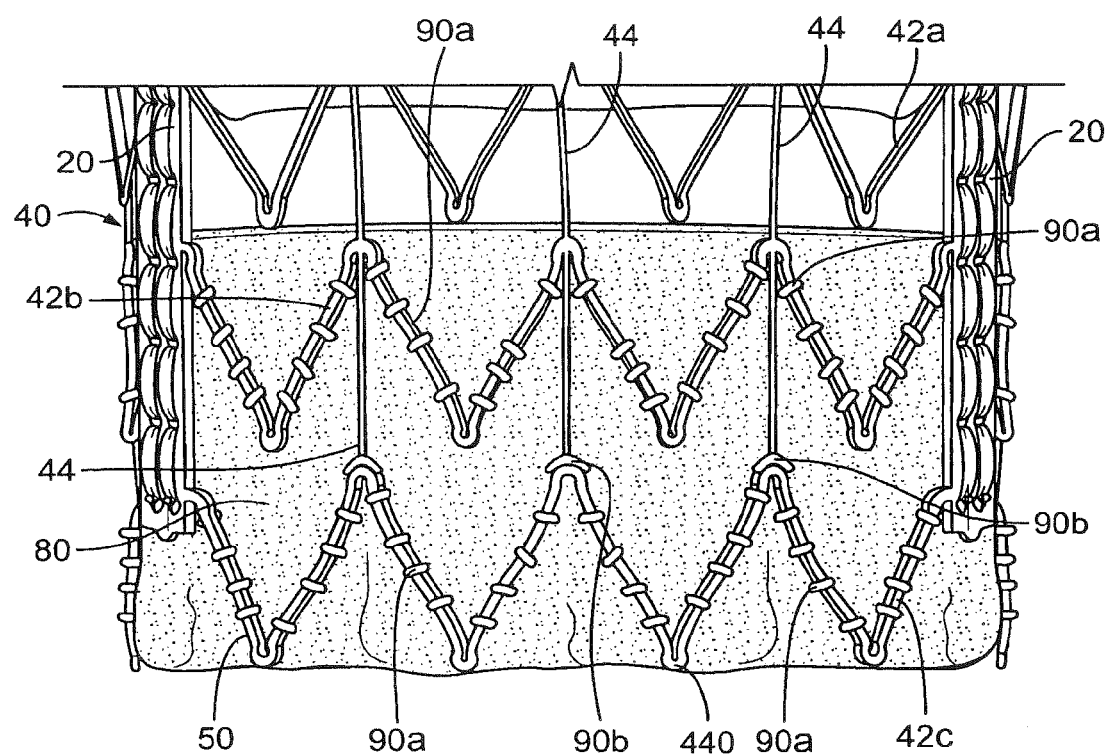
FIG. 65 is a simplified, partial, elevational view of an illustrative embodiment of an assembly of several components in accordance with the invention.

Turning now to another consideration that may be important in construction of prosthetic heart valves in accordance with the invention, when a leaflet 60 is secured through cuff material 80, it may be desirable to ensure a durable securement of the leaflet with reduced movement that could lead to cuff/suture/leaflet abrasion. Termination of a cuff 80 (especially when the stent is flared outward as at 50 in some embodiments herein) can be difficult. FIG. 65 and several subsequent FIGS. show structures that can help to address these issues.

As shown in FIG. 65, cuff 80 is secured by outlining the struts of the cells that form stent portions 40 and 50 with whip stitch sutures 90a. In addition, stent portions 40 and 50 are constructed so that they include several annularly extending serpentine, undulating, or zig-zag members 42a-c that are connected to one another by vertical bars 44. Serpentine members 42a-c annularly compress or expand to allow the prosthetic valve to circumferentially collapse or expand. But vertical members 44 do not change length during such annular compression or expansion of the serpentine members. This helps to reduce the amount by which the prosthetic valve changes axial length during circumferential compression or expansion. This in turn can help reduce any tendency of cuff 80 to shift relative to stent portion 40/50. Vertical bars 44 can also be secured to cuff 80 by suture stitches 90b. In this example, cuff 80 and buffer material (hidden between the fabric of cuff 80 and leaflets 60) are mounted in the inside diameter ("ID") of the stent and can extend any distance up or down the height of the stent frame. (Although FIG. 65 shows all of components 20, 42, and 44 one-piece with one another, some or all of these components may initially be separate from one another and then assembled with the other components.)

Figure 66:
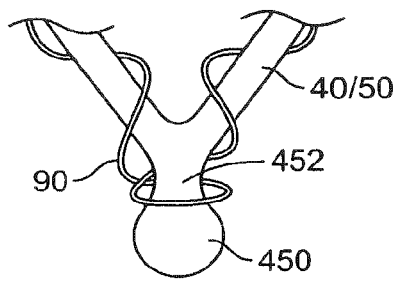
FIG. 66 is a simplified elevational view of an illustrative embodiment of a portion of a structure like that shown in FIG. 65 in accordance with the invention.
Figure 67:
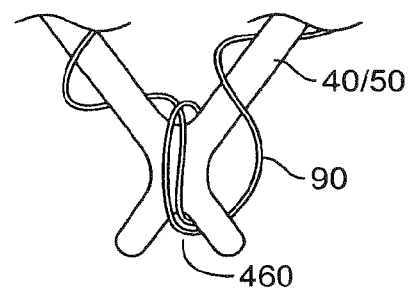
FIGS. 67, 68A, and 68B are each similar to FIG. 66 for other illustrative embodiments.

In addition to the above, the invention can address possible difficulty in firmly securing cuff 80 to stent cell ends. For example, especially when stent portion 40 is flared as at 50, the adjacent cuff material 80 may have a tendency to slip vertically along the stent when a leaflet 60 is secured to the cuff material and under load. Reference number 440 in FIG. 65 points to a representative location where this may be an issue. Passing a suture through an eyelet 91 at such a location 440 can help prevent material slip. FIGS. 66-68 also show several others shapes that can be provided at the top and/or bottom of stent cells to help secure the cuff 80 to the stent more securely. For example, FIG. 66 shows providing an enlarged knob 450 on the end of a representative stent cell 40/50. Knob 450 is connected to the stent cell by a small neck region 452. Suture material 90 can be wound around neck 452 as shown in FIG. 66 to help prevent any other material that is secured to the stent by suture 90 from moving upwardly (in this example) away from the depicted stent cell end.

As another example, FIG. 67 shows a notch 460 in the stent material, which notch opens away from the associated stent cell end 40/50. Suture material 90 can pass (repeatedly) from the stent cell end through notch 460 and back into the stent cell end to ensure that the suture (and anything secured by the suture) cannot shift upwardly (in this example) relative to the stent cell end.

Figure 68A:
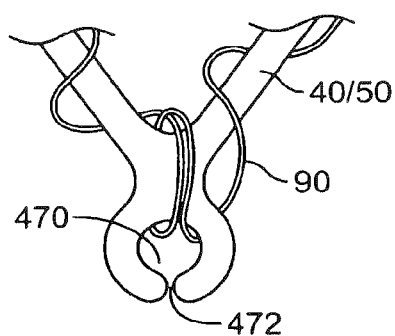

As still another example, FIG. 68A shows a partially formed eyelet 470 at the end of a stent cell 40/50. Eyelet 470 is large enough for suture material 90 to pass through, but it may not be large enough for the suture needle to pass through. However, suture material 90 can be pulled into eyelet 470 through the open side 472 of the eyelet (which open side faces away from the apex or end of stent cell 40/50). Suture material 90 may pass (repeatedly) from inside stent cell 40/50 through eyelet 470 and back into stent cell 40/50 in a loop, FIG. 8, or other pattern to secure suture 90 and any other material (such as cuff 80) that is engaged by suture 90 to the end of the stent cell. Again, as in the case of the structures shown in FIGS. 66 and 67, this is done in such a way that other material (such as cuff 80) that is secured by suture 90 cannot move upwardly (in this example) relative to the end of stent cell 40/50.

Figure 68B:
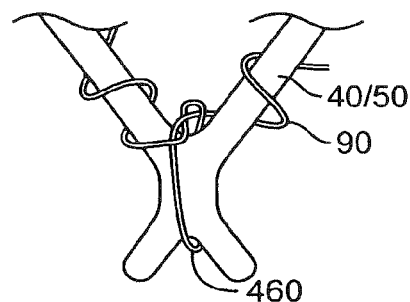

FIG. 68B shows an alternative to FIG. 67 in which the suturing 90 is interlocked with itself as part of passing through notch 460. The interlocking shown in FIG. 68B can also be used with other stent frame shapes such as the shape shown in FIG. 68A.

Figure 69A:
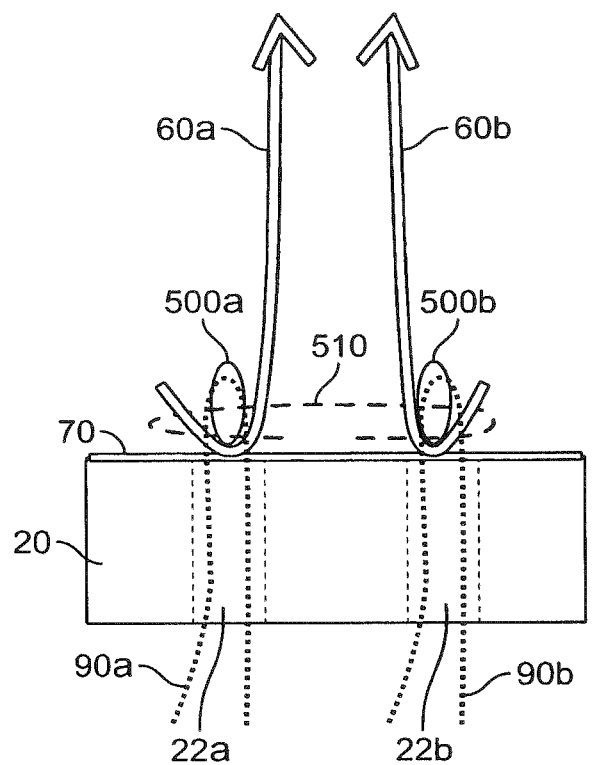
FIGS. 69A and 69B are each similar to FIG. 48 for another illustrative embodiment.
Figure 69B:
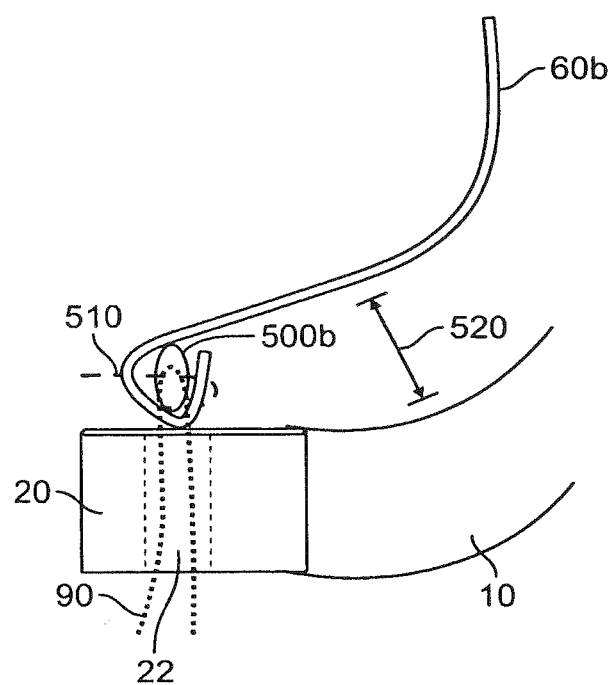

FIG. 69A shows a possible modification of a structure like that shown in FIG. 12B. In this alternative a reinforced core 500a or 500b lines the creased area that the flaps of leaflets 60a and 60b are folded around. The core material 500a/b can be other tissue, polymer, metal, and/or fabric. The flap of the leaflet 60a or 60b is sutured (90a or 90b) through the stent 20 in a manner similar to what has already been shown. The flaps of the leaflets 60a and 60b can be additionally wrapped around the core(s) 500a/b and secured via additional suturing 510 to form a bundle. This may add more reinforcement from tissue tears and may also mitigate leaflet abrasion as illustrated by FIG. 69B. By binding the leaflet (e.g., 60b) and core (e.g., 500b), the leaflet is not allowed to open all of the way up to hit the frame 10 of the stent. In other words, a clearance like that indicated by double-headed arrow 520 in FIG. 69B is maintained.

Figure 70:
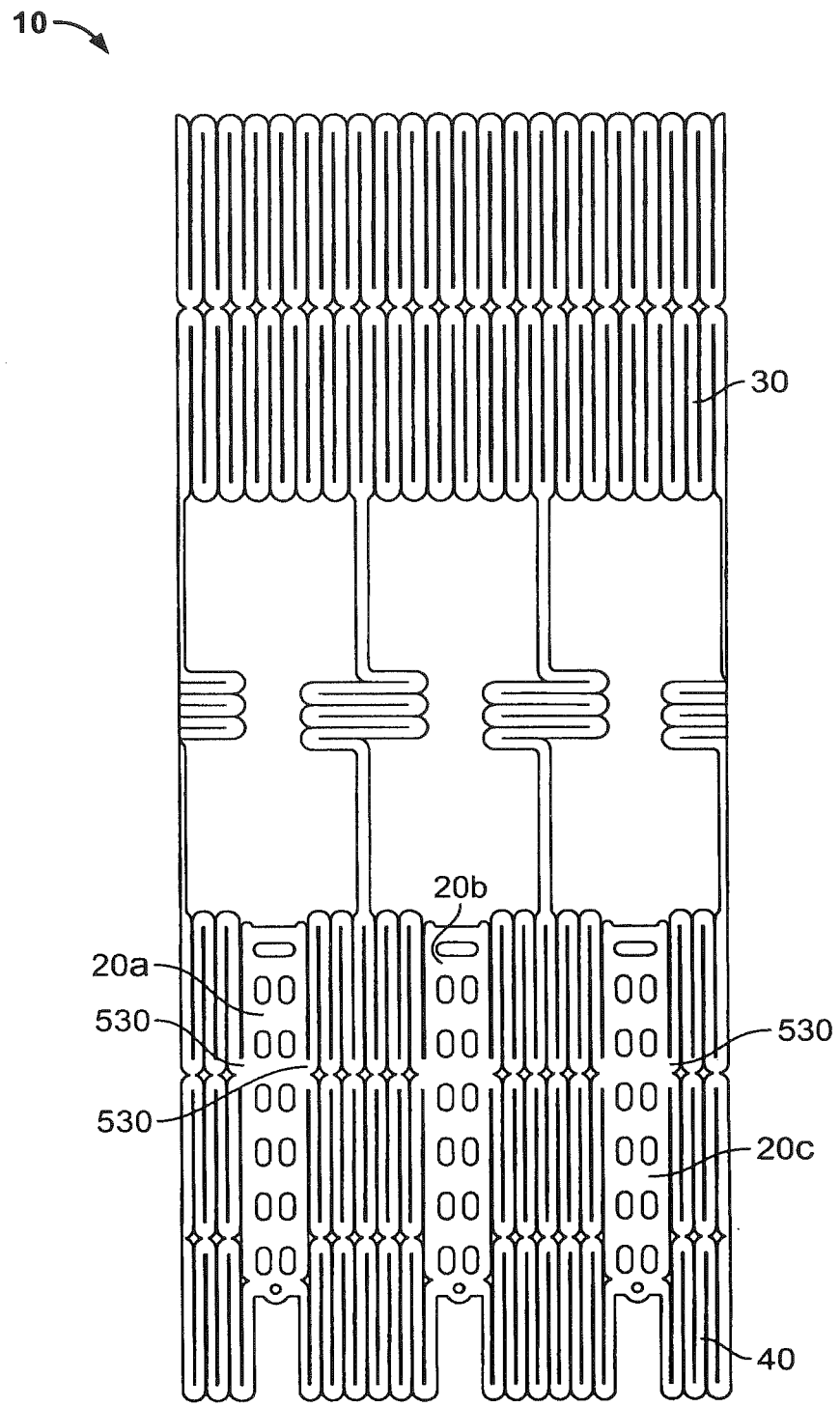
FIG. 70 is similar to FIG. 50 for another illustrative embodiment.

FIG. 70 shows an example of a self-expanding stent design with the downstream-most connections 530 between commissure posts 20 and the remainder of annulus portion 40 more than 50% up the post height in the direction of blood flow through the implanted valve. This means that in this embodiment the posts 20 are less cantilevered than in some other embodiments. This design still retains the ability to attach the leaflets to other structure of the valve in ways similar to what has been described for other embodiments.

Figure 71:
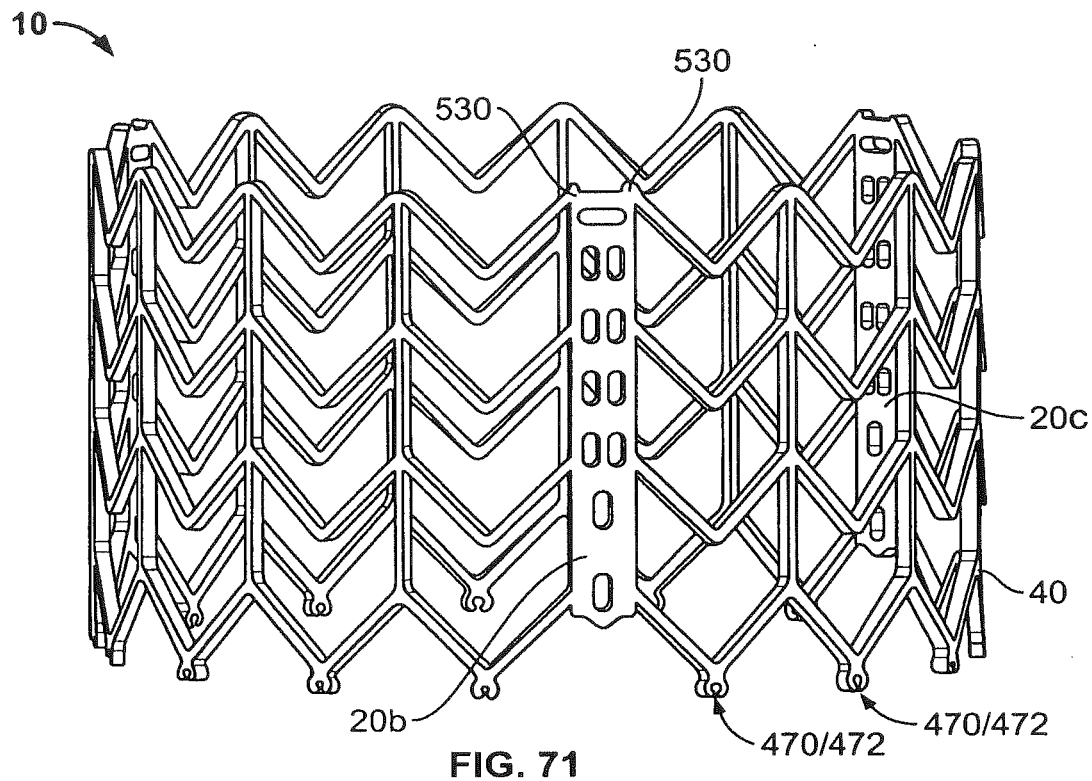
FIG. 71 is similar to FIG. 61 for another illustrative embodiment.

FIG. 71 shows an example of a balloon-expandable stent design with the downstream-most connections 530 between each stent post 20 and the remainder of the stent 10/40 all the way up to the top of the posts 20. FIG. 71 shows stent 10 in its fully expanded state. This design still retains the ability to attach the leaflets of the prosthetic valve to other structure of the valve in ways that are similar to what is shown and described for other embodiments. The FIG. 71 stent includes attachment structures 470/472 at the base of the stent that are similar to what is shown in FIG. 68. These can also be used as interlocks for attachment of the prosthetic valve to a delivery system for that valve.

Figure 72:
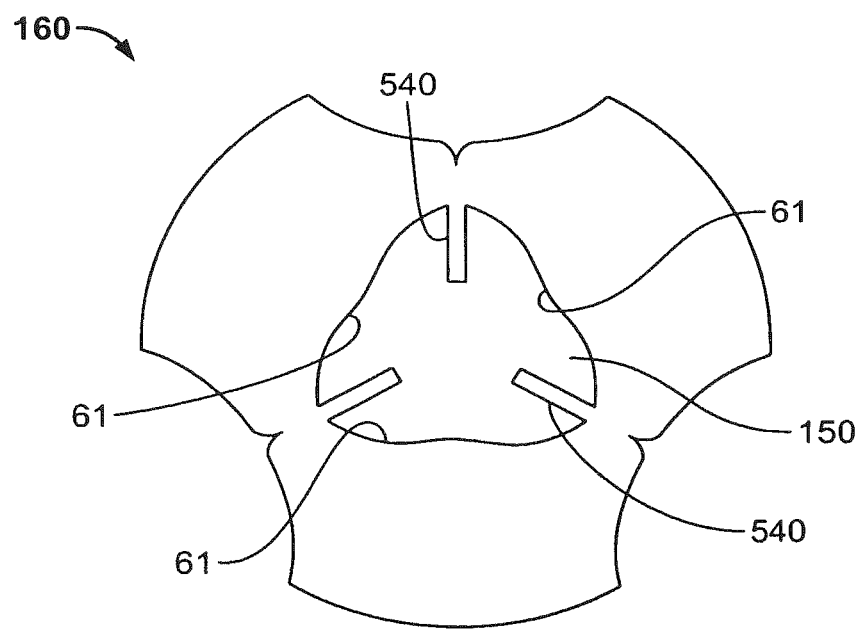
FIG. 72 is similar to FIG. 47 for another illustrative embodiment.

FIG. 72 shows another example of one continuous sheet 160 of leaflet material that can be shaped (when attached to a valve stent, etc.) to provide all three leaflets of a valve. FIG. 72 thus shows an alternative to what is shown in other FIGS. like FIG. 21. This continuous design has flaps 540 built in to attach to the tops of the commissure posts 20 as described elsewhere in this specification. Another difference is radially inward contour or bulge of the free edge 61 of what will be each leaflet. This bulge gives the leaflets additional coaptation when the valve is closed.

Figure 73:
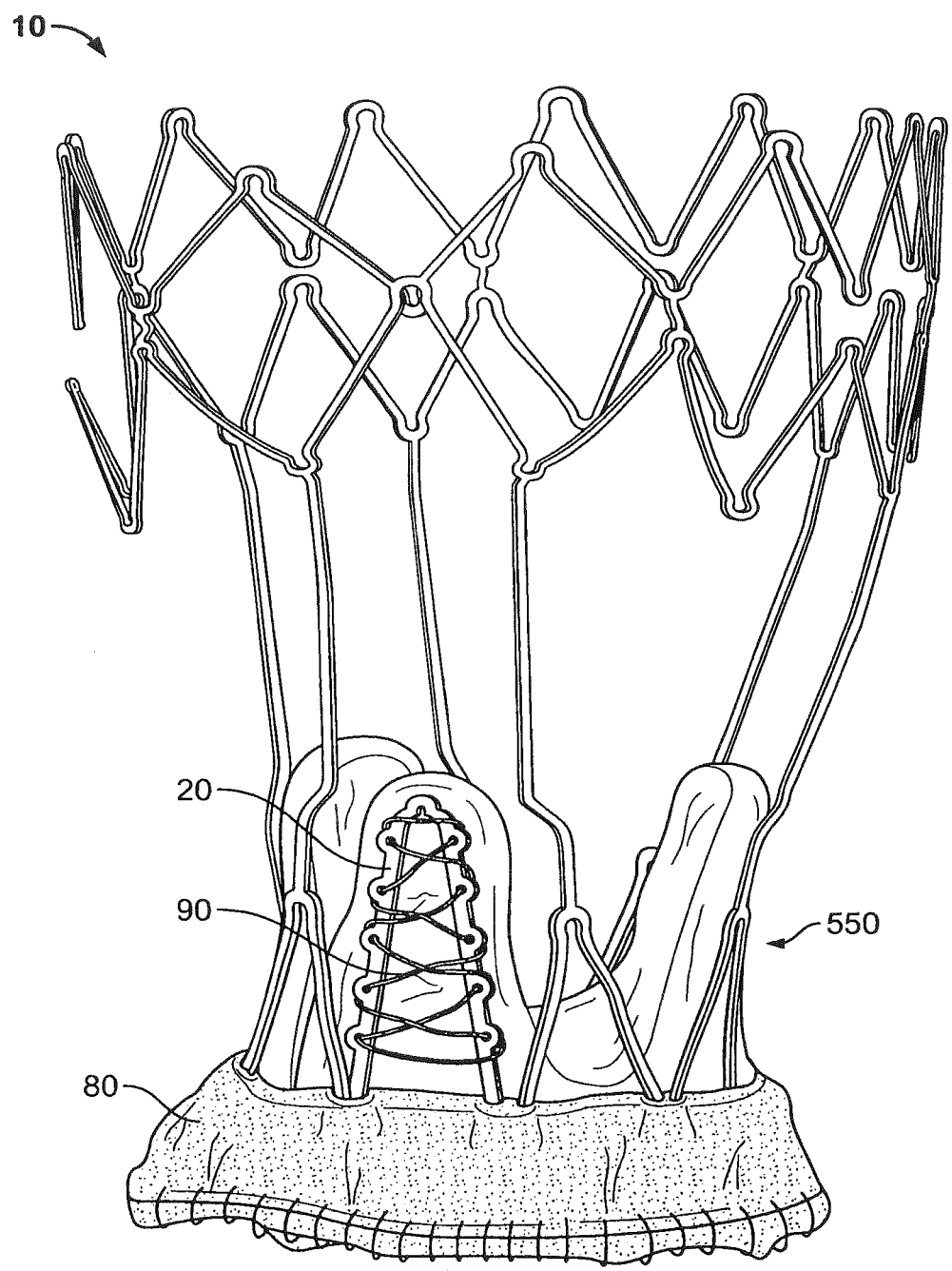
FIG. 73 is similar to FIG. 65 for another illustrative embodiment.

FIG. 73 illustrates the point that several of the principles of this invention can be applied to collapsible and re-expandable prosthetic valves that use leaflets that are not just from sheet material. For example, a bovine jugular or porcine aortic root (or individual leaflets) 550 can be attached to the commissure posts 20 of a valve stent. In other words, in the prosthetic valve shown in FIG. 73, the valving action is provided by the inclusion of an intact tissue valve (or leaflet cusps) 550 taken from an animal.

Figure 74A:
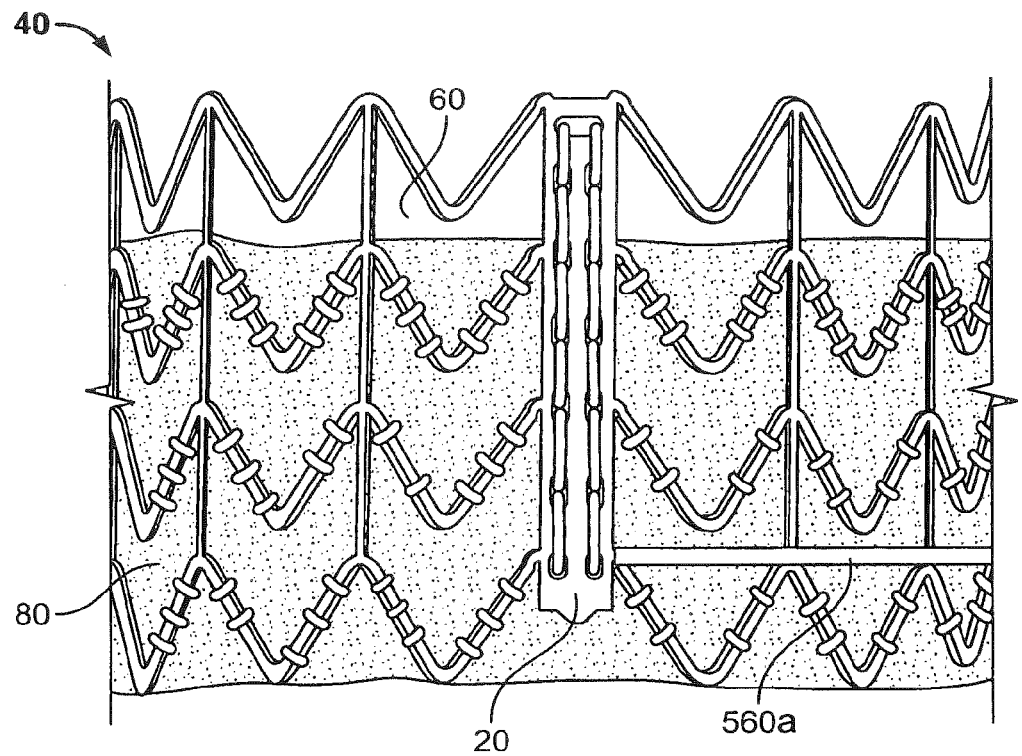
FIGS. 74A-C are each similar to FIG. 65 for other illustrative embodiments.
Figure 74B:
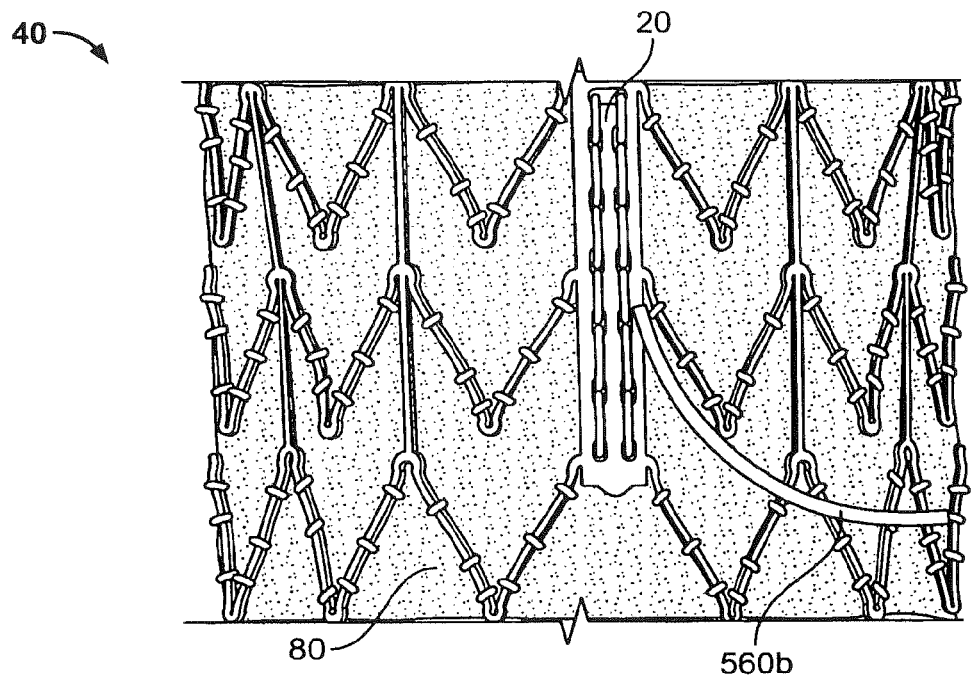
Figure 74C:
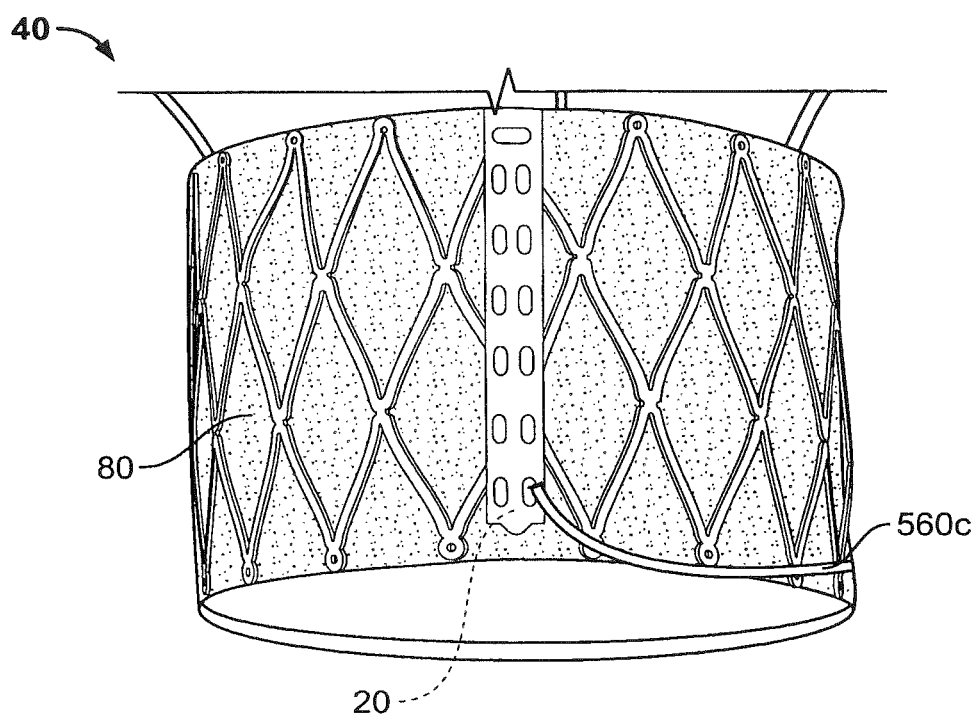

FIGS. 74A-C show several illustrative variations on what is shown in FIG. 65. For example, in FIG. 74A reference line 560a indicates the contour of one representative leaflet where it is attached (near its bottom or upstream portion) to the cuff 80 of the valve. (Apart from reference line 560a, FIG. 74A omits leaflets 60 and does not attempt to show the rear of the structure. Reference line 560a is shown primarily for purposes of explanation. This line does not itself depict structure, but rather is primarily just for geometric reference. The same is true for reference lines 560b and 560c in later FIGS.) FIG. 74A may show a balloon-expandable valve with a fabric cuff 80 and a porcine tissue buffer layer (hidden on the inside diameter ("ID") of fabric 80) attached to about 75% of the height of the annulus portion 40 of the stent (i.e., the lower 75% of the annulus portion 40 height). (Stent portion 40 may be called the annulus portion because it is typically implanted in or near the annulus of the patient's native heart valve annulus.) Reference line 560a in FIG. 74A shows the lower portion of the leaflet attached straight across from the bottom eyelet 22 of one commissure post 20 to the next commissure post 20. See also FIG. 75, which shows an example of such a leaflet 60 with reference line 560a superimposed on it.

FIG. 74B may show a self-expanding valve with the fabric cuff 80 and porcine tissue buffer (hidden on ID of the fabric) attached to the full height of the annulus portion 40 of the stent. As indicated by the reference line 560b, a typical leaflet 60 is attached part of the way up the posts 20, and the belly section of the leaflet gradually contours (curves) toward the stent base below the posts (see also FIGS. 76A-B, which are discussed below).

FIG. 74C may show a self-expanding valve with the fabric cuff 80 on the outside diameter ("OD") of the stent and porcine tissue buffer (not visible) on the ID of the stent. (Note that FIG. 74C shows cuff 80 as though transparent, and that this FIG. omits depiction of the sutures that are typically used to secure cuff 80 to the stent frame.) As shown by the reference line 560c, a typical leaflet 60 in this case is attached near the bottom of the posts 20, and the leaflet belly section gradually contours toward the stent base, at which point it can be attached to the base of the stent, cuff 80, and features like those shown in FIGS. 66-68.

FIGS. 76A-B show an illustrative variation of a commissure post 20 (e.g., as in FIG. 63) and the matching leaflet 60 (e.g., as in FIG. 74B). From FIGS. 76A-B it can be seen how the leaflet 60 matches up with various features of the stent post 20 as described earlier (e.g., in connection with FIG. 74B). Note that the two bottom eyelets 23e are not needed for leaflet attachment, but are present for cuff 80 securement. Also, the pair of eyelets 23d' are placed slightly farther apart than the eyelet pairs above to aid in the transition of the leaflet contour (curve).

Figure 77A:
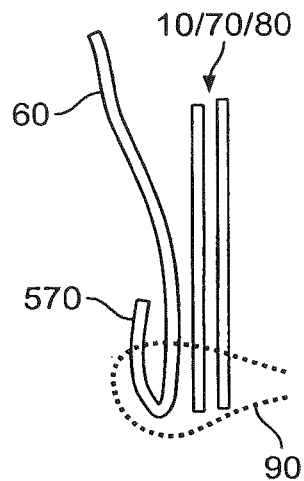
FIGS. 77A-G are simplified sectional views showing various illustrative embodiments of leaflet attachment to other components of valves in accordance with the invention.
Figure 77B:
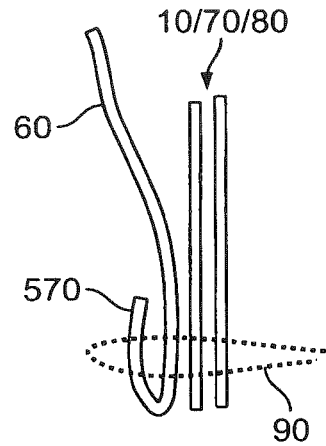
Figure 77C:
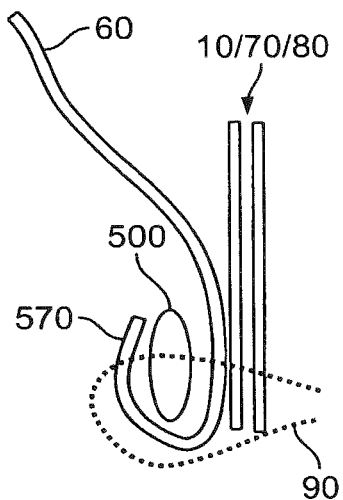
Figure 77D:
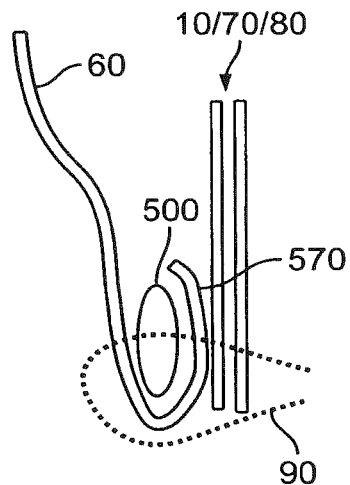
Figure 77E:
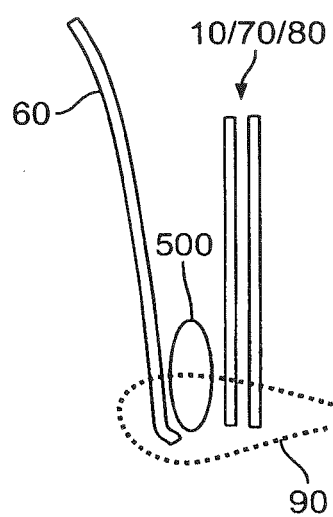
Figure 77F:
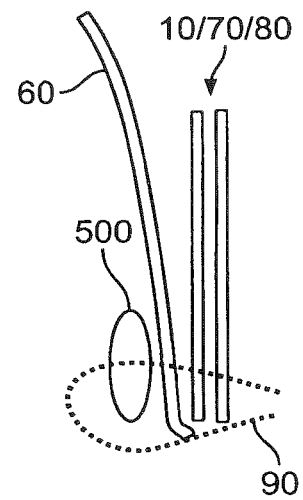
Figure 77G:
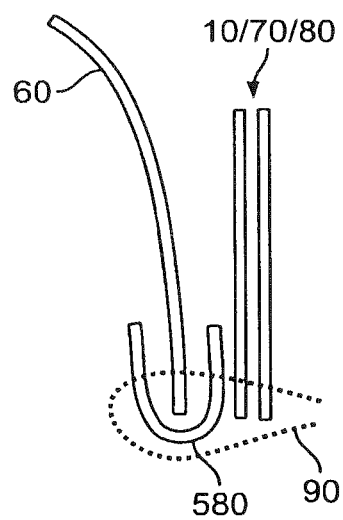

FIGS. 77A-G illustrate several ways that leaflets can be assembled to other components of the valve. Whereas FIGS. like 69A-B focus on the area of leaflet attachment to commissure posts 20, FIGS. like 77A-G can apply to leaflet attachment elsewhere than at commissure posts 20. In each of these FIGS. the double vertical lines represent any desired arrangement and/or combination of elements like stent 10 (e.g., annulus portion 40), buffer layer 70, and/or cuff layer 80. Element 60 is leaflet material, element 90 is suture material, and element 500 is a reinforcing core (e.g., as in FIGS. 69A-B). The bottom portion 570 of a leaflet 570 can be folded and/or supported with core material 500 to create a stronger seam. This seam can then be secured to the cuff 80 and/or stent 10/40 via suture 90 using a variety of techniques. For example, the stitch 90 shown in FIG. 77A pierces through the layers of leaflet tissue 60/570 once and whips around the bottom. The stitch shown in FIG. 77B pierces through the layers of tissue 60/570 twice. A reinforced core 500 (FIGS. 77C-F) can be placed inside the folded leaflet 60/570. The leaflet (main portion 60) can be folded between the cuff 80 and the core 500 as shown in FIG. 77C. Alternatively, the main portion of the leaflet 60 can pass in front of the core 500 as shown in FIG. 77D. With the addition of a core 500, the leaflet 60 may not need to be folded at all, but may simply be attached to the front/back of the core as shown in FIGS. 77E and 77F, respectively. Yet another option is to use a foldable core material 580, by which to sandwich the end of the leaflet 60 as shown in FIG. 77G. As noted earlier (e.g., in connection with FIGS. 69A-B), the material of a reinforcing core can be other tissue, polymer, metal and/or fabric. Thus a reinforcing core like 500 or 570 can be rigid (e.g., metal or the like) or soft (e.g., fabric, tissue, or the like). The reinforcement can run along dotted suture lines shown on the leaflets in some of the FIGS. herein (e.g., line 575 in FIG. 76B) or any portion of such a suture line. Rigid reinforcement members may have eyelets parallel and/or perpendicular to post 20 eyelets.

Figure 78A:
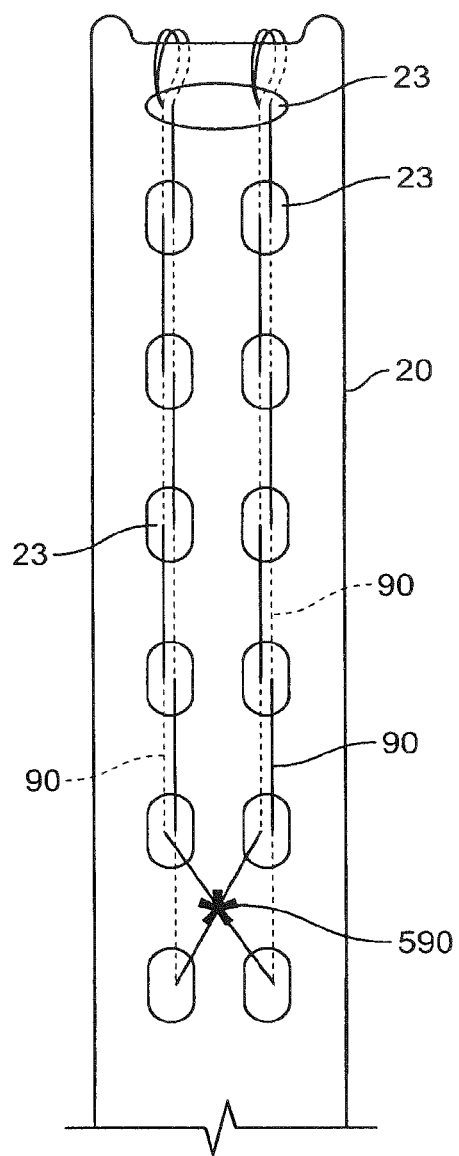
FIGS. 78A and 78B are each similar to FIGS. like FIGS. 53A-B for other illustrative embodiments.
Figure 78B:
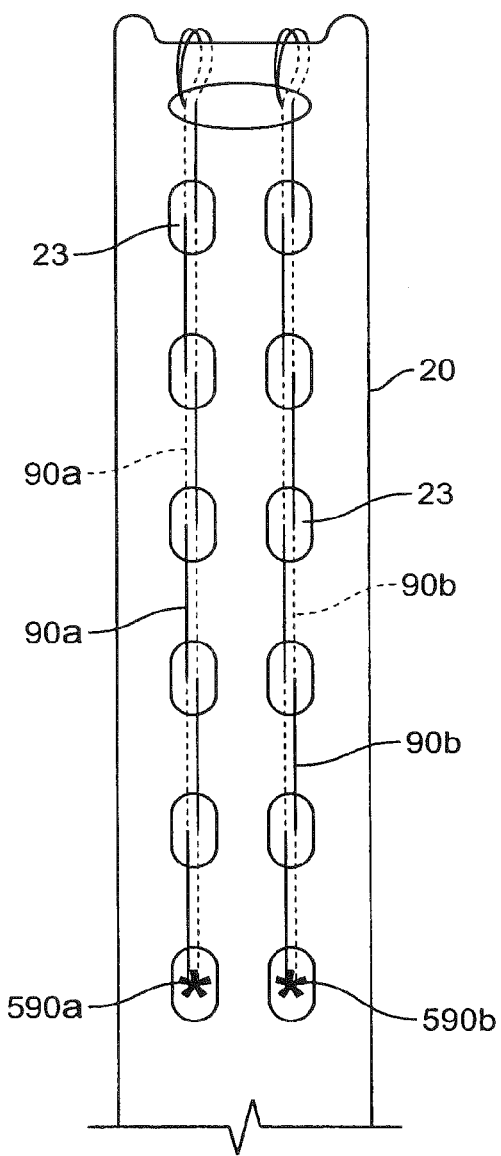

FIGS. 78A and 78B show some examples of suture patterns that may be used to attach leaflet flaps to commissure posts 20. In FIG. 78A one suture 90 is used to attach a leaflet flap to a post 20. Beginning at the bottom right eyelet, the suture 90 is temporarily anchored at or near 590 where a suture tail remains. Suture 90 then runs from the bottom eyelet 23 to the top (back and forth through successive eyelets and a leaflet flap (not shown)) and then returns back down the same side (again back and forth through successive eyelets and the above-mentioned leaflet flap). Suture 90 then crosses over near 590 to the other column of eyelets to repeat the same pattern. Ultimately the suture end is tied off to the suture tail at 590.

In the alternative shown in FIG. 78B, each side of the post eyelets (i.e., the left side eyelets or the right side eyelets) are sutured independently (suture 90a starting from 590a on the left, and suture 90b starting from 590b on the right), and each suture is ultimately tied off to its own tail at 590a or 590b, respectively.

To some extent the appended claim terminology may differ from terminology used up to this point in this detailed description. Some specific examples of what certain claim terms refer to are as follows. Supporting structure 10; sheet-like, flexible, leaflet member 60/160; free edge portion of a leaflet 61; flexible chord across an interior of the supporting structure (see, for example, reference number 131 in FIG. 18A or FIG. 20A; such a chord is typically not a straight chord, but rather a loose and flexible chord); material of the leaflet beyond an end of the chord forming a flap 62; cylindrical surface defined by one of the inner and outer surfaces of the supporting structure (such cylindrical surfaces are abstract geometric shapes defined by what are earlier referred to, respectively, as the ID (inside diameter) and OD (outside diameter) of supporting structure 10; these cylindrical surfaces are not necessarily round, but may instead have other shapes such as oval, elliptical, etc.); suture 90; inner surface of the supporting structure (ID of supporting structure 10); outer surface of the supporting structure (OD of supporting structure 10); secured line portion(s) 67/170/250/300b; belly portion of the leaflet 63/190/310; additional material of the leaflet beyond the secured line portion away from the belly portion forming a second flap 64/240/270/62b; axial end of the supporting structure, e.g., lower end of structure 10 as viewed in FIG. 1a; sheet-like, flexible, buffer material 70; annularly spaced commissure posts 20a-c; cantilevered from other structure of the supporting structure, e.g., commissure posts 20 may have upper free end portions and are only attached to the remainder of supporting structure 10 below those upper free end portions (this cantilevering of the upper free end portions of the commissure posts gives the commissure posts what is sometimes referred to herein as independent flexibility, which means, for example, that the upper free end portion of a commissure post can flex radially inwardly and outwardly at least somewhat independently of other portions of supporting structure 10) (note that in FIG. 65 the posts 20 are not cantilevered, but the entire stent frame flexes to reduce stress); commissure post bifurcated into two spaced apart members, e.g., the commissure post portions on opposite sides of notch or opening 24; annular, annularly collapsible and re-expandable substructures 42a-c that are spaced from one another along an axis about which the supporting structure is annular; linking members 44 that are substantially parallel to the above-mentioned axis and that interconnect the above-mentioned substructures 42a-c; sheet of flexible leaflet material 160 having a central opening 150 with three sides 61; leaflet-linking areas 180; the sheet 160 continues radially outwardly beyond at least a portion of at least one of the secured line portions 250 to form a flap 240/270; a plurality of members disposed in a zig-zag pattern, e.g., 42c, that extends in a direction that is annular of the supporting structure; at least two of the members (e.g., the two members that meet at 440) meeting at an apex 440 that points away from the supporting structure parallel to an axis about which the supporting structure is annular; a sheet of flexible material 70 and/or 80 secured to the supporting structure; a plurality of flexible leaflets 60/160; suture attachment 90 at the apex 440; the apex 440 includes an eyelet 21; an enlarged head 450 on the end of a reduced neck 452; a notch 460; the notch is narrowed near its entrance 462. The examples for certain claim terms provided in this paragraph are only illustrative. As just one example of this, not all of the reference numbers that are used for certain features and elements in certain FIGS. are repeated in every FIG. for every reoccurrence of the same or similar features or elements.

It will be understood that the foregoing is only illustrative of the principles of the invention, and that various modifications can be made by those skilled in the art without departing from the scope and spirit of the invention. For example, the number of cells employed in the stents in valves in accordance with the invention can be different from the numbers shown in the various illustrative embodiment described above.

What is claimed is:
1. A prosthetic heart valve comprising:
an annularly collapsible and re-expandable supporting structure extending between an inflow end and an outflow end;
a plurality of leaflets disposed inside the supporting structure; and
a lower skirt disposed adjacent the inflow end of the supporting structure, the lower skirt including a single continuous sheet that extends from a luminal surface of the supporting structure, wraps around the inflow end and extends over a portion of the abluminal surface of the supporting structure, wherein the lower skirt includes a first portion disposed on the luminal surface of the supporting structure and a second portion disposed on the abluminal surface of the supporting structure and the first portion and the second portion are coupled together at a top edge of the second portion.

2. A prosthetic heart valve comprising:

an annularly collapsible and re-expandable supporting structure extending between an inflow end and an outflow end;

a plurality of leaflets disposed inside the supporting structure; and a lower skirt disposed adjacent the inflow end of the supporting structure, the lower skirt including a single continuous sheet that extends from a luminal surface of the supporting structure, wraps around the inflow end and extends over a portion of the abluminal surface of the supporting structure, the lower skirt including a first portion disposed on the luminal surface of the supporting structure and a second portion disposed on the abluminal surface of the supporting structure;

wherein the first portion and the second portion are sutured together at a top edge of the second portion.

3. A prosthetic heart valve comprising:

an annularly collapsible and re-expandable supporting structure extending between an inflow end and an outflow end;

a plurality of leaflets disposed inside the supporting structure; and a lower skirt disposed adjacent the inflow end of the supporting structure, the lower skirt including a single continuous sheet that extends from a luminal surface of the supporting structure, wraps around the inflow end and extends over a portion of the abluminal surface of the supporting structure, the lower skirt including a first portion disposed on the luminal surface of the supporting structure and a second portion disposed on the abluminal surface of the supporting structure;

wherein the supporting structure includes a plurality of cells arranged in rows and the second portion extends over at least a portion of one of the plurality of cells.

4. The valve defined in claim 3, wherein the plurality of flexible leaflets includes three leaflets.

5. The valve defined in claim 3, wherein the supporting structure includes a stent formed of a plurality of struts.

6. The valve defined in claim 3, wherein the lower skirt comprises a fabric.

* * * * *